(12) United States Patent
Mannarino et al.

(10) Patent No.: US 12,194,198 B2
(45) Date of Patent: Jan. 14, 2025

(54) HIGH STRENGTH POROUS MATERIALS FOR CONTROLLED RELEASE

(71) Applicant: Access Vascular, Inc., Bedford, MA (US)

(72) Inventors: Matthew M. Mannarino, Burlington, MA (US); Daniel T. Donahue, Somerville, MA (US); Michael Bassett, Hampton, NH (US); James F. Biggins, Waltham, MA (US)

(73) Assignee: Access Vascular, Inc., Billerica, MA (US)

( * ) Notice: Subject to any disclaimer, the term of this patent is extended or adjusted under 35 U.S.C. 154(b) by 1248 days.

(21) Appl. No.: 16/719,753

(22) Filed: Dec. 18, 2019

(65) Prior Publication Data

US 2020/0230295 A1    Jul. 23, 2020

Related U.S. Application Data

(60) Provisional application No. 62/782,186, filed on Dec. 19, 2018.

(51) Int. Cl.
*A61L 29/16* (2006.01)
*A61K 9/70* (2006.01)
(Continued)

(52) U.S. Cl.
CPC ............ *A61L 29/16* (2013.01); *A61K 9/7023* (2013.01); *A61K 31/155* (2013.01);
(Continued)

(58) Field of Classification Search
CPC ......... A61M 2025/0057; A61M 31/002; A61L 31/146; A61L 31/16; A61L 29/16;
(Continued)

(56) References Cited

U.S. PATENT DOCUMENTS

| 3,220,960 | A | 11/1965 | Vaclavkova |
| 3,566,874 | A | 3/1971 | Shepherd et al. |

(Continued)

FOREIGN PATENT DOCUMENTS

| CN | 1579601 A | 2/2005 |
| CN | 102580145 A | 7/2012 |

(Continued)

OTHER PUBLICATIONS

International Search Report and Written Opinion for PCT/US2019/067171 mailed Jul. 7, 2020.
(Continued)

*Primary Examiner* — Yan Lan
(74) *Attorney, Agent, or Firm* — Wolf, Greenfield & Sacks, P.C.

(57) ABSTRACT

High strength biomedical materials and processes for making the same are disclosed. Included in the disclosure are nanoporous hydrophilic solids that can be extruded with a high aspect ratio to make high strength medical catheters and other devices with lubricious and biocompatible surfaces. Biologically active agents may be entrapped in pores of materials to provide a controlled release of the biologically active agent.

22 Claims, 19 Drawing Sheets

(51) Int. Cl.
    *A61K 31/155*     (2006.01)
    *A61K 31/445*     (2006.01)
    *A61L 29/04*     (2006.01)
    *A61L 29/06*     (2006.01)
    *A61L 29/14*     (2006.01)
    *A61L 31/06*     (2006.01)
    *A61L 31/14*     (2006.01)
    *A61L 31/16*     (2006.01)
    *A61L 29/02*     (2006.01)
    *A61L 29/18*     (2006.01)

(52) U.S. Cl.
    CPC .......... *A61K 31/445* (2013.01); *A61L 29/049* (2013.01); *A61L 29/06* (2013.01); *A61L 29/14* (2013.01); *A61L 29/145* (2013.01); *A61L 29/146* (2013.01); *A61L 31/06* (2013.01); *A61L 31/146* (2013.01); *A61L 31/16* (2013.01); *A61L 29/02* (2013.01); *A61L 29/18* (2013.01); *A61L 2300/802* (2013.01)

(58) Field of Classification Search
    CPC .. A61L 29/049; A61L 2300/802; A61L 29/02; A61L 29/041; A61L 29/06; A61L 29/126; A61L 29/14; A61L 29/145; A61L 29/146; A61L 29/18; A61L 31/06; C08L 29/04; C08L 33/02; A61K 31/155; A61K 31/445; A61K 9/7023
    See application file for complete search history.

(56) References Cited

U.S. PATENT DOCUMENTS

| | | |
|---|---|---|
| 3,995,623 A | 12/1976 | Blake et al. |
| 4,024,873 A | 5/1977 | Antoshkiw et al. |
| 4,026,296 A | 5/1977 | Stoy et al. |
| 4,073,733 A | 2/1978 | Yamauchi et al. |
| 4,379,874 A | 4/1983 | Stoy |
| 4,543,102 A | 9/1985 | Defago et al. |
| 4,663,358 A | 5/1987 | Hyon et al. |
| 4,943,618 A | 7/1990 | Stoy et al. |
| 5,061,254 A | 10/1991 | Karakelle et al. |
| 5,225,120 A | 7/1993 | Gravier et al. |
| 5,336,205 A | 8/1994 | Zenzen et al. |
| 5,443,727 A | 8/1995 | Gagnon |
| 5,449,382 A | 9/1995 | Dayton |
| 5,508,036 A | 4/1996 | Bakker et al. |
| 5,523,335 A | 6/1996 | Whyzmuzis et al. |
| 5,578,075 A | 11/1996 | Dayton |
| 5,601,538 A | 2/1997 | Deem |
| 5,679,400 A | 10/1997 | Tuch |
| 5,688,459 A | 11/1997 | Mao et al. |
| 5,820,918 A | 10/1998 | Ronan et al. |
| 5,928,279 A | 7/1999 | Shannon et al. |
| 6,099,562 A | 8/2000 | Ding et al. |
| 6,231,605 B1 | 5/2001 | Ku |
| 6,271,278 B1 | 8/2001 | Park et al. |
| 6,656,206 B2 | 12/2003 | Corcoran et al. |
| 6,706,024 B2 | 3/2004 | Modak et al. |
| 7,112,298 B2 | 9/2006 | Kampa et al. |
| 7,329,695 B2 | 2/2008 | Tucker et al. |
| 7,455,674 B2 | 11/2008 | Rose |
| 7,485,670 B2 | 2/2009 | Ruberti et al. |
| 7,619,009 B2 | 11/2009 | Ruberti et al. |
| 7,631,760 B2 | 12/2009 | Guelzow et al. |
| 7,745,532 B2 | 6/2010 | Ruberti et al. |
| 7,845,670 B2 | 12/2010 | Oberg |
| 8,017,139 B2 | 9/2011 | Thomas et al. |
| 8,313,760 B2 | 11/2012 | Hunter et al. |
| 8,470,035 B2 | 6/2013 | Cruise et al. |
| 8,541,484 B2 | 9/2013 | Choi et al. |
| 8,637,063 B2 | 1/2014 | Kopesky et al. |
| 8,784,893 B2 | 7/2014 | Daniloff et al. |
| 8,821,583 B2 | 9/2014 | Myung et al. |
| 9,216,268 B2 | 12/2015 | Liu et al. |
| 10,182,985 B2 | 1/2019 | Bellinger et al. |
| 10,471,183 B2 | 11/2019 | Biggins et al. |
| 10,485,898 B2 | 11/2019 | Biggins et al. |
| 11,389,570 B2 | 7/2022 | Biggins et al. |
| 11,577,008 B2 | 2/2023 | Bassett et al. |
| 11,992,627 B2 | 5/2024 | Bassett et al. |
| 2001/0002411 A1 | 5/2001 | Ronan et al. |
| 2002/0055710 A1* | 5/2002 | Tuch ...................... A61L 31/10 604/103.02 |
| 2002/0138154 A1 | 9/2002 | Li et al. |
| 2004/0092653 A1 | 5/2004 | Ruberti et al. |
| 2004/0247867 A1 | 12/2004 | Chaouk et al. |
| 2006/0240059 A1 | 10/2006 | Bavaro et al. |
| 2006/0287650 A1 | 12/2006 | Cao et al. |
| 2007/0129690 A1 | 6/2007 | Rosenblatt et al. |
| 2008/0065010 A1 | 3/2008 | Bavaro et al. |
| 2008/0075628 A1 | 3/2008 | Judd et al. |
| 2008/0160062 A1* | 7/2008 | Richard .................. A61L 31/04 528/425 |
| 2008/0208347 A1 | 8/2008 | Muratoglu et al. |
| 2009/0010983 A1 | 1/2009 | Melvik et al. |
| 2009/0075267 A1 | 3/2009 | Siena et al. |
| 2009/0076495 A2 | 3/2009 | Dando et al. |
| 2010/0087788 A1 | 4/2010 | Rosenblatt et al. |
| 2010/0105801 A1 | 4/2010 | Choi |
| 2010/0106103 A1 | 4/2010 | Ziebol et al. |
| 2010/0145286 A1 | 6/2010 | Zhang et al. |
| 2010/0152708 A1 | 6/2010 | Li et al. |
| 2010/0204800 A1* | 8/2010 | Thomas .................. C08J 3/075 623/20.14 |
| 2010/0210752 A1 | 8/2010 | Muratoglu et al. |
| 2010/0234815 A1 | 9/2010 | Do et al. |
| 2011/0000846 A1 | 1/2011 | Ishizuka et al. |
| 2011/0027181 A1 | 2/2011 | Amodei et al. |
| 2011/0091515 A1* | 4/2011 | Zilberman ............ A61L 15/425 424/443 |
| 2011/0190683 A1 | 8/2011 | Gellman et al. |
| 2011/0244010 A1* | 10/2011 | Doshi ................ A61K 31/5377 526/318.41 |
| 2013/0046346 A1 | 2/2013 | Thorwarth et al. |
| 2013/0338431 A1 | 12/2013 | Shalon et al. |
| 2014/0045398 A1 | 2/2014 | Zhang et al. |
| 2014/0058251 A1 | 2/2014 | Stigall et al. |
| 2014/0178446 A1 | 6/2014 | Zhu et al. |
| 2014/0287179 A1 | 9/2014 | Kamioka et al. |
| 2016/0015863 A1 | 1/2016 | Gupta et al. |
| 2016/0136389 A1 | 5/2016 | Christian et al. |
| 2017/0143952 A1 | 5/2017 | Siess et al. |
| 2017/0173219 A1 | 6/2017 | Biggins et al. |
| 2017/0182223 A1 | 6/2017 | Biggins et al. |
| 2017/0340867 A1 | 11/2017 | Acisano, III |
| 2018/0200185 A1 | 7/2018 | Labib et al. |
| 2018/0250116 A1 | 9/2018 | Mourhatch et al. |
| 2018/0369454 A1 | 12/2018 | Mannarino et al. |
| 2019/0167942 A1 | 6/2019 | Schonfeldt |
| 2020/0093965 A1 | 3/2020 | Biggins et al. |
| 2021/0069468 A1 | 3/2021 | Keating et al. |
| 2021/0275774 A1 | 9/2021 | Doherty et al. |
| 2022/0088348 A1 | 3/2022 | Bassett et al. |
| 2022/0378984 A1 | 12/2022 | Biggins et al. |
| 2023/0256141 A1 | 8/2023 | Bassett et al. |

FOREIGN PATENT DOCUMENTS

| | | |
|---|---|---|
| CN | 102634865 A | 8/2012 |
| EP | 0 532 037 A1 | 3/1993 |
| EP | 2 075 014 B1 | 7/2011 |
| JP | S52-21420 A | 2/1977 |
| JP | S55-106162 A | 8/1980 |
| JP | S58-014906 A | 1/1983 |
| JP | S61-226061 A | 10/1986 |
| JP | S62-11460 A | 1/1987 |
| JP | H01-299564 A | 12/1989 |
| JP | H10-306191 A | 11/1998 |
| JP | H11-130929 A | 5/1999 |
| JP | 2002-360685 A | 12/2002 |
| JP | 2007-500764 A | 1/2007 |

(56) References Cited

FOREIGN PATENT DOCUMENTS

| | | |
|---|---|---|
| JP | 2012-251057 A | 12/2012 |
| JP | 5820918 B1 | 11/2015 |
| KR | 2018-0110695 A | 10/2018 |
| WO | WO 92/07899 A2 | 5/1992 |
| WO | WO 97/41180 A1 | 11/1997 |
| WO | WO 99/44665 A2 | 9/1999 |
| WO | WO 01/68746 A1 | 9/2001 |
| WO | WO 2007/002004 A2 | 1/2007 |
| WO | WO 2012/122023 A2 | 9/2012 |
| WO | WO 2014/063711 A1 | 5/2014 |
| WO | WO 2014/077886 A1 | 5/2014 |
| WO | WO 2017/112878 A1 | 6/2017 |
| WO | WO 2018/237166 A1 | 12/2018 |
| WO | 2021/168284 A1 | 8/2021 |

OTHER PUBLICATIONS

[No Author Listed], Dimethyl Sulfoxide Physical Properties. Gaylord Chemical Company, L.L.C., Bulletin 101. Jun. 2014. 14 pages.

Chirilia et al., Poly(2-hydroxyethyl methacrylate) sponges as implant materials: in vivo and in vitro evaluation of cellular invasion. Biomaterials. 1993;14(1):26-38.

Fukumori et al., Significant improvement of mechanical properties for polyvinyl alcohol film prepared from freeze/thaw cycled gel. Open Journal of Organic Polymer Materials. 2013;3:110-116.

Kang, The synthesis of nanoporous hydrogels using sacrificial block copolymers. Dissertation. Massachusetts Institute of Technology. Jul. 21, 2006. 106 pages.

Peppas et al., Semicrystalline poly(vinyl alcohol) films and their blends with poly(acrylic acid) and poly(ethylene glycol) for drug delivery applications. Journal of Drug Delivery Science and Technology. 2004;14(4):291-297.

Sandeman et al., Adsorption of anionic and cationic dyes by activated carbons, PVA hydrogels, and PVA/AC composite. J Colloid Interface Sci. Jun. 15, 2011;358(2):582-92. doi: 10.1016/j.jcis.2011.02.031. Epub Feb. 17, 2011.

Speybrouck et al., Successful superior thyroid artery embolisation using microporous beads. European Society for Vascular Surgery. 2012;24:e5-e6.

U.S. Appl. No. 16/586,757, filed Sep. 27, 2019, Biggins et al.

U.S. Appl. No. 16/014,886, filed Jun. 21, 2018, Bassett et al.

Hamada et al., Melting point of polyvinyl alcohol. Polym Chem. 1966;23(254):395-9.

\* cited by examiner

HIGH STRENGTH POROUS MATERIALS FOR CONTROLLED RELEASE

RELATED APPLICATIONS

This application claims priority under 35 U.S.C. § 119(e) to U.S. provisional application, U.S. Application Ser. No. 62/782,186, filed Dec. 19, 2018, which is hereby incorporated by reference in its entirety.

TECHNICAL FIELD

The technical field generally relates to porous biomaterials, including high strength hydrophilic nanoporous biomaterials, e.g., for controlled release of biologically active agents.

BACKGROUND

Biomaterials with high strength, low thrombogenicity, lubricious surface properties and containing a biologically active agent are useful in the medical arts. The porosity of the biomaterials allows for both high strength bulk materials for medical devices and channels for the controlled dissolution of biologically active agents. These biologically active properties may prevent or reduce biofilm, microbial colonization, infection, fibrin sheath formation, inflammation, pain, and/or tumor growth, and/or may treat physiological conditions such as tumor reduction, fungal and bacterial infections, inflammation, and pain. Complications seen with such devices lengthen hospital stays and increase patient morbidity and mortality.

Accordingly, improved devices and methods are needed.

SUMMARY

Biomaterials which may be useful to make medical devices are disclosed herein. In some embodiments, materials and methods are provided herein for the fabrication of tough, lubricious biocompatible biomaterials for a variety of medical device applications. Processing techniques are disclosed to make materials with superior properties such as strength, hemocompatibility, and extended release capabilities over polyurethanes and silicones. Included herein are methods for extrusion of hydrophilic polymers to create high strength, hemocompatible, nanoporous biomaterials or other materials. The porous material may further be made to have polymers or biologically active agents in the pores of the materials. These processes can be performed without the use of chemical crosslinkers or radiation crosslinking. Bulk incorporation of polymers into the pores of the materials is in contrast to a coating or bonding process that covers-over the pores or that relies only on bonding of a surface-treating material to a surface of the bulk material.

In one aspect, devices are provided. In some embodiments, the device comprises a body portion, wherein the body portion is formed of a polymeric material comprising a first water soluble polymer, a biologically active agent associated with the polymeric material, wherein the biologically active agent is distributed within the polymeric material substantially homogeneously, and wherein the device has an elongation at break of greater than or equal to 50% and/or the device has an increase in overall length in an equilibrium water content state of greater than or equal to 1% as compared to an overall length in a dehydrated state.

In some embodiments, the device comprises a body portion, wherein the body portion is formed of a polymeric material comprising a first water soluble polymer, and wherein the body portion comprises a plurality of pores, a second water soluble polymer positioned within at least a portion of the plurality of pores of the body portion, and a biologically active agent associated with the first water soluble polymer and/or the second water soluble polymer, wherein the biologically active agent is distributed within the first water soluble polymer substantially homogeneously.

In some embodiments, the device comprises a body portion, wherein the body portion is formed of a polymeric material comprising a first water soluble polymer, a biologically active agent associated with the polymeric material, wherein the biologically active agent is distributed within the polymeric material substantially homogeneously, and wherein the polymeric material has a Young's elastic modulus of greater than or equal to 500 MPa in a dehydrated state and a Young's elastic modulus of less than or equal to 300 MPa and greater than or equal to 5 MPa at an equilibrium water content state.

In some embodiments, the device comprises a body portion, wherein the body portion is formed of a polymeric material comprising a first water soluble polymer, and a biologically active agent associated with the polymeric material, wherein the biologically active agent is distributed within the polymeric material substantially homogeneously, wherein the polymeric material has a water content of less than 5 w/w % and greater than or equal to 0.1 w/w % in a dehydrated state, and wherein the polymeric material is configured to swell in an amount greater than or equal to 5 w/w % and less than or equal to 50 w/w % from a dehydrated state to an equilibrium water content state in less than or equal to 60 minutes at 25° C.

In some embodiments, the device comprises a body portion wherein the body portion is formed of a polymeric material and comprises the polymeric material comprising a water-soluble polymer and a biologically active agent associated with the polymeric material, wherein the biologically active agent is present in the device in an amount of greater than or equal to 0.01 w/w % versus the total weight of the device in a dehydrated state, and wherein the polymeric material has a Young's elastic modulus of greater than or equal to 500 MPa in the dehydrated state and a Young's elastic modulus of less than or equal to 300 MPa and greater than or equal to 5 MPa at an equilibrium water content state.

In some embodiments, the device is formed of a polymeric material and comprises the polymeric material comprising a first water soluble polymer and a biologically active agent associated with the polymeric material, wherein the biologically active agent is distributed within the polymeric material substantially homogeneously, and wherein the biologically active agent is configured to be released from the polymeric material at a first average rate as determined at 24 hours of release and at a second average rate of at least about 1% of the first average rate after 30 days.

In some embodiments, the device comprises a body portion, wherein the body portion is formed of a polymeric material comprising a first water soluble polymer; and a humectant; wherein the polymeric material has a water content of greater than or equal to 6 w/w % and less than or equal to 40 w/w %; wherein the water content is less than an equilibrium water content state; and wherein the polymeric material is configured to swell in an amount greater than or equal to 2 w/w % to the equilibrium water content state.

In some embodiments, the device comprises a body portion, wherein the body portion is formed of a polymeric material comprising a first water soluble polymer; wherein the polymeric material has a water content of greater than or equal to 6 w/w % and less than or equal to 40 w/w %; wherein the water content is less than an equilibrium water content state; and wherein the polymeric material is configured to swell in an amount greater than or equal to 2 w/w % to the equilibrium water content state in a time period of less than or equal to 60 minutes at 25° C.

In some embodiments, the device comprises a body portion; wherein the body portion is formed of a polymeric material comprising a first water soluble polymer; and wherein the body portion has an inner diameter, an outer diameter, and a length; wherein the polymeric material has a water content of greater than or equal to 6 w/w % and less than or equal to 40 w/w %; wherein the water content is less than an equilibrium water content state; wherein the polymeric material is configured to swell in an amount greater than or equal to 2 w/w % to the equilibrium water content state; and wherein the polymeric material is configured to swell such that the inner diameter and/or outer diameter increase by a larger percentage than the percentage increase in length.

In another aspect, catheters are provided. In some embodiments, the catheter comprises a body portion, wherein the body portion is formed of a polymeric material configured for administration to a subject, comprising the polymeric material and a biologically active agent distributed within the polymeric material substantially homogeneously.

In some embodiments, the catheter comprises a body portion wherein the body portion is formed of a polymeric material configured for administration to a subject, comprising the polymeric material and a biologically active agent distributed within the bulk of the polymeric material, wherein the biologically active agent is present in the catheter in an amount of 0.01 w/w % versus the total catheter weight in a dehydrated state.

In yet another aspect, kits are provided. In some embodiments, the kit comprises a device comprising a body portion, wherein the body portion comprises a polymeric material comprising a first water soluble polymer; and a humectant; wherein the polymeric material has a water content; wherein the water content is less than an equilibrium water content state; and wherein the polymeric material is configured to swell in an amount greater than or equal to 2 w/w % to the equilibrium water content state.

In some embodiments, the kit comprises a device comprising a body portion, wherein the body portion comprises a polymeric material comprising a first water soluble polymer; and wherein the polymeric material has a water content; wherein the water content is less than an equilibrium water content state; and wherein the polymeric material is configured to swell in an amount greater than or equal to 2 w/w % to the equilibrium water content state in a time period of less than or equal to 60 minutes at 25° C.

In some embodiments, the kit comprises a body portion; wherein the body portion comprises a polymeric material comprising a first water soluble polymer; and wherein the body portion has an inner diameter, an outer diameter, and a length; wherein the polymeric material has a water content; wherein the water content is less than an equilibrium water content state; wherein the polymeric material is configured to swell in an amount greater than or equal to 2 w/w % to the equilibrium water content state; wherein the polymeric material is configured to swell such that the inner diameter and/or outer diameter increase by a larger percentage than percentage increase in length.

In yet another aspect, methods, such as methods of treating a subject, are provided. In some embodiments, the method comprises with a mixture comprising a first water soluble polymer and a salt, wherein the first water soluble polymer is present in the mixture in an amount greater than or equal to 13 w/w % versus the total weight of the mixture, performing the steps of extruding the mixture at a temperature greater than or equal to 65° C. on a core material to form a polymeric material disposed on the core material, exposing the polymeric material to a non-solvent of the polymeric material at a temperature less than or equal to 28° C. for greater than or equal to 15 minutes, introducing, to the polymeric material, a solution comprising a biologically active agent, heating the polymeric material and the solution to a temperature of greater than or equal to 30° C., flowing the solution adjacent the polymeric material, and drying the polymeric material, wherein the biologically active agent is distributed within the polymeric material substantially homogeneously to within less than or equal to 50% of an average loading of the biologically active agent in the polymeric material.

In some embodiments, the method of treating a subject comprises administering, into an orifice of a subject, a device comprising: a body portion, wherein the body portion comprises a polymeric material comprising a first water soluble polymer; and a humectant; wherein the polymeric material has a water content, and the water content is less than an equilibrium water content state; and swelling the polymeric material in an amount greater than or equal to 2 w/w % to the equilibrium water content state.

In some embodiments, the method of treating a subject comprises administering, into an orifice of a subject, a device comprising: a body portion, wherein the body portion comprises a polymeric material comprising a first water soluble polymer; wherein the polymeric material has a water content, and the water content is less than an equilibrium water content state; and swelling the polymeric material in an amount greater than or equal to 2 w/w % to the equilibrium water content state in a time period of less than or equal to 60 minutes at 25° C.

In some embodiments, the method of treating a subject comprises administering, into an orifice of a subject, a device comprising: a body portion; wherein the body portion comprises a polymeric material comprising a first water soluble polymer; and wherein the body portion has an inner diameter, an outer diameter, and a length; wherein the polymeric material has a water content, and the water content is less than an equilibrium water content state; and swelling the polymeric material in an amount greater than or equal to 2 w/w % to the equilibrium water content state, such that the inner diameter and/or outer diameter increase by a larger percentage than the percentage increase in length.

In some embodiments, the method comprises administering, into an external orifice of a subject, a device comprising a body portion, wherein the body portion comprises a polymeric material comprising a water-soluble polymer and a biologically active agent associated with the polymeric material, the device having an aspect ratio of greater than or equal to 3:1, wherein the biologically active agent is distributed within the polymeric material substantially homogeneously.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
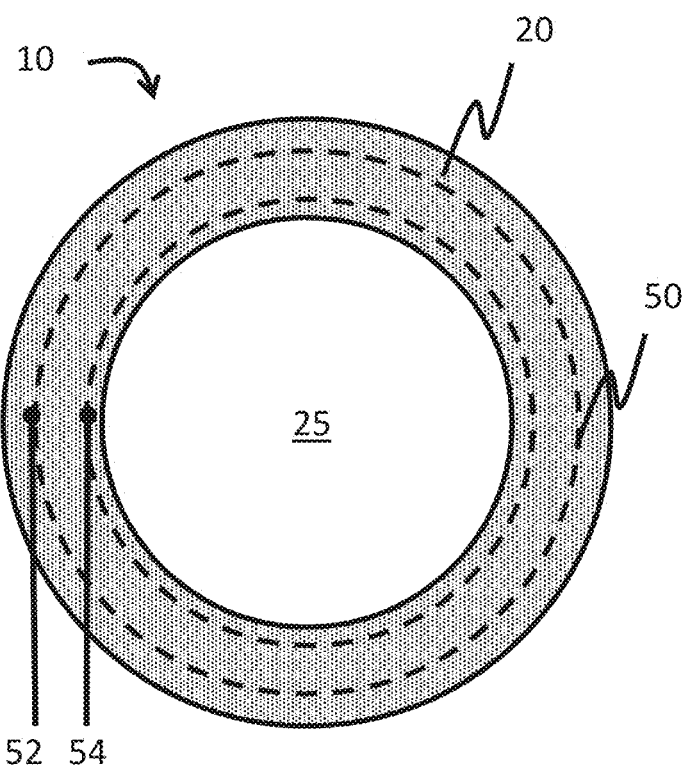
FIG. 1A is a cross-sectional schematic diagram of an exemplary device, according to one set of embodiments.

High strength porous materials incorporating water soluble polymers, are generally provided. For example, materials, methods, and uses are set forth herein for a biomaterial comprising a medically acceptable porous solid. The disclosed compositions and devices may be useful for administration to a subject (e.g., a patient). Advantageously, the compositions and/or devices described herein may be substantially non-thrombogenic, lubricious, and/or biocompatible. In some embodiments, the devices described herein may be useful for the delivery of a biologically active agent (e.g., a therapeutic agent such as a drug) to a subject. In some embodiments, the compositions and/or devices described herein may be suitable for administration to a subject and/or delivery of a biologically active agent for a relatively long period of time, e.g., without the formation of a thrombus, without fouling, and/or without absorbing (or adsorbing) one or more substances (e.g., therapeutic agents, proteins, blood, plasma) internal to the subject. Methods for forming such compositions and/or devices are also provided.

The devices described herein may be useful for a wide variety of applications including, for example, administration of biologically active agents. In some embodiments, therapeutic, antimicrobial, or antiseptic active agents may be incorporated into a bulk material (e.g., a polymeric material) of the device such that the agent is released from the bulk material. In some such embodiments, the biologically active agent may advantageously prevent or reduce biofilm, microbial colonization, infection, fibrin sheath formation, inflammation, pain, and/or tumor growth, and/or may treat physiological conditions such as tumor reduction, fungal and bacterial infections, inflammation, and pain. The devices described herein may be used, in some cases, to make blood-contacting devices or devices that contact bodily fluids, including ex vivo and/or in vivo devices, such as blood contacting implants. Examples of drug delivery devices in which the devices described herein may embody or be incorporated into include but are not limited to medical tubing, wound dressing, contraceptive devices, feminine hygiene, endoscopes, grafts (e.g., including small diameter of less than or equal to 6 mm), pacemakers, implantable cardioverter-defibrillators, cardiac resynchronization devices, cardiovascular device leads, ventricular assist devices, catheters (e.g., including cochlear implants, endotracheal tubes, tracheostomy tubes, ports, shunts), implantable sensors (e.g., intravascular, transdermal, intracranial), ventilator pumps, and ophthalmic devices including drug delivery systems.

In some embodiments, the devices described herein comprise a body portion. For example, as shown illustratively in FIG. 1A, device 10 comprises a body portion 20. In some embodiments, body portion 20 is formed of and/or comprises a polymeric material. The polymeric material may comprise a first water soluble polymer. In some embodiments a biologically active agent 50 is associated with the polymeric material.

In some embodiments, one or more biologically active agents is present throughout the bulk of the polymeric material (e.g., distributed throughout the polymeric material matrix). For example, in some embodiments, a first arbitrary section 52 within a cross-section of body portion 20 comprises a non-zero concentration of a biologically active agent. In some embodiments, a second arbitrary section 54, different than first arbitrary section 52, within a cross-section of body portion 20 comprises a non-zero concentration of the biologically active agent. Those of ordinary skill in the art would understand, based upon the teachings of this specification, that the presence of a biologically active agent within the bulk of a polymeric material (e.g., embedded in the polymer matrix of the polymeric material) is not intended to refer to a coating of a biologically active agent on a polymeric material but, by contrast, is intended to refer to a biologically active agent distributed throughout the bulk of the polymeric material. However, in some embodiments, a coating comprises the biologically active agent may optionally be present. Examples of sections are described in more detail below.

While body portion 20, section 52 and section 54 in FIG. 1A are depicted as circular, those of ordinary skill in the art would understand, based upon the teachings of this specification, that the body portion and other sections in embodiments disclosed herein need not be circular, and other cross-sectional shapes (e.g., planar, rectangular, square, oval, oblong, S-shaped, etc.) are also possible. For example, in some embodiments, the body portion is S-shaped, which can, in some cases, provide ease of implantation in a subject, achieve lower infiltration rates, and reduce the likelihood of dislodgement within the subject.

In some embodiments, the biologically active agent is present in the bulk polymeric material formed as a layer in the device. For example, in some embodiments, the polymeric material comprises a first surface and a second surface wherein the first surface and/or the second surface may be coated. In some embodiments, the first surface and/or the second surface is coated with a polymer, a second biologically active agent (the same or different from the biologically active agent present in the polymeric material), or combinations thereof. In some embodiments, the device comprises two or more layers of polymeric material in the body portion. In some embodiments, each layer of polymeric material may comprise the same, comprising different, or comprise no biologically active agent. In an illustrative embodiment, the body portion of a device comprises a first polymeric material layer comprising a first biologically active agent and a second polymeric material layer disposed on the first polymeric material layer, comprising a second biologically active agent. Other combinations of layers are also possible.

In some embodiments, the biologically active agent is distributed within the polymeric material (of the body portion) and/or the first water soluble polymer substantially homogeneously. For example, in some embodiments, the amount of the biologically active agent does not vary by more than 50% at a given arbitrary section (e.g., section 52, section 54 in FIG. 1A) across a cross-sectional area of the body portion and/or first water soluble polymer as compared to an average amount of the biologically active agent in the body portion and/or first water soluble polymer.

In some embodiments, the biologically active agent is distributed within the polymeric material non-homogeneously (i.e., on one or more surfaces of the polymeric material). For example, in some embodiments, the amount of the biologically active agent varies by more than 50% at a given arbitrary section (e.g., section 52, section 54 in FIG. 1A) across a cross-sectional area of the body portion and/or first water soluble polymer as compared to an average amount of the biologically active agent in the body portion and/or first water soluble polymer.

In some embodiments, the biologically active agent is distributed within the body portion (or polymeric material of the body portion) and/or first water soluble polymer to within greater than or equal to 0.1%, greater than or equal to 1%, greater than or equal to 2%, greater than or equal to 5%, greater than or equal to 10%, greater than or equal to 15%, greater than or equal to 20%, greater than or equal to 25%, greater than or equal to 30%, greater than or equal to 35%, greater than or equal to 40%, greater than or equal to 45%, greater than or equal to 50%, greater than or equal to 60%, greater than or equal to 70%, greater than or equal to 80%, greater than or equal to 90%, greater than or equal to 95%, or greater than or equal to 98% of an average loading of the biologically active agent in the body portion (or polymeric material) and/or first water soluble polymer. In some embodiments, the biologically active agent is distributed within the body portion (or polymeric material of the body portion) and/or first water soluble polymer to within less than or equal to 99%, less than or equal to 98%, less than or equal to 95%, less than or equal to 90%, less than or equal to 80%, less than or equal to 70%, less than or equal to 60%, less than or equal to 50%, less than or equal to 45%, less than or equal to 40%, less than or equal to 35%, less than or equal to 30%, less than or equal to 25%, less than or equal to 20%, less than or equal to 15%, less than or equal to 10%, less than or equal to 5%, or less than or equal to 2% of an average loading of the biologically active agent in the body portion (or polymeric material) and/or first water soluble polymer. Combinations of the above-referenced ranges are possible (e.g., less than or equal to 99% and greater than or equal to 0.1%, less than or equal to 50% and greater than or equal to 1%). Other ranges are also possible.

The loading of the biologically active agent may be determined at a position within the body portion (or polymeric material) by sectioning the body portion followed by extraction and liquid chromatography. By way of example, an article formed of the body portion (e.g., article 10 of FIG. 1A) may be cut along a cross-sectional dimension through its central axis and flattened. Three or more sections of the flattened body portion (e.g., a top section, a central section, and a bottom section) may be sliced across the length and/or width of the body portion and the biologically active agent is extracted from each section. The amount of biologically active agent present in each section may be determined by liquid chromatography. The highest amount of variance among the sections measured (compared to an average loading) constitutes the variance of the article or device. For example, if the biologically active agent is distributed within the body portion at variance levels of 5% of an average loading from a top section, 15% of an average loading at a middle section, and 10% of an average loading at a bottom section, the article/device comprising the body portion will have a variance of 15% of an average loading. Such an article/device would be said to have a biologically active agent that is distributed within the body portion (or polymeric material of the body portion) to within less than or equal to 15% of an average loading of the biologically active agent in the body portion (or polymeric material), and the biologically active agent would be considered substantially homogenously dispersed within the body portion. By contrast, and by way of example only, an article which comprises a coating of biologically active agent deposited on an external surface of the body portion (e.g., a coated catheter), in which no biologically active agent is present in the bulk polymeric material of the body portion, would not be considered to have a biologically active agent distributed within the body portion within less than or equal to 15% of an average loading, as loading in a first section (e.g., a top section comprising the coating) of the body portion would vary by more than 15% from the average loading of the biologically active agent in the body portion (or polymeric material). As such, one of ordinary skill in the art would understand, based upon the teachings of this specification, that articles or devices comprising a coating of biologically active agent, in which no biologically active agent is present in the bulk polymeric material of the body portion, do not have the biologically active agent distributed within the polymeric material (of the body portion) substantially homogeneously (e.g., within 50% of an average loading).

In embodiments in which more than one layer of polymeric material is present in the device, each layer of polymeric material may comprise a biologically active agent distributed homogeneously or non-homogeneously throughout each polymeric material in one or more of the ranges described above.

In some embodiments, the amount of the biologically active agent does not vary by more than 50% (or any combinations of the percentages noted above) at least 2, 4, 6, 8, 10, 20, or 30 arbitrary sections of the body portion. In some embodiments, the arbitrary section is randomly chosen across a length and/or width of the polymeric material forming the body portion.

It should be appreciated that where more than one biologically active agent is present (e.g., a first and a second biologically active agent present in the polymeric material forming the bulk of the body portion), each biologically active agent may independently be distributed within the polymeric material in one or more of the ranges described above.

In some embodiments, as described in more detail below, the body portion (e.g., the polymeric material) may comprise a plurality of pores. The polymeric material of the body portion may comprise a first water soluble polymer as described herein. In some embodiments, the biologically active agent is distributed within the polymeric material (e.g., the first water soluble polymer) homogeneously or non-homogeneously to within one of the above-noted ranges, but not within the plurality of pores. That is to say, in some embodiments, the plurality of pores may be substantially devoid of the biologically active agent. In some embodiments, the plurality of pores may comprise a second biologically active agent, the same or different than a (first) biologically active agent present within the polymeric material forming the bulk of the device (e.g., the polymeric material comprising a first water soluble polymer). In yet other embodiments, the biologically active agent is present only in the plurality of pores.

In an exemplary set of embodiments, the device is a catheter. In some embodiments, the catheter is configured for administration to a subject. For example, in some embodiments, a catheter is formed of a polymeric material and is configured for administration to a subject, wherein the catheter comprises a biologically active agent distributed within the polymeric material (e.g., distributed homogeneously). In some embodiments, the catheter comprises a body portion, wherein the body portion is formed of a polymeric material comprising a first water soluble polymer, as described herein.

Suitable biologically active agents are described in more detail below and include, for example, pharmaceutical agents (e.g., drugs), calcium salt (e.g., calcium chloride), iron salt (e.g. ferrous sulfate), starch, modified silica, cellulose, amongst others. The term "biologically active agent" as used herein generally refers to an agent which, when administered to a subject, has a physiologically significant effect on at least a portion of the body of the subject. In some embodiments, the compositions and devices (e.g., device 10 of FIG. 1A, device 12 of FIG. 1B, device 14 of FIG. 1C) described herein comprise a body portion having a plurality of pores. The body portion may be formed of a polymeric material comprising a first water soluble polymer. In some embodiments, the body portion further comprises a second water soluble polymer, same or different than the first water soluble polymer. For example, in some embodiments, a second water soluble polymer, same or different than the first water soluble polymer, may be positioned within at least a portion of the plurality of pores. In some embodiments, the second water soluble polymer is positioned within the bulk of the first water soluble polymer. In some embodiments, the second water soluble polymer is substantially homogeneously dispersed within the bulk of the first water soluble polymer. In some embodiments, the second water soluble polymer is substantially non-homogeneously dispersed within the bulk of the first water soluble polymer. While the following embodiments generally refer to devices comprising a second water soluble polymer positioned within the plurality of pores, those of ordinary skill in the art would understand, based upon the teachings of this specification, that a second water soluble polymer need not always be present. Without wishing to be bound by theory, in some embodiments, the presence of a second water soluble polymer positioned within at least a portion of the plurality of the pores of the body portion or first water soluble polymer may decrease the thrombogenicity and/or increase the lubriciousness of the device (e.g., device 12 of FIG. 1B, device 14 of FIB. IC) as compared to devices without the second water soluble polymer positioned within the pores (all other factors being equal). In an exemplary set of embodiments, the first water soluble polymer is polyvinyl alcohol. In another exemplary set of embodiments, the second water soluble polymer is polyacrylic acid. Other water soluble polymers are also possible, as described herein.

In some embodiments, the second water soluble polymer may be considered the same as the first water soluble polymer when they are both polymers of the same monomer(s) but have other characteristics, such as the number of monomer(s) and/or molecular weight, that differ.

In some embodiments, the devices (e.g., device 10 of FIG. 1A, device 12 of FIG. 1B, device 14 of FIG. 1C) and compositions described herein are administered to a subject. In some embodiments, the device may be administered orally, rectally, vaginally, nasally, intravenously, subcutaneously, or uretherally. In some cases, the device may be administered into a cavity, epidural space, vein, artery, orifice, external orifice, and/or abscess of a subject. A non-limiting example of an orifice includes a wound. A non-limiting example of a wound includes a wound orifice that is created for venous access (e.g., created as an insertion site) through the skin.

Figure 1B:
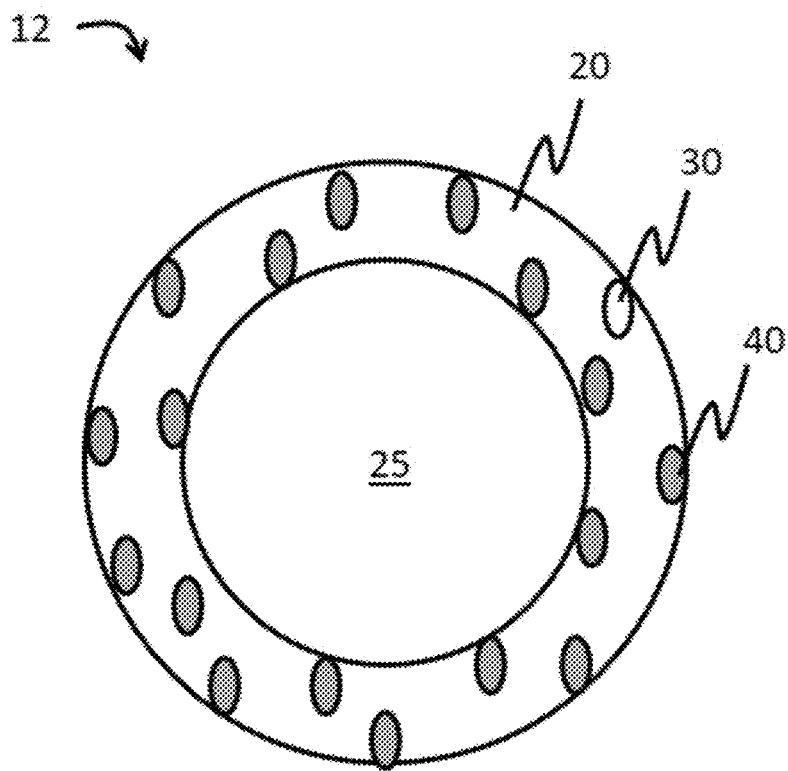
FIG. 1B is a cross-sectional schematic diagram of an exemplary device comprising a plurality of pores, according to one set of embodiments.

As described herein, in some embodiments, the compositions, devices and devices described herein comprise or are formed of a polymeric material comprising a first water soluble polymer having a plurality of pores. For example, as illustrated in FIG. 1B device 12 includes a body portion 20 comprising or formed of a polymeric material comprising a first water soluble polymer and having a plurality of pores 30. In some embodiments, second water soluble polymer 40 is positioned within at least a portion (e.g., at least 10%, at least 20%, at least 30%, at least 40%, at least 50%, at least 60%, at least 70%, at least 80%, at least 90%, at least 95%, at least 98%, at least 99%, at least 99.99%) of the plurality of pores. In some embodiments, second water soluble polymer 40 is positioned within less than or equal to 100%, less than or equal to 90%, less than or equal to 80%, less than or equal to 70%, less than or equal to 60%, less than or equal to 50%, less than or equal to 40%, less than or equal to 30%, less than or equal to 20%, or less than or equal to 10% of the plurality of pores (e.g., at least 10% and less than or equal to 100% of the plurality of pores). Combinations of the above-referenced ranges are also possible.

Figure 1C:
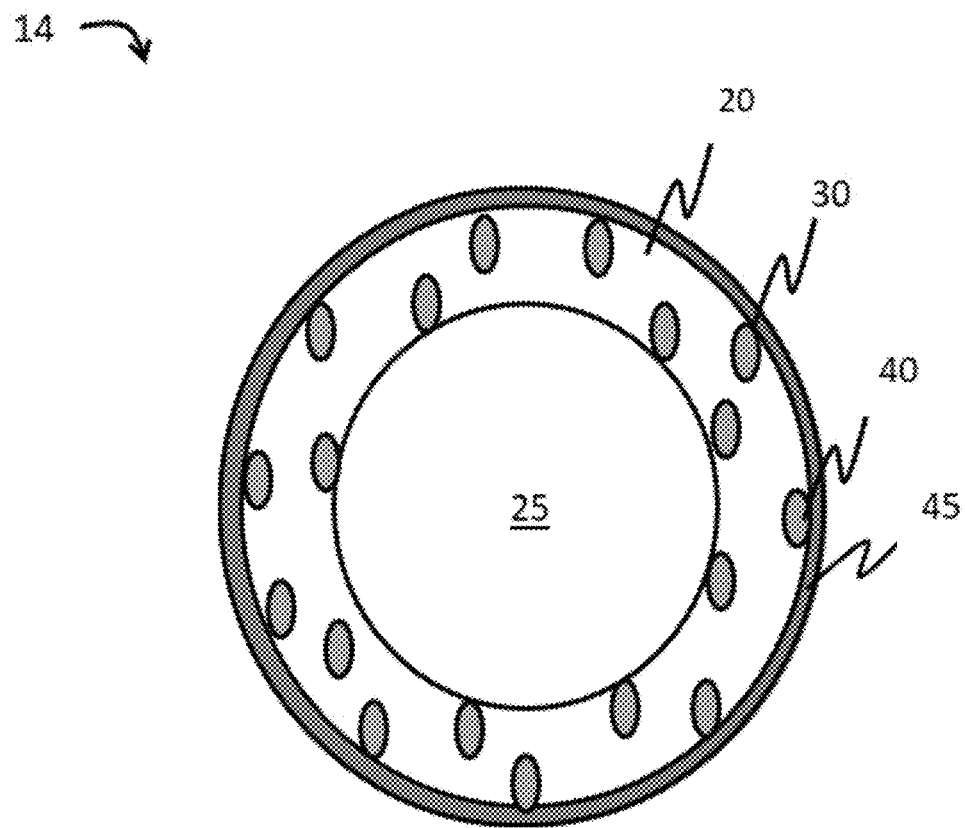
FIG. 1C is a cross-sectional schematic diagram of an exemplary device comprising a plurality of pores, according to one set of embodiments.

In some embodiments, the second water soluble polymer is positioned within (e.g., dispersed within) the bulk of the first water soluble polymer (e.g., within the pores and/or interstices of the first water soluble polymer). In some embodiments, as illustrated in FIG. 1C, the second water soluble polymer 40 may be present as a coating 45 on at least a portion of a surface of body portion 20. Although FIG. 1C shows the second water soluble polymer as a coating on the first water soluble polymer and in the pores of the first water soluble polymer, it should be appreciated that in some embodiments, only a coating 45 is present and the pores 30 are not substantially filled with the second water soluble polymer 40. Other configurations are also possible.

In some embodiments, the devices and/or devices described herein may be hollow (e.g., have a hollow core). For example, device 10 and/or device 12 may be hollow (e.g., comprising a hollow core 25). However, while FIGS. 1A-IC are depicted having a hollow core, those of ordinary skill in the art would understand based upon the teachings of this specification that such a hollow core may not be present. That is to say, in some cases, the core 25 of the device (e.g., device 10 of FIG. 1A, device 12 of FIG. 1B, device 14 of FIG. 1C) may be a bulk material (e.g., a solid core) without a hollow core 25.

As described above, in some embodiments, one or more biologically active agents may be distributed within body portion 20 and/or plurality of pores 30 (FIGS. 1B-1C). In some embodiments, the biologically active agent is a therapeutic agent. As used herein, the term "therapeutic agent" or also referred to as a "drug" refers to an agent that is administered to a subject to treat, reduce, delay, ameliorate and/or prevent a disease, disorder, or other clinically recognized condition, or for prophylactic purposes, and, in some embodiments, has a clinically significant effect on the body of the subject to treat, reduce, delay, ameliorate and/or prevent the disease, disorder, or condition. Therapeutic agents include, without limitation, agents listed in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005. In some embodiments, the therapeutic agent may be selected from "Approved Drug Products with Therapeutic Equivalence and Evaluations," published by the United States Food and Drug Administration (F.D.A.) (the "Orange Book"). In some cases, the therapeutic agent is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention. In some embodiments, the therapeutic agent is a small molecule. Exemplary classes of agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents (e.g., taxanes, such as paclitaxel and docetaxel; cisplatin, doxorubicin, methotrexate, etc.), antihistamines, antimigraine drugs, hormones, prostaglandins, antimicrobials (including antibiotics, antifungals, antivirals, antiparasitics), antimuscarinics, anxiolytics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated. These may be vitamins, supplements such as calcium or biotin, or natural ingredients such as plant extracts or phytohormones.

In some embodiments, the biologically active agent is an anti-inflammatory drug. Non-limiting examples of suitable anti-inflammatory drugs include betamethasone, beclomethasone, budesonide, ciclesonide, dexamethasone, desoxymethasone, fluocinolone acetonide, fluocinonide, flunisolide, fluticasone, icomethasone, rofleponide, triamcinolone acetonide, fluocortin butyl, hydrocortisone aceponate, hydrocortisone buteprate, hydroxycortisone 17-butyrate, prednicarbate, 6-methylprednisolone aceponate, mometasone furoate, elastane, prostaglandin, leukotriene, and bradykinin antagonists.

In some embodiments, the biologically active agent is an anesthetic agent. Non-limiting examples of suitable anesthetic agents include bupivacaine, lidocaine, procaine, and tetracaine.

In some embodiments, the biologically active agent is an antiplatelet agent. Non-limiting examples of suitable antiplatelet agents include clopidogrel, prasugrel, ticagrelor, ticlopidine, cilostazol, vorapaxar, abciximab, eptifibatide, tirofiban, dipyridamole, and terutroban.

In some embodiments, the biologically active agent is an analgesic agent. Non-limiting examples of suitable analgesic agents include paclitaxel, clopidogrel, prasugrel, ticagrelor, aspirin, ibuprofen, naproxen (and other NSAIDs), warfarin, heparin, apixaban, dabigatran, rivaroxaban, and statins.

In some embodiments, the biologically active agent is an antineoplastic agent. Non-limiting examples of suitable antineoplastic agents include paclitaxel, oxaliplatin, fluorouracil (5-FU), docetaxel, methotrexate, doxorubicin, mitoxantrone, teniposide, etoposide, novobiocin, merbarone, and aclarubicin.

In some embodiments, the biologically active agent is an antiseptic agent. Non-limiting examples of suitable antiseptic agents include chlorhexidine, alexidine, iodine, povidone, octenidine, poly biguanides, cetrimides, biphenylol, chlorophene, triclosan, copper, silver, nanosilver, gold, selenium, gallium, taurolidine, cyclotaurolidine, N-chlorotaurine, alcohol, lauroyl arginine ethyl, myristamidopropyl dimethylamine (MAPD), and oleamidopropyl dimethylamine (OAPD).

In some embodiments, the biologically active agent is an antimicrobial agent. Non-limiting examples of suitable antimicrobials include penicillins: benzylpenicillins (e.g., penicillin-G-sodium, clemizole penicillin, benzathine penicillin G); phenoxypenicillins (e.g., penicillin V, propicillin); aminobenzylpenicillins (e.g., ampicillin, amoxycillin, bacampicillin), acylaminopenicillins (e.g., azlocillin, mezlocillin, piperacillin, apalcillin), carboxypenicillins (e.g., carbenicillin, ticarcillin, temocillin), isoxazolyl penicillins (e.g., oxacillin, cloxacillin, dicloxacillin, flucloxacillin), amidine penicillin (e.g., mecillinam), cephalosporins, for example: cefazolins (e.g., cefazolin, cefazedone); cefuroximes (e.g., cerufoxime, cefamandole, cefotiam); cefoxitins (e.g., cefoxitin, cefotetan, latamoxef, flomoxef); cefotaximes (e.g., cefotaxime, ceftriaxone, ceftizoxime, cefmenoxime); ceftazidimes (e.g., ceftazidime, cefpirome, cefepime); cefalexins (e.g., cefalexin, cefaclor, cefadroxil, cefradine, loracarbef, cefprozil); cefiximes (e.g., cefixime, cefpodoxime proxetil, cefuroxime axetil, cefetamet pivoxil, cefotiam hexetil), carbapenems; imipenem; cilastatin; meropenem; biapenem monobactams; gyrase inhibitors: ciprofloxacin, gatifloxacin, norfloxacin, ofloxacin, levofloxacin, pefloxacin, lomefloxacin, fleroxacin, clinafloxacin, sitafloxacin, gemifloxacin, balofloxacin, trovafloxacin, moxifloxacin, rifampicin, minocycline, tetracycline, erythromycin, roxithromycin, azithromycin, clarithromycin, sulfonamides, and aminoglycosides; and combinations thereof.

In some embodiments, the biologically active agent is a coagulative agent. Non-limiting examples of suitable coagulative agents include cellulose, oxidized cellulose, tranexamic acid, aprotinin, epsilon-aminocaproic acid, aminomethylbenzoic acid, fibrinogen, and calcium salts.

In some embodiments, the biologically active agent is a biologic entity. Non-limiting examples of suitable biologic entities include peptides and peptide oligomers: insulin, adrenocorticotropic hormone, calcitonin, oxytocin, vasopressin, octreotide, leuprorelin, exenatide, carfilzomib, bortezomib, lixisenatide, voclosporin, daptomycin, glatiramer, rindopepimut, dulaglutide, trebananib, lutetium, romiplostim, liraglutide, peginesatide, zoptarelin, tesamorelin, lucinactant, pasireotide, linaclotide, teduglutide, albiglutide, dulaglutide, afamelanotide, etelcalcetide, plecanatide; checkpoint inhibitors: PD-1, CTLA-4, PD-L1; immune cell therapeutics: tumor-infiltrating lymphocytes (TILs), chimeric antigen receptor (CAR), tisagenlecleucel, axicabtagene ciloleucel; therapeutic antibodies: trastuzumab, rituximab, ofatumumab, alemtuzumab, ado-trastuzumab emtansine, brentuximab vedotin, blinatumomab; therapeutic vaccines: sipuleucel-T, talimogene laherpaepvec; and immune-modulating agents: cytokines, *bacillus* Calmette-Guèrin (BCG), thalidomide, lenalidomide, pomalidomide, imiquimod.

In some embodiments, the biologically active agent comprises a natural and/or synthetic cannabinoid or derivatives thereof.

It should be appreciated that where more than one biologically active agent is present (e.g., a first biologically active agent present in the polymeric material forming the bulk of the body portion, or a second biologically active agent in the pores of the body portion), each biologically active agent may independently be one of the active agents described above.

The biologically active agent (e.g., first, second biologically active agent) may be distributed within the body portion and/or the polymeric material and present in the device in any suitable amount. In some embodiments, the biologically active agent is present in the body portion or polymeric material of the device in an amount ranging between about 0.01 wt % and about 50 wt % versus the total device weight in a device in a first configuration (e.g., a water content less than the equilibrium water content state, such as the dehydrated state). In some embodiments, the biologically active agent is present in the body portion of the device in an amount of at least about 0.01 wt %, at least about 0.05 wt %, at least about 0.1 wt %, at least about 0.5 wt %, at least about 1 wt %, at least about 2 wt %, at least about 3 wt %, at least about 5 wt %, at least about 10 wt %, at least about 20 wt %, at least about 30 wt %, at least about 40 wt % versus the total device weight in a first configuration (e.g., a water content less than the equilibrium water content state, such as the dehydrated state). In some embodiments, the biologically active agent is present in the body portion or polymeric material of the device in an amount of less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 3 wt %, less than or equal to about 2 wt %, less than or equal to about 1 wt %, less than or equal to about 0.5 wt %, less than or equal to about 0.1 wt %, or less than or equal to about 0.05 wt %. Combinations of the above-referenced ranges are also possible (e.g., between about 0.01 wt % and about 50 wt %). Other ranges are also possible. It should be appreciated that where more than one biologically active agent is present (e.g., a first biologically active agent present in the polymeric material forming the bulk of the body portion, or a second biologically active agent in the pores of the body portion), each biologically active agent may independently be present in amounts within one or more ranges described above.

The devices, catheters, kits, and methods described herein may be administered to any suitable subject. The term "subject", as used herein, refers to an individual organism such as a human or an animal. In some embodiments, the subject is a mammal (e.g., a human, a non-human primate, or a non-human mammal), a vertebrate, a laboratory animal, a domesticated animal, an agricultural animal, or a companion animal. Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the device.

Advantageously, the devices described herein may permit higher concentrations (weight percent) of active agents such as biologically active agents to be incorporated into the devices as compared to certain other devices (e.g., certain devices including solely a coating of the biologically active agent). In some embodiments, the biologically active agent is associated with the first water soluble polymer and/or the second water soluble polymer. In some embodiments, the biologically active agent is dispersed within the first water soluble polymer and/or the second water soluble polymer. Additionally, or alternatively, the devices described herein may permit extended release of one or more biologically active agents compared to certain other devices (e.g., certain devices including solely a coating of the biologically active agent).

In some embodiments, the biologically active agent may be released from the body portion of the device by any suitable means. In some embodiments, the biologically active agent is released by diffusion out of the body portion (e.g., the polymeric material of the body portion). In some embodiments, the biologically active agent is released by degradation of at least a portion of the body portion (e.g., biodegradation, enzymatic degradation, hydrolysis of the polymeric material forming the body portion, or of the polymeric material in the pores of the body portion). In some embodiments, the active substance is released from the device at a particular rate. Those skilled in the art would understand that the rate of release may be dependent, in some embodiments, on the solubility of the biologically active agent in the medium in which the device is exposed, such as a physiological fluid such as blood. In some embodiments, the release rate may be dependent on the cross-link density, porosity, pore size distribution, pore interconnectivity (e.g., tortuosity), crystallinity, and/or number of biologically active agent containing layers, in the device (e.g., the body portion of the device).

In some embodiments, between 0.05 wt % to 99 wt % of the biologically active agent is released between 24 hours and 1000 days after administration to a subject (e.g., immediately after administration, after an initial 24 hours after administration). That is to say, in some embodiments, the devices and devices described herein are configured for release of the biologically active agent (e.g., a therapeutically significant amount of the biologically active agent) for greater than or equal to 24 hours, greater than or equal to 36 hours, greater than or equal to 72 hours, greater than or equal to 96 hours, greater than or equal to 192 hours, greater than or equal to 15 days, greater than or equal to 30 days, greater than or equal to 40 days, greater than or equal to 50 days, greater than or equal to 60 days, greater than or equal to 70 days, greater than or equal to 80 days, greater than or equal to 90 days, greater than or equal to 100 days, greater than or equal to 120 days, greater than or equal to 150 days, greater than or equal to 200 days, greater than or equal to 300 days, greater than or equal to 365 days, or greater than or equal to 600 days after administration to the subject. In some embodiments, the devices and devices described herein are configured for release of the biologically active agent for less than or equal to 1000 days, less than or equal to 600 days, less than or equal to 365 days, less than or equal to 300 days, less than or equal to 200 days, less than or equal to 150 days, less than or equal to 120 days, less than or equal to 100 days, less than or equal to 90 days, less than or equal to 80 days, less than or equal to 70 days, less than or equal to 60 days, less than or equal to 50 days, less than or equal to 40 days, less than or equal to 30 days, less than or equal to 15 days, less than or equal to 192 hours, less than or equal to 96 hours, less than or equal to 72 hours, or less than or equal to 36 hours after administration to the subject. Combinations of the above referenced ranges are also possible.

In some embodiments, between about 0.05 wt % and about 99 wt % of the biologically active agent is released from the device after a certain amount of time. In some embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % and/or less than or equal to about 99 wt %, less than or equal to about 98 wt %, less than or equal to about 95 wt %, less than or equal to about 90 wt %, less than or equal to 75 wt %, less than or equal to about 50 wt %, less than or equal to about 20 wt %, less than or equal to 10 wt %, less than or equal to about 5 wt %, less than or equal to about 1 wt %, less than or equal to about 0.5 wt %, or less than or equal to about 0.1 wt %, of the biologically active agent associated with the device is released from the device after about 24 hours, after about 32 hours, after about 72 hours, after about 96 hours, or after about 192 hours. In some embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % and/or less than or equal to 99 wt %, less than or equal to about 98 wt %, less than or equal to about 95 wt %, less than or equal to about 90 wt %, less than or equal to 75 wt %, less than or equal to about 50 wt %, less than or equal to about 20 wt %, less than or equal to 10 wt %, less than or equal to about 5 wt %, less than or equal to about 1 wt %, less than or equal to about 0.5 wt %, or less than or equal to about 0.1 wt % of the biologically active agent associated with the polymeric component is released from the device (e.g., after about 1 day, after about 3 days, after about 5 days, after about 7 days, after about 15 days, after about 30 days, after about 40 days, after about 50 days, after about 60 days, after about 70 days, after about 80 days, after about 90 days, after about 100 days, after about 120 days, after about 150 days, after about 200 days, after about 300 days, after about 365 days, after about 600 days, or after 1000 days). For example, in some cases, at least about 70 wt % of the biologically active agent associated with the polymeric component is released from the component after about 120 days after an initial 24 hours after administration to a subject. It should be appreciated that where more than one biologically active agent is present (e.g., a first biologically active agent present in the polymeric material forming the bulk of the body portion, or a second biologically active agent in the pores of the body portion), each biologically active agent may independently be released at a rate within one or more ranges described above.

In some embodiments, the biologically active agent is released from the device at a particular initial average rate as determined by the first 24 hours of release (hereinafter, "initial average release rate"). In some embodiments, the biologically active agent is released at an average rate after the first 24 hours of release of at least about 1%, at least about 2%, at least about 5%, least about 10%, at least about 20%, at least about 30%, least about 50%, at least about 75%, at least about 80%, at least about 90%, at least about 95%, or at least about 98% of the initial average release rate. In some embodiments, the biologically active agent is released at an average rate of less than or equal to about 99%, less than or equal to about 98%, less than or equal to about 95%, less than or equal to about 90%, less than or equal to about 80%, less than or equal to about 75%, less than or equal to about 50%, less than or equal to about %, less than or equal to about 30%, less than or equal to about 20%, less than or equal to about 10%, less than or equal to about 5%, or less than or equal to about 2% of the initial average release rate. Combinations of the above referenced ranges are also possible (e.g., between about 1% and about 99%, between about 1% and about 98%, between about 2% and about 95%, between about 10% and about 30%, between about 20% and about 50%, between about 30% and about 80%, between about 50% and about 99%). Other ranges are also possible. It should be appreciated that where more than one biologically active agent is present (e.g., a first biologically active agent present in the polymeric material forming the bulk of the body portion, or a second biologically active agent in the pores of the body portion), each biologically active agent may independently be released at a rate within one or more ranges described above.

The biologically active agent may be released at an average rate over a given 24-hour period after the first 24-hour period of release. The average rate of release may be between about 1% and about 99% of the initial average release rate, as determined between 48 hours and about 1000 days (e.g., between 48 hours and 1 week, between 3 days and 1 month, between 1 week and 1 month, between 1 month and 6 months, between 3 months and 1 year, between 6 months and 2 years) after the initial release. That is to say, in some embodiments, the devices and devices described herein may have a relatively long non-zero release rate of the biologically active agent (e.g., when administered to a subject, after hydration) after the first 24-hour period of release. In an exemplary embodiment, the biologically active agent is configured to be released from the polymeric material at a first average rate as determined at 24 hours of release and at a second average rate of at least about 1% of the first average rate after 30 days.

In some embodiments, the biologically active agent is not released as a burst release from the device. In an illustrative embodiment, in which at least about 0.05 wt % of the biologically active agent is released from the device after about 24 hours, between about 0.05 wt % and about 10 wt % (e.g., at least about 0.05 wt %, at least about 0.1 wt %, at least about 0.5 wt %, at least about 1 wt %, or at least about 5 wt %) is released during the first day of release, and between about 0.05 wt % and about 10 wt % is released during the second day of release. Those skilled in the art would understand that the biologically active agent may be further released in similar amounts during a third day, a fourth day, a fifth day, etc. depending on the properties of the device and/or the biologically active agent.

In some embodiments, at least a portion of the biologically active agent is released in a burst release (e.g., a single burse release, two or more burst releases, a plurality of burst releases). For example, in an illustrative embodiment, greater than or equal to 0.05 wt %, greater than or equal to 0.1 wt %, greater than or equal to 0.5 wt %, greater than or equal to 1 wt %, greater than or equal to 2 wt %, greater than or equal to 5 wt %, greater than or equal to 10 wt %, greater than or equal to 15 wt %, greater than or equal to 20 wt %, greater than or equal to 25 wt %, greater than or equal to 30 wt %, greater than or equal to 40 wt %, greater than or equal to 50 wt %, greater than or equal to 60 wt %, greater than or equal to 70 wt %, greater than or equal to 80 wt %, greater than or equal to 90 wt %, greater than or equal to 95 wt %, greater than or equal to 98 wt %, greater than or equal to 99 wt %, greater than or equal to 99.5 wt %, or greater than or equal to 99.8 wt % of the biologically active agent is released in a burst release versus the total weight percent of the biologically active agent present in the device. In some embodiments, less than or equal to 100 wt %, less than or equal to 99.9 wt %, less than or equal to 99.8 wt %, less than or equal to 99.5 wt %, less than or equal to 99 wt %, less than or equal to 98 wt %, less than or equal to 95 wt %, less than or equal to 90 wt %, less than or equal to 80 wt %, less than or equal to 70 wt %, less than or equal to 60 wt %, less than or equal to 50 wt %, less than or equal to 40 wt %, less than or equal to 30 wt %, less than or equal to 25 wt %, less than or equal to 20 wt %, less than or equal to 15 wt %, less than or equal to 10 wt %, less than or equal to 5 wt %, less than or equal to 2 wt %, less than or equal to 1 wt %, less than or equal to 0.5 wt %, or less than or equal to 0.1 wt % of the biologically active agent is released in a burst release. Combinations of the above referenced ranges are also possible (e.g., greater than or equal to 0.05 wt % and less than or equal to 100 wt %, greater than or equal to 0.1 wt % and less than or equal to 50 wt %, greater than or equal to 10 wt % and less than or equal to 90 wt %, greater than or equal to 40 wt % and less than or equal to 100 wt %). Other ranges are also possible.

In some embodiments, at least a portion of the biologically active agent is released in a single burst release from the device in one or more of the ranges listed above. In some embodiments, at least a portion of the biologically active agent is released in two or more (e.g., three or more, four or more, five or more, six or more) burst releases from the device, each release in one or more of the ranges listed above relative to the amount of biologically active agent present in the device after initial loading or relative to the amount of the biologically active agent present in the device after the previous burst release. Each burst release may be separated by any suitable amount of time including, for example, greater than or equal to 0.1 seconds, greater than or equal to 1 second, greater than or equal to 5 seconds, greater than or equal to 10 seconds, greater than or equal to 30 seconds, greater than or equal to 1 minute, greater than or equal to 5 minutes, greater than or equal to 30 minutes, greater than or equal to 1 hour, greater than or equal to 4 hours, greater than or equal to 12 hours, greater than or equal to 24 hours, greater than or equal to 3 days, greater than or equal to 1 week, greater than or equal to 1 month, or greater than or equal to 1 year. In some embodiments, each burst release is separated by less than or equal to 2 years, less than or equal to 1 year, less than or equal to 1 month, less than or equal to 1 week, less than or equal to 3 days, less than or equal to 24 hours, less than or equal to 12 hours, less than or equal to 4 hours, less than or equal to 1 hour, less than or equal to 30 minutes, less than or equal to 5 minutes, less than or equal to 1 minute, less than or equal to 30 seconds, less than or equal to 10 seconds, less than or equal to 5 seconds, or less than or equal to 1 second. Combinations of the above-referenced ranges are also possible (e.g., greater than or equal to 0.1 seconds and less than or equal to 1 year). Other ranges are also possible.

The term burst release as used herein is given its ordinary meaning in the art and generally refers to a substantial change in the rate of release of a compound (e.g., a biologically active agent) from a device over a relatively short period of time. In some embodiments, the burst release of a particular weight percent of biologically active agent occurs for less than or equal to 60 seconds, less than or equal to 30 seconds, less than or equal to 15 seconds, less than or equal to 10 seconds, less than or equal to 5 seconds, less than or equal to 2 seconds, less than or equal to 1 second, less than or equal to 0.5 seconds, or less than or equal to 0.1 seconds. In some embodiments, the burst release occurs for greater than or equal to 0.01 seconds, greater than or equal to 0.1 seconds, greater than or equal to 0.5 seconds, greater than or equal to 1 second, greater than or equal to 2 seconds, greater than or equal to 5 seconds, greater than or equal to 10 seconds, greater than or equal to 15 seconds, or greater than or equal to 30 seconds. Combinations of the above-referenced ranges are possible (e.g., less than or equal to 60 seconds and greater than or equal to 0.01 seconds). Other ranges are also possible.

In some embodiments, the device may be configured to release one or more biologically active agent(s) using a combination of burst release(s) and controlled release(s). In an illustrative example, a biologically active agent may be released by a first burst release followed by a controlled release in any of the amounts, average rates, and/or time periods described above. In another illustrative example, a first biologically active agent may be released by a burst release and a second biologically active agent may be released at a particular average rate as described above. In some embodiments, the first biologically active agent and the second biologically active agent may begin release at substantially the same time. In some embodiments, the first biologically active agent and the second biologically active agent may be released at different times.

The biologically active agent(s) may be released at a substantially constant average rate (e.g., a substantially zero-order average release rate) over a time period of at least about 24 hours. In some embodiments, the biologically active agent is released at a first-order release rate (e.g., the rate of release of the biologically active agent is generally proportional to the concentration of the biologically active agent) of a time period of at least about 24 hours.

In some embodiments, the plurality of pores (e.g., device 12 of FIG. 1B, device 14 of FIG. 1C) or of a first water soluble material, optionally having a second water soluble polymer positioned within at least a portion of said pores) have a particular mean pore size. In some embodiments, the mean pore size of the plurality of pores is less than or equal to 500 nm, less than or equal to 450 nm, less than or equal to 400 nm, less than or equal to 350 nm, less than or equal to 300 nm, less than or equal to 250 nm, less than or equal to 200 nm, less than or equal to 150 nm, less than or equal to 100 nm, less than or equal to 75 nm, less than or equal to 50 nm, less than or equal to 25 nm, less than or equal to 20 nm, or less than or equal to 15 nm. In some embodiments, the plurality of pores have a mean pore size of greater than or equal to 10 nm, greater than or equal to 15 nm, greater than or equal to 20 nm, greater than or equal to 25 nm, greater than or equal to 50 nm, greater than or equal to 75 nm, greater than or equal to 100 nm, greater than or equal to 150 nm, greater than or equal to 200 nm, greater than or equal to 250 nm, greater than or equal to 300 nm, greater than or equal to 350 nm, greater than or equal to 400 nm, or greater than or equal to 450 nm. Combinations of the above referenced ranges are also possible (e.g., less than or equal to 500 nm and greater than or equal to 10 nm). Other ranges are also possible. Mean pore size, as described herein, may be determined by mercury intrusion porosimetry of the material in a first configuration (e.g., a water content less than the equilibrium water content state, such as the dehydrated state).

In some embodiments, at least a portion of the plurality of pores may be characterized as nanopores, e.g., pores having an average cross-sectional dimension of less than 1 micron. In some embodiments, at least a portion of the plurality of pores may be characterized as micropores, e.g., pores having an average cross-sectional dimension of less than 1 mm and greater than or equal to 1 micron. In some embodiments, at least 50% (e.g., at least 60%, at least 70%, at least 80%, at least 90%, at least 95%, at least 98%, at least 99%, at least 99.9%) of the plurality of pores have a diameter that is less than or equal to 1 micron, less than or equal to 800 nm, less than or equal to 600 nm, less than or equal to 500 nm, less than or equal to 450 nm, less than or equal to 400 nm, less than or equal to 350 nm, less than or equal to 300 nm, less than or equal to 250 nm, less than or equal to 200 nm, less than or equal to 150 nm, less than or equal to 100 nm, less than or equal to 75 nm, less than or equal to 50 nm, less than or equal to 25 nm, less than or equal to 20 nm, or less than or equal to 15 nm. In some cases, at least 50% of the plurality of pores have a diameter that is greater than or equal to 10 nm, greater than or equal to 15 nm, greater than or equal to 20 nm, greater than or equal to 25 nm, greater than or equal to 50 nm, greater than or equal to 75 nm, greater than or equal to 100 nm, greater than or equal to 150 nm, greater than or equal to 200 nm, greater than or equal to 250 nm, greater than or equal to 300 nm, greater than or equal to 350 nm, greater than or equal to 400 nm, greater than or equal to 450 nm, greater than or equal to 500 nm, greater than or equal to 600 nm, or greater than or equal to 800 nm. Combinations of the above referenced ranges are also possible (e.g., less than or equal to 1000 nm and greater than or equal to 10 nm). Other ranges are also possible.

The compositions and devices (e.g., device 10 of FIG. 1A, device 12 of FIG. 1B, device 14 of FIG. 1C) described herein may have a particular porosity e.g., in a first configuration (e.g., a water content less than the equilibrium water content state, such as the dehydrated state). In some embodiments, the device (or polymeric material) has a porosity of greater than or equal to 5%, greater than or equal to 10%, greater than or equal to 15%, greater than or equal to 20%, greater than or equal to 25%, greater than or equal to 30%, greater than or equal to 35%, greater than or equal to 40%, or greater than or equal to 45% in a first configuration (e.g., a water content less than the equilibrium water content state, such as the dehydrated state). In some embodiments, the device (or polymeric material) has a porosity of less than or equal to 50%, less than or equal to 45%, less than or equal to 40%, less than or equal to 35%, less than or equal to 30%, less than or equal to 25%, less than or equal to 20%, less than or equal to 15%, or less than or equal to 10% in a first configuration (e.g., a water content less than the equilibrium water content state, such as the dehydrated state). Combinations of the above-referenced ranges are also possible (e.g., greater than or equal to 5% and less than or equal to 50% in a first configuration (e.g., a water content less than the equilibrium water content state, such as the dehydrated state)). Other ranges are also possible.

As described herein, in some embodiments, the device, method, catheter, or kit (or polymeric material) described herein is substantially non-thrombogenic. Non-thrombogenicity may be determined as described in Example 1.

In some embodiments, the device (e.g., device 10 of FIG. 1A, device 12 of FIG. 1B, device 14 of FIG. 1C) (or body portion (e.g., body portion 20 of FIGS. 1A-1B)) is hydrophilic. The term "hydrophilic" as used herein is given its ordinary meaning in the art and refers to a material surface having a water contact angle as determined by goniometry of less than 90 degrees. In some embodiments, the polymeric material (or a surface thereof) (e.g., of the device) has a water contact angle of less than or equal to 45 degrees, less than or equal to 40 degrees, less than or equal to 35 degrees, less than or equal to 30 degrees, less than or equal to 25 degrees, less than or equal to 20 degrees, less than or equal to 15 degrees, less than or equal to 10 degrees, less than or equal to 5 degrees, or less than or equal to 2 degrees at an equilibrium water content state. In some embodiments, the polymeric material (or a surface thereof) has a water contact angle of greater than or equal to 1 degree, greater than or equal to 2 degrees, greater than or equal to 5 degrees, greater than or equal to 10 degrees, greater than or equal to 15 degrees, greater than or equal to 20 degrees, greater than or equal to 25 degrees, greater than or equal to 30 degrees, greater than or equal to 35 degrees, or greater than or equal to 40 degrees at an equilibrium water content state. Combinations of the above-referenced ranges are also possible (e.g., greater than or equal to 1 degree and less than or equal to 45 degrees). Other ranges are also possible.

Equilibrium water content state, as used herein, refers the steady state of a device (or material) which does not gain (e.g., absorb) or lose bulk water content as determined when submerged in water at 25° C. without externally applied mechanical stresses. Those skilled in the art would understand that steady state (or equilibrium water content state) shall be understood to not require absolute conformance to a strict thermodynamic definition of such term, but, rather, shall be understood to indicate conformance to the thermodynamic definition of such term to the extent possible for the subject matter so characterized as would be understood by one skilled in the art most closely related to such subject matter (e.g., accounting for factors such as passive diffusion and/or Brownian motion).

In some embodiments, the equilibrium water content state of the device (or polymeric material) is greater than or equal to 10 w/w %, greater than or equal to 20 w/w %, greater than or equal to 25 w/w %, greater than or equal to 30 w/w %, greater than or equal to 35 w/w %, greater than or equal to 40 w/w %, greater than or equal to 45 w/w %, greater than or equal to 50 w/w %, greater than or equal to 55 w/w %, greater than or equal to 60 w/w %, greater than or equal to 65 w/w %, or greater than or equal to 70 w/w %. In some embodiments, the equilibrium water content state of the device (or polymeric material) is less than or equal to 80 w/w %, less than or equal to 75 w/w %, less than or equal to 70 w/w %, less than or equal to 65 w/w %, less than or equal to 60 w/w %, less than or equal to 55 w/w %, less than or equal to 50 w/w %, less than or equal to 45 w/w %, less than or equal to 40 w/w %, less than or equal to 35 w/w %, less than or equal to 30 w/w %, less than or equal to 25 w/w %, or less than or equal to 20 w/w %. Combinations of these ranges are also possible (e.g., greater than or equal to 10 w/w % and less than or equal to 80 w/w %). Other ranges are also possible.

In some embodiments, the device (e.g., device 10 of FIG. 1A, device 12 of FIG. 1B, device 14 of FIG. 1C) is substantially lubricious at an equilibrium water content state. For example, in some embodiments, the device (or polymeric material of the device) has a surface roughness of less than or equal to 1000 nm (Ra) at an equilibrium water content state. In some embodiments, the device (or polymeric material of the device) has a surface roughness (Ra) of less than or equal to 500 nm, less than or equal to 400 nm, less than or equal to 300 nm, less than or equal to 250 nm, less than or equal to 200 nm, less than or equal to 150 nm, less than or equal to 100 nm, less than or equal to 50 nm, less than or equal to 25 nm, less than or equal to 10 nm, or less than or equal to 5 nm at an equilibrium water content state. In some embodiments, the device (or polymeric material of the device) has a surface roughness (Ra) of greater than or equal to 5 nm at an equilibrium water content state, greater than or equal to 10 nm, greater than or equal to 25 nm, greater than or equal to 50 nm, greater than or equal to 100 nm, greater than or equal to 150 nm, greater than or equal to 200 nm, greater than or equal to 250 nm, greater than or equal to 300 nm, greater than or equal to 400 nm, or greater than or equal to 500 nm at an equilibrium water content state. Combinations of the above-referenced ranges are also possible (e.g., greater than or equal to 5 nm and less than or equal to 1000 nm). Other ranges are also possible.

In some embodiments, the device (e.g., device 10 of FIG. 1A, device 12 of FIG. 1B, device 14 of FIG. 1C) has a surface having a coefficient of friction of less than or equal to 0.10 at an equilibrium water content state. For example, the coefficient of friction of a surface of the device (or polymeric material of the device) is less than or equal to 0.1, less than or equal to 0.09, less than or equal to 0.08, less than or equal to 0.07, less than or equal to 0.06, less than or equal to 0.05, less than or equal to 0.04, less than or equal to 0.03, or less than or equal to 0.02. In some embodiments, the coefficient of friction of the surface of the device (or polymeric material of the device) is greater than or equal to 0.01, greater than or equal to 0.02, greater than or equal to 0.03, greater than or equal to 0.04, greater than or equal to 0.05, greater than or equal to 0.06, greater than or equal to 0.07, greater than or equal to 0.08, or greater than or equal to 0.09. Combinations of the above-referenced ranges are also possible (e.g., less than or equal to 0.1 and greater than or equal to 0.01). Other ranges are also possible.

Advantageously, the compositions, devices, and devices described herein may have low sorption of substances such as therapeutic agents (and/or e.g., proteins) in the presence of a dynamic fluid comprising such substances. Such devices and compositions may be useful for use in subjects where, for example, the presence of the device should not substantially decrease the availability and/or concentration of therapeutic agents delivered to the subject (e.g., via the device). In some embodiments, administration of therapeutic agents via a fluid flowed within the devices described herein do not substantially reduce the concentration of the therapeutic agent within the fluid. In some cases, the device may not absorb and/or adsorb the therapeutic agent, e.g., during flow or use.

In some embodiments, less than or equal to 0.5 w/w % sorption of a therapeutic agent to the surface and/or bulk of the first water-soluble polymer occurs as determined at equilibrium water content after exposing the polymer to the therapeutic agent and flushing with 5 times the volume of the device with an aqueous solution, such as water or normal saline. In some embodiments, less than or equal to 0.5 w/w %, less than or equal to 0.4 w/w %, less than or equal to 0.3 w/w %, less than or equal to 0.2 w/w %, or less than or equal to 0.1 w/w % sorption of the therapeutic agent to the surface and/or bulk of the first water-soluble polymer occurs. In some embodiments, greater than or equal to 0.05 w/w %, greater than or equal to 0.1 w/w %, greater than or equal to 0.2 w/w %, greater than or equal to 0.3 w/w %, or greater than or equal to 0.4 w/w % sorption of the therapeutic agent to the surface and/or bulk of the first water-soluble polymer occurs. Combinations of the above-referenced ranges are also possible (e.g., less than or equal to 0.5 w/w % and greater than or equal to 0.05 w/w %). Other ranges are also possible.

Advantageously, the devices and compositions described herein may have desirable swelling characteristics (e.g., in water, in saline, in a fluidic environment of a subject).

In some embodiments, the devices (or polymeric materials) described herein have a first configuration (e.g., a water content less than the equilibrium water content state, such as the dehydrated state) with a water content of less than or equal to 40 w/w %, less than or equal to 30 w/w %, less than or equal to 20 w/w %, less than or equal to 10 w/w %, less than or equal to 5 w/w %, less than or equal to 4 w/w %, less than or equal to 3 w/w %, less than or equal to 2 w/w %, less than or equal to 1 w/w %, less than or equal to 0.8 w/w %, less than or equal to 0.6 w/w %, less than or equal to 0.4 w/w %, or less than or equal to 0.2 w/w %. In some embodiments, the devices (or polymeric materials) described herein have a first configuration (e.g., a water content less than the equilibrium water content state, such as the dehydrated state) with a water content of greater than or equal to 0.1 w/w %, greater than or equal to 0.2 w/w %, greater than or equal to 0.4 w/w %, greater than or equal to 0.6 w/w %, greater than or equal to 0.8 w/w %, greater than or equal to 1 w/w %, greater than or equal to 2 w/w %, greater than or equal to 3 w/w %, greater than or equal to 4 w/w %, greater than or equal to 5 w/w %, greater than or equal to 6 w/w %, greater than or equal to 7 w/w %, greater than or equal to 8 w/w %, greater than or equal to 9 w/w %, greater than or equal to 10 w/w %, greater than or equal to 15 w/w, greater than or equal to 20 w/w %, greater than or equal to 25 w/w %, greater than or equal to 30 w/w %, or greater than or equal to 35 w/w %. Combinations of the above-referenced ranges are also possible (e.g., greater than or equal to 0.1 w/w % and less than 5 w/w %, greater than or equal to 2 w/w % and less than or equal to 10 w/w %, greater than or equal to 2 w/w % and less than or equal to 40 w/w %, or greater than or equal to 6 w/w % and less than or equal to 40 w/w %). Other ranges are also possible.

In some embodiments, the devices (or polymeric materials) described herein have a first configuration (e.g., a water content less than the equilibrium water content state, such as the dehydrated state). In some embodiments, the devices (or polymeric materials) described herein swell from a first configuration (e.g., a water content less than the equilibrium water content state, such as the dehydrated state) to a second configuration (e.g., the equilibrium water content state) in less than or equal to 60 minutes (e.g., less than or equal to 10 minutes, less than or equal to 5 minutes, less than or equal to 1 minute, or less than or equal to 10 seconds). In some embodiments, the devices (or polymeric materials) described herein swell from a first configuration (e.g., a water content less than the equilibrium water content state, such as the dehydrated state) to a second configuration (e.g., the equilibrium water content state) at 25° C.

In some embodiments, the devices (or polymeric materials) described herein swell in an amount greater than or equal to 2 w/w %, greater than or equal to 3 w/w %, greater than or equal to 4 w/w %, greater than or equal to 5 w/w %, greater than or equal to 10 w/w %, greater than or equal to 15 w/w %, greater than or equal to 20 w/w %, greater than or equal to 25 w/w %, greater than or equal to 30 w/w %, greater than or equal to 35 w/w %, greater than or equal to 40 w/w %, or greater than or equal to 45 w/w %, for example, from a first configuration (e.g., a water content less than the equilibrium water content state, such as the dehydrated state) to a second configuration (e.g., the equilibrium water content state). In some embodiments, the devices (or polymeric materials) described herein swell in an amount less than or equal to 50 w/w %, less than or equal to 45 w/w %, less than or equal to 40 w/w %, less than or equal to 35 w/w %, less than or equal to 30 w/w %, less than or equal to 25 w/w %, less than or equal to 20 w/w %, less than or equal to 15 w/w %, less than or equal to 10 w/w %, less than or equal to 5 w/w %, less than or equal to 4 w/w %, or less than or equal to 3 w/w %, for example, from a first configuration (e.g., a water content less than the equilibrium water content state, such as the dehydrated state) to a second configuration (e.g., the equilibrium water content state). Combinations of these ranges are also possible (e.g., greater than or equal to 5 w/w % and less than or equal to 40 w/w %).

In some embodiments, the devices (e.g., device 10 of FIG. 1A, device 12 of FIG. 1B, device 14 of FIG. 1C) described herein are in a first configuration (e.g., a water content less than the equilibrium water content state, such as the dehydrated state). For example, in some embodiments, the devices (or polymeric materials) described herein have a water content of less than or equal to 40 w/w %, less than or equal to 30 w/w %, less than or equal to 20 w/w %, less than or equal to 10 w/w %, less than or equal to 5 w/w %, less than or equal to 4 w/w %, less than or equal to 3 w/w %, less than or equal to 2 w/w %, less than or equal to 1 w/w %, less than or equal to 0.8 w/w %, less than or equal to 0.6 w/w %, less than or equal to 0.4 w/w %, or less than or equal to 0.2 w/w % in a first configuration (e.g., a water content less than the equilibrium water content state, such as the dehydrated state). In some embodiments, the devices (or polymeric materials) described herein have a water content of greater than or equal to 0.1 w/w %, greater than or equal to 0.2 w/w %, greater than or equal to 0.4 w/w %, greater than or equal to 0.6 w/w %, greater than or equal to 0.8 w/w %, greater than or equal to 1 w/w %, greater than or equal to 2 w/w %, greater than or equal to 3 w/w %, or greater than or equal to 4 w/w %. Combinations of the above-referenced ranges are also possible (e.g., greater than or equal to 0.1 w/w % and less than 5 w/w % or greater than or equal to 2 w/w % and less than or equal to 40 w/w %). Other ranges are also possible. The dehydrated state, as described herein, generally refers to the steady state determined under ambient conditions in which the device (or polymeric material) has no appreciable decrease in water content of less than 5 w/w % over 24 hours. In some embodiments, the devices described herein may comprise a coating or unbound porogen, such as a humectant coating, as described in more detail below.

Advantageously, the devices and compositions described herein may be configured for rapid swelling in the presence of an aqueous solution, such as water and/or saline. In some embodiments, the device (e.g., device 10 of FIG. 1A, device 12 of FIG. 1B, device 14 of FIG. 1C) (or body portion (e.g., body portion 20 of FIGS. 1A-1C) or polymeric material) is configured to swell in an amount greater than or equal to 2 w/w %, greater than or equal to 5 w/w %, greater than or equal to 10 w/w %, greater than or equal to 15 w/w %, greater than or equal to 20 w/w %, greater than or equal to 25 w/w %, greater than or equal to 30 w/w %, greater than or equal to 35 w/w %, greater than or equal to 40 w/w %, or greater than or equal to 45 w/w %, for example, from a first configuration (e.g., a water content less than the equilibrium water content state, such as the dehydrated state) to a second configuration (e.g., equilibrium water content state), e.g., at 25° C., e.g., in a particular amount of time (e.g., less than or equal to 60 minutes, less than or equal to 10 minutes, less than or equal to 5 minutes, less than or equal to 1 minute, or less than or equal to 10 seconds), as described in more detail below. In some embodiments, the device or device (or body portion) is configured to swell in an amount less than or equal to 50 w/w %, less than or equal to 45 w/w %, less than or equal to 40 w/w %, less than or equal to 35 w/w %, less than or equal to 30 w/w %, less than or equal to 25 w/w %, less than or equal to 20 w/w %, less than or equal to 15 w/w %, or less than or equal to 10 w/w %, for example, from a first configuration (e.g., a water content less than the equilibrium water content state, such as the dehydrated state) to a second configuration (e.g., an equilibrium water content state), e.g., at 25° C., e.g., in a particular amount of time (e.g., less than or equal to 60 minutes, less than or equal to 10 minutes, less than or equal to 5 minutes, less than or equal to 1 minute, or less than or equal to 10 seconds) as described in more detail below. Combinations of the above-referenced ranges are also possible (e.g., greater than or equal to 5 w/w % and less than or equal to 50 w/w %). Other ranges are also possible.

In some embodiments, the device (e.g., device 10 of FIG. 1A, device 12 of FIG. 1B, device 14 of FIG. 1C) (or body portion (e.g., body portion 20 of FIGS. 1A-1B)) is configured to swell in an amount greater than or equal to 2 w/w %, greater than or equal to 5 w/w %, for example, from a first configuration (e.g., a water content less than the equilibrium water content state, such as the dehydrated state) to a second configuration (e.g., an equilibrium water content state), in less than or equal to 60 minutes, less than or equal to 50 minutes, less than or equal to 40 minutes, less than or equal to 30 minutes, less than or equal to 20 minutes, less than or equal to 10 minutes, less than or equal to 5 minutes, less than or equal to 2 minutes, less than or equal to 1 minute, less than or equal to 30 seconds, or less than or equal to 10 seconds at 25° C. In some embodiments, the device (or polymeric material) is configured to swell in an amount greater than or equal to 5 w/w %, for example, from a first configuration (e.g., a water content less than the equilibrium water content state, such as the dehydrated state) to a second configuration (e.g., an equilibrium water content state), in greater than or equal to 5 seconds, greater than or equal to 15 seconds, greater than or equal to 1 minute, greater than or equal to 2 minutes, greater than or equal to 5 minutes, greater than or equal to 10 minutes, greater than or equal to 20 minutes, greater than or equal to 30 minutes, greater than or equal to 40 minutes, or greater than or equal to 50 minutes at 25° C. Combinations of the above-referenced ranges are also possible (e.g., less than or equal to 60 minutes and greater than or equal to 1 minute). Other ranges are also possible.

In an exemplary embodiment, the device (e.g., device 10 of FIG. 1A, device 12 of FIG. 1B, device 14 of FIG. 1C) (or body portion (e.g., body portion 20 of FIGS. 1A-1B)) is configured to swell to an equilibrium water content state (e.g., greater than or equal to 5 w/w % or greater than or equal to 20 w/w % and less than or equal to 80 w/w %) in less than or equal to 60 minutes (e.g., less than or equal to 10 minutes, less than or equal to 5 minutes, less than or equal to 1 minute, or less than or equal to 10 seconds) from a first configuration (e.g., a water content less than the equilibrium water content state, such as the dehydrated state) (e.g., less than 5 w/w % or greater than or equal to 2 w/w % and less than or equal to 40 w/w %) in water. In some embodiments, the device (or polymeric material) is configured to swell to an equilibrium water content (e.g., greater than or equal to 5 w/w % or greater than or equal to 20 w/w % and less than or equal to 80 w/w %) in less than or equal to 60 minutes (e.g., less than or equal to 10 minutes, less than or equal to 5 minutes, less than or equal to 1 minute, or less than or equal to 10 seconds) from, for example, a first configuration (e.g., a water content less than the equilibrium water content state, such as the dehydrated state) (e.g., less than 5 w/w %) in standard normal saline. In another exemplary embodiment, the device (or polymeric material) is configured to swell to an equilibrium water content (e.g., greater than or equal to 5 w/w % or greater than or equal to 20 w/w % and less than or equal to 80 w/w %) in less than or equal to 60 minutes (e.g., less than or equal to 10 minutes, less than or equal to 5 minutes, less than or equal to 1 minute, or less than or equal to 10 seconds) from, for example, a first configuration (e.g., a water content less than the equilibrium water content state, such as the dehydrated state) (e.g., less than 5 w/w %) in normal saline.

In some embodiments, the device (e.g., device 10 of FIG. 1A, device 12 of FIG. 1B, device 14 of FIG. 1C) (or body portion (e.g., body portion 20 of FIGS. 1A-1B)) has a particular length in the first configuration (e.g., a water content less than the equilibrium water content state, such as the dehydrated state). In some embodiments, the device (or polymeric material) has an increase in overall length in the equilibrium water content state of greater than or equal to 0.1%, greater than or equal to 0.5%, greater than or equal to 1%, greater than or equal to 2%, greater than or equal to 4%, greater than or equal to 6%, greater than or equal to 8%, greater than or equal to 10%, greater than or equal to 12%, greater than or equal to 14%, greater than or equal to 16%, or greater than or equal to 18% as compared to its length in a first configuration (e.g., a water content less than the equilibrium water content state, such as the dehydrated state). In some cases, the device (or polymeric material) has an increase in overall length in the equilibrium water content state of less than or equal to 20%, less than or equal to 18%, less than or equal to 16%, less than or equal to 14%, less than or equal to 12%, less than or equal to 10%, less than or equal to 8%, less than or equal to 6%, less than or equal to 4%, less than or equal to 2%, less than or equal to 1%, or less than or equal to 0.5% as compared to its length in the first configuration (e.g., a water content less than the equilibrium water content state, such as the dehydrated state). Combinations of the above-referenced ranges are also possible (e.g., greater than or equal to 0.1% and less than or equal to 20%). Other ranges are also possible.

In some embodiments, the device (e.g., device 10 of FIG. 1A, device 12 of FIG. 1B, device 14 of FIG. 1C) (or body portion (e.g., body portion 20 of FIGS. 1A-1B)) has a particular outer maximum cross-sectional dimension, such as an outer diameter of a cylindrical tube, an oval tube, an oblong tube, or square tube. In embodiments where the device comprises multiple lumens, the outer diameter refers to the outer maximum cross-sectional dimension of one or more of the lumens. For example, in some embodiments only one lumen may have the recited outer diameter. In other embodiments, each and every lumen may independently have the recited outer diameter. In some embodiments, the device (or polymeric material) has an increase in an outer maximum cross-sectional dimension (e.g., outer diameter) in the equilibrium water content state of greater than or equal to 0.1%, greater than or equal to 0.5%, greater than or equal to 1%, greater than or equal to 2%, greater than or equal to 4%, greater than or equal to 6%, greater than or equal to 8%, greater than or equal to 10%, greater than or equal to 12%, greater than or equal to 14%, greater than or equal to 16%, or greater than or equal to 18% as compared to the maximum cross-sectional dimension (e.g., outer diameter) in a first configuration (e.g., a water content less than the equilibrium water content state, such as the dehydrated state). In some cases, the device (or polymeric material) has an increase in the maximum cross-sectional dimension (e.g., outer diameter) in the equilibrium water content state of less than or equal to 20%, less than or equal to 18%, less than or equal to 16%, less than or equal to 14%, less than or equal to 12%, less than or equal to 10%, less than or equal to 8%, less than or equal to 6%, less than or equal to 4%, less than or equal to 2%, less than or equal to 1%, or less than or equal to 0.5% as compared to the maximum cross-sectional dimension (e.g., outer diameter) in a first configuration (e.g., a water content less than the equilibrium water content state, such as the dehydrated state). Combinations of the above-referenced ranges are also possible (e.g., greater than or equal to 0.1% and less than or equal to 20%, greater than or equal to 0.1% and less than or equal to 10%). Other ranges are also possible.

In some embodiments, the device (or body portion) has a particular inner diameter (e.g., in an embodiment in which the device comprises a hollow core), which is the maximum inner cross-sectional dimension, such as the inner diameter of a cylindrical tube or square tube (or other non-circular device or body portion). In embodiments where the device (or body portion) comprises multiple lumens, the inner diameter refers to the maximum inner cross-sectional dimension (i.e., the maximum inner cross-sectional dimension of the largest lumen). In some embodiments, the device (or body portion) has an increase in the inner diameter in the equilibrium water content state of greater than or equal to 0.1%, greater than or equal to 0.5%, greater than or equal to 1%, greater than or equal to 2%, greater than or equal to 4%, greater than or equal to 6%, greater than or equal to 8%, greater than or equal to 10%, greater than or equal to 12%, greater than or equal to 14%, greater than or equal to 16%, or greater than or equal to 18% as compared to the inner diameter in a first configuration (e.g., a water content less than the equilibrium water content state, such as the dehydrated state). In some cases, the device (or body portion) has an increase in the inner diameter in the equilibrium water content state of less than or equal to 20%, less than or equal to 18%, less than or equal to 16%, less than or equal to 14%, less than or equal to 12%, less than or equal to 10%, less than or equal to 8%, less than or equal to 6%, less than or equal to 4%, less than or equal to 2%, less than or equal to 1%, or less than or equal to 0.5% as compared to the inner diameter in a first configuration (e.g., a water content less than the equilibrium water content state, such as the dehydrated state). Combinations of the above-referenced ranges are also possible (e.g., greater than or equal to 0.1% and less than or equal to 20%). Other ranges are also possible.

In some embodiments, the device (or body portion) has a larger percentage increase in the overall length than an increase in inner diameter and/or outer diameter when the device (or polymeric material) swells from a first configuration (e.g., a water content less than the equilibrium water content state, such as the dehydrated state) to a second configuration (e.g., the equilibrium water content state). For example, in some embodiments, the overall length may increase by 1-20% (e.g., 5-15%) while the inner diameter and/or outer diameter increases by 0.1-19% (e.g., 1-10%).

In some embodiments, the ratio of the percentage increase in the overall length to the percentage increase in the inner diameter and/or outer diameter when the device (or polymeric material) swells from a first configuration (e.g., a water content less than the equilibrium water content state, such as the dehydrated state) to a second configuration (e.g., the equilibrium water content state) is greater than or equal to 1.1, greater than or equal to 1.5, greater than or equal to 2, greater than or equal to 5, greater than or equal to 7, or greater than or equal to 10. In some embodiments, the ratio of the percentage increase in the overall length to the percentage increase in the inner diameter and/or outer diameter when the device (or polymeric material) swells from a first configuration (e.g., a water content less than the equilibrium water content state, such as the dehydrated state) to a second configuration (e.g., the equilibrium water content state) is less than or equal to 20, less than or equal to 15, less than or equal to 10, less than or equal to 5, or less than or equal to 2. Combinations of these ranges are also possible (e.g., 1.1-20).

Figure 2:
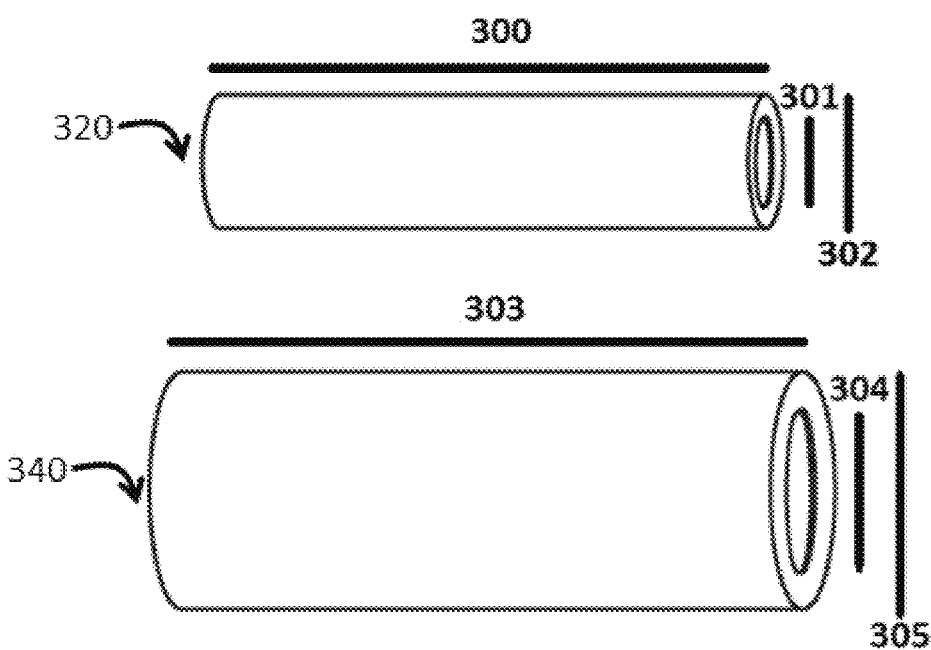
FIG. 2 is a side view of a catheter depicting the change in dimensions before and after swelling, according to one set of embodiments.

In some embodiments, the device (or body portion) has a larger percentage increase in the inner diameter and/or outer diameter than in overall length when the device (or polymeric material) swells from a first configuration (e.g., a water content less than the equilibrium water content state, such as the dehydrated state). As a non-limiting example, in FIG. 2, device 320 swelled from a first configuration (e.g., a water content less than the equilibrium water content state, such as the dehydrated state) to a second configuration (e.g., the equilibrium water content state)—device 340. In accordance with some embodiments, in FIG. 2, outer diameter 302 and inner diameter 301 of device 320 increased to outer diameter 305 and inner diameter 304 in device 340, respectively, while overall length 300 increased to overall length 303. In accordance with some embodiments, in FIG. 2, inner diameter 301 and outer diameter 302 increased by a larger percentage than the increase in overall length 300 when device 320 swelled to the equilibrium water content state—device 340. In some embodiments, the inner diameter and/or outer diameter may increase by 1-20% (e.g., 5-15%) while the overall length increases by 0.1-19% (e.g., 1-10%).

In some embodiments, the ratio of the percentage increase in the inner diameter and/or outer diameter to the percentage increase in the overall length when the device (or polymeric material) swells from a first configuration (e.g., a water content less than the equilibrium water content state, such as the dehydrated state) to a second configuration (e.g., the equilibrium water content state) is greater than or equal to 1.1, greater than or equal to 1.5, greater than or equal to 2, greater than or equal to 5, greater than or equal to 7, or greater than or equal to 10. In some embodiments, the ratio of the percentage increase in the inner diameter and/or outer diameter to the percentage increase in the overall length when the device (or polymeric material) swells from a first configuration (e.g., a water content less than the equilibrium water content state, such as the dehydrated state) to a second configuration (e.g., the equilibrium water content state) is less than or equal to 20, less than or equal to 10, less than or equal to 5, or less than or equal to 2. Combinations of these ranges are also possible (e.g., 1.1-20).

In some embodiments, the device (e.g., device 10 of FIG. 1A, device 12 of FIG. 1B, device 14 of FIG. 1C) (or body portion (e.g., body portion 20 of FIGS. 1A-1B)) comprises a polymeric material having desirable mechanical properties. For example, in some embodiments, the polymeric material has a Young's elastic modulus in the first configuration (e.g., a water content less than the equilibrium water content state, such as the dehydrated state) (e.g., less than 5 w/w % water content) of greater than or equal to 100 MPa, greater than or equal to 250 MPa, greater than or equal to 500 MPa, greater than or equal to 600 MPa, greater than or equal to 750 MPa, greater than or equal to 800 MPa, greater than or equal to 900 MPa, greater than or equal to 1000 MPa, greater than or equal to 1250 MPa, greater than or equal to 1500 MPa, greater than or equal to 1750 MPa, greater than or equal to 2000 MPa, greater than or equal to 2500 MPa, greater than or equal to 3000 MPa, greater than or equal to 3500 MPa, or greater than or equal to 4000 MPa. In some embodiments, the polymeric material has a Young's elastic modulus in the first configuration (e.g., a water content less than the equilibrium water content state, such as the dehydrated state) (e.g., less than 5 w/w % water content) of less than or equal to 5000 MPa, less than or equal to 4000 MPa, less than or equal to 3500 MPa, less than or equal to 3000 MPa, less than or equal to 2500 MPa, less than or equal to 2000 MPa, less than or equal to 1750 MPa, less than or equal to 1500 MPa, less than or equal to 1250 MPa, less than or equal to 1000 MPa, less than or equal to 900 MPa, less than or equal to 800 MPa, less than or equal to 750 MPa, less than or equal to 600 MPa, less than or equal to 500 MPa, or less than or equal to 250 MPa. Combinations of the above-referenced ranges are also possible (e.g., greater than or equal to 100 MPa and less than or equal to 5000 MPa). Other ranges are also possible.

In some embodiments, the polymeric material has a Young's elastic modulus at an equilibrium water content state of less than or equal to 300 MPa, less than or equal to 250 MPa, less than or equal to 200 MPa, less than or equal to 150 MPa, less than or equal to 100 MPa, less than or equal to 75 MPa, less than or equal to 50 MPa, less than or equal to 25 MPa, less than or equal to 20 MPa, or less than or equal to 10 MPa. In some embodiments, the polymeric material has a Young's elastic modulus at an equilibrium water content state of greater than or equal to 5 MPa, greater than or equal to 10 MPa, greater than or equal to 20 MPa, greater than or equal to 25 MPa, greater than or equal to 50 MPa, greater than or equal to 75 MPa, greater than or equal to 100 MPa, greater than or equal to 150 MPa, greater than or equal to 200 MPa, or greater than or equal to 250 MPa. Combinations of the above-referenced ranges are also possible (e.g., less than or equal to 300 MPa and greater than or equal to 5 MPa). Other ranges are also possible.

In some embodiments, the device (e.g., device 10 of FIG. 1A, device 12 of FIG. 1B, device 14 of FIG. 1C) (or body portion (e.g., body portion 20 of FIGS. 1A-1B)) comprises an osmotic agent. For example, in some embodiments, an osmotic agent may be added (e.g., to the pre-polymer) during formation of the device. In some embodiments, the osmotic agent is present in the polymeric material (e.g., after formation of the polymeric material) in an amount greater than or equal to 0.05 w/w %, greater than or equal to 0.1 w/w %, greater than or equal to 0.2 w/w %, greater than or equal to 0.4 w/w %, greater than or equal to 0.6 w/w %, greater than or equal to 0.8 w/w %, greater than or equal to 1 w/w %, greater than or equal to 1.2 w/w %, greater than or equal to 1.4 w/w %, greater than or equal to 1.6 w/w %, or greater than or equal to 1.8 w/w % versus the total device weight in a first configuration (e.g., dehydrated state) and/or second configuration (e.g., equilibrium water content state). In some cases, the osmotic agent may be present in the polymeric material (e.g., after formation of the polymeric material) in an amount of less than or equal to 2 w/w %, less than or equal to 1.8 w/w %, less than or equal to 1.6 w/w %, less than or equal to 1.4 w/w %, less than or equal to 1.2 w/w %, less than or equal to 1 w/w %, less than or equal to 0.8 w/w %, less than or equal to 0.6 w/w %, less than or equal to 0.4 w/w %, less than or equal to 0.2 w/w %, or less than or equal to 0.01 w/w % versus the total device weight in a first configuration (e.g., dehydrated state) and/or second configuration (e.g., equilibrium water content state). Combinations of the above-referenced ranges are also possible (e.g., greater than or equal to 0.05 w/w % and less than or equal to 2 w/w %). Other ranges are also possible.

Non-limiting examples of suitable osmotic agents include phosphates, borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

In some embodiments, the composition (e.g., comprising or formed of a polymeric material) and/or the first water soluble polymer does not comprise covalent crosslinking, as described in more detail below. In other embodiments, however, the composition and/or the first water soluble polymer comprises physical crosslinking (e.g., interpenetrating network, chain entanglement, and/or one or more bonds such as covalent, ionic, and/or hydrogen bonding). In a particular set of embodiments, no covalent crosslinking agents are used to form the polymeric material, the first water soluble polymer of the polymeric material, and/or the second water soluble polymer.

The first water soluble polymer may be present in the device (e.g., device 10 of FIG. 1A, device 12 of FIG. 1B, device 14 of FIG. 1C) (or body portion (e.g., body portion 20 of FIGS. 1A-1B)) in any suitable amount. For example, in some embodiments, the first water soluble polymer is present in the device and/or body portion in an amount of greater than or equal to 20 w/w %, greater than or equal to 25 w/w %, greater than or equal to 30 w/w %, greater than or equal to 35 w/w %, greater than or equal to 40 w/w %, greater than or equal to 45 w/w %, greater than or equal to 50 w/w %, greater than or equal to 55 w/w %, greater than or equal to 60 w/w %, greater than or equal to 65 w/w %, greater than or equal to 70 w/w %, greater than or equal to 75 w/w %, greater than or equal to 80 w/w %, greater than or equal to 85 w/w %, or greater than or equal to 90 w/w % at an equilibrium water content state. In some embodiments, the first water soluble polymer is present in the device and/or body portion in an amount of less than or equal to 95 w/w %, less than or equal to 90 w/w %, less than or equal to 85 w/w %, less than or equal to 80 w/w %, less than or equal to 75 w/w %, less than or equal to 70 w/w %, less than or equal to 65 w/w %, less than or equal to 60 w/w %, less than or equal to 55 w/w %, less than or equal to 50 w/w %, less than or equal to 45 w/w %, less than or equal to 40 w/w %, less than or equal to 35 w/w %, less than or equal to 30 w/w %, or less than or equal to 25 w/w % at an equilibrium water content state. Combinations of the above-referenced ranges are also possible (e.g., greater than or equal to 20 w/w % and less than or equal to 95 w/w %). Other ranges are also possible.

In some embodiments, the first water soluble polymer comprises or is selected from the group consisting of poly (vinyl alcohol), poly(acrylic acid), polyethylene glycol, poly (vinyl pyrrolidone), poly(methacrylic sulfobetaine), poly (acrylic sulfobetaine), poly(methacrylic carboxybetaine), poly(acrylic carboxybetaine), povidone, polyacrylamide, poly(N-(2-hydroxypropyl)methacrylamide), polyoxazolines, polyphosphates, polyphosphazenes, polyvinyl acetate, polypropylene glycol, poly(N-isopropylacrylamide), poly (2-hydroxymethylmethacrylate), and combinations thereof. In an exemplary set of embodiments, the first water soluble polymer is poly(vinyl alcohol).

In some embodiments, the polymeric material comprises a mixture comprising the first water-soluble polymer and another (e.g., a third) water soluble polymer. In some embodiments, the third water soluble polymer comprises or is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl)methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof. The first and other (e.g., third) water soluble polymers may have different chemical compositions.

In some embodiments, the total weight of the first water soluble polymer and another (e.g., a third) water soluble polymer in the device is greater than or equal to 20 w/w %, greater than or equal to 25 w/w %, greater than or equal to 30 w/w %, greater than or equal to 35 w/w %, greater than or equal to 40 w/w %, greater than or equal to 45 w/w %, greater than or equal to 50 w/w %, greater than or equal to 55 w/w %, greater than or equal to 60 w/w %, greater than or equal to 65 w/w %, greater than or equal to 70 w/w %, greater than or equal to 75 w/w %, greater than or equal to 80 w/w %, greater than or equal to 85 w/w %, greater than or equal to 90 w/w %, greater than or equal to 95 w/w %, greater than or equal to 98 w/w %, or greater than or equal to 99 w/w % at an equilibrium water content state. In some embodiments, the total weight of the first water soluble polymer and another (e.g., a third) water soluble polymer in the device in an amount of less than or equal to 100 w/w %, less than or equal to 90 w/w %, less than or equal to 98 w/w %, less than or equal to 95 w/w %, less than or equal to 90 w/w %, less than or equal to 85 w/w %, less than or equal to 80 w/w %, less than or equal to 75 w/w %, less than or equal to 70 w/w %, less than or equal to 65 w/w %, less than or equal to 60 w/w %, less than or equal to 55 w/w %, less than or equal to 50 w/w %, less than or equal to 45 w/w %, less than or equal to 40 w/w %, less than or equal to 35 w/w %, less than or equal to 30 w/w %, or less than or equal to 25 w/w % at an equilibrium water content state. Combinations of the above-referenced ranges are also possible (e.g., greater than or equal to 20 w/w % and less than or equal to 100 w/w %). Other ranges are also possible.

In some embodiments, the ratio of the first water soluble polymer to the third water soluble polymer present in the device is less than or equal to 100:0, less than or equal to 99:1, less than or equal to 95:5, less than or equal to 90:10, less than or equal to 80:20, less than or equal to 70:30, less than or equal to 60:40, or less than or equal to 55:45. In some embodiments, the ratio of the first water soluble polymer to the third water soluble polymer present in the device is greater than or equal to 50:50, greater than or equal to 60:40, greater than or equal to 70:30, greater than or equal to 80:20, greater than or equal to 90:10, greater than or equal to 95:5, or greater than or equal to 99:1. Combinations of the above-referenced ranges are also possible (e.g., less than or equal to 100:0 and greater than or equal to 50:50). Other ranges are also possible.

As described above and herein, in some embodiments, the device (e.g., device 12 of FIG. 1B, device 14 of FIG. 1C) comprises a second water soluble polymer (e.g., second water soluble polymer 40) disposed within at least a portion of the plurality of pores (e.g., plurality of pores 30) of the body portion (e.g., body portion 20 comprising or formed of a polymeric material). In some embodiments, the second water soluble polymer comprises or is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof. In some embodiments, the second water soluble polymer is poly(acrylic acid). The second water soluble polymer may have a different chemical composition from that of the first (e.g., and optionally third) water soluble polymers.

The second water soluble polymer (e.g., second water soluble polymer 40) may be present in the device in any suitable amount. For example, in some embodiments, the second water soluble polymer is present in the device in an amount of greater than or equal to 0.05 w/w %, greater than or equal to 0.1 w/w %, greater or than or equal to 0.2 w/w %, greater than or equal to 0.5 w/w %, greater than or equal to 1.0 w/w %, greater than or equal to 2.0 w/w %, greater than or equal to 3.0 w/w %, greater than or equal to 4.0 w/w %, greater than or equal to 5.0 w/w %, greater than or equal to 10 w/w %, greater than or equal to 20 w/w %, greater than or equal to 30 w/w %, greater than or equal to 40 w/w %, greater than or equal to 50 w/w %, greater than or equal to 60 w/w %, greater than or equal to 70 w/w %, greater than or equal to 80 w/w %, or greater than or equal to 90 w/w % at an equilibrium water content state. In some embodiments, the second water soluble polymer 40 is present in the device in an amount of less than or equal to 95 w/w %, less than or equal to 90 w/w %, less than or equal to 80 w/w %, less than or equal to 70 w/w %, less than or equal to 60 w/w %, less than or equal to 50 w/w %, less than or equal to 40 w/w %, less than or equal to 30 w/w %, less than or equal to 20 w/w %, less than or equal to 10 w/w %, less than or equal to 5.0 w/w %, less than or equal to 4.0 w/w %, less than or equal to 3.0 w/w %, less than or equal to 2.0 w/w %, less than or equal to 1.0 w/w %, less than 0.5 w/w %, less than 0.2 w/w %, or less than 0.1 w/w % at an equilibrium water content state. In some embodiments, 0 w/w % of the second water soluble polymer is present. Combinations of the above-referenced ranges are also possible (e.g., greater than or equal to 0.05 w/w % and less than or equal to 95 w/w %). Other ranges are also possible.

In some embodiments, the water-soluble polymer (e.g., the first water soluble polymer, the second water soluble polymer, the third water soluble polymer) has a particular molecular weight. In some embodiments, the molecular weight of the water soluble polymer (e.g., each, independently, the first water soluble polymer, the second water soluble polymer, or the third water soluble polymer) may be greater than or equal to 40 kDa, greater than or equal to 50 kDa, greater than or equal to 75 kDa, greater than or equal to 100 kDa, greater than or equal to 125 kDa, greater than or equal to 150 kDa, greater than or equal to 175 kDa, greater than or equal to 200 kDa, greater than or equal to 250 kDa, greater than or equal to 300 kDa, greater than or equal to 350 kDa, greater than or equal to 400 kDa, greater than or equal to 450 kDa, greater than or equal to 500 kDa, greater than or equal to 600 kDa, greater than or equal to 700 kDa, greater than or equal to 800 kDa, greater than or equal to 900 kDa, greater than or equal to 1000 kDa, greater than or equal to 1500 kDa, greater than or equal to 2000 kDa, greater than or equal to 3000 kDa, or greater than or equal to 4000 kDa. In some embodiments, the molecular weight of the water soluble polymer (e.g., each, independently, the first water soluble polymer, the second water soluble polymer, or the third water soluble polymer) may be less than or equal to 5000 kDa, less than or equal to 4000 kDa, less than or equal to 3000 kDa, less than or equal to 2000 kDa, less than or equal to 1500 kDa, less than or equal to 1000 kDa, less than or equal to 900 kDa, less than or equal to 800 kDa, less than or equal to 700 kDa, less than or equal to 600 kDa, less than or equal to 500 kDa, less than or equal to 450 kDa, less than or equal to 400 kDa, less than or equal to 350 kDa, less than or equal to 300 kDa, less than or equal to 250 kDa, less than or equal to 200 kDa, less than or equal to 175 kDa, less than or equal to 150 kDa, less than or equal to 125 kDa, less than or equal to 100 kDa, less than or equal to 75 kDa, or less than or equal to 50 kDa. Combinations of the above-referenced ranges are also possible (e.g., a molecular weight of greater than or equal to 40 kDa and less than or equal to 5000 kDa). Other ranges are also possible.

In some embodiments, the devices (e.g., device 10 of FIG. 1A, device 12 of FIG. 1B, device 14 of FIG. 1C) described herein are, or are configured for use with, a medical device such as a catheter, a balloon, a shunt, a wound drain, an infusion port, a drug delivery device, a tube, a contraceptive device, a feminine hygiene device, an endoscope, a graft, a pacemaker, an implantable cardioverter-defibrillator, a cardiac resynchronization device, a cardiovascular device lead, a ventricular assist device, an endotracheal tube, a tracheostomy tube, an implantable sensor, a ventilator pump, and an ophthalmic device. In some embodiments, the catheter is selected from the group consisting of central venous catheters, peripheral central catheters, midline catheters, peripheral catheters, tunneled catheters, dialysis access catheters, urinary catheters, neurological catheters, percutaneous transluminal angioplasty catheters and/or peritoneal catheters. Other suitable uses are described in more detail, below.

These materials can be made as tough, high strength materials having lubricious and biocompatible surfaces. Nanoporous and microporous solids are described herein that have a particularly high Young's modulus and tensile strength. A nanoporous material is a solid that contains interconnected pores of up to 100 nm in diameter. Processes for making hydrogels are also described. Hydrophilic polymers may be used to make these various porous solids so that a hydrophilic solid is obtained. The water content of a nanoporous or a microporous solid can be high, e.g., 50% w/w at EWC. The water content of a hydrogel may be higher, for example, up to 90% w/w in principle. The porous solid materials can be used to make various devices, including medical catheters and implants with significant reductions in adsorption and/or adhesion of biological components to their surfaces. These or other porous materials may be processed to include polymers that are bulk-incorporated into pores of the solid. An embodiment of the material is a porous material comprising water soluble polymers entrapped in pores of the material. Polymers entrapped by this method have been observed to be present in the pores and to remain in the pores after repeated hydration and dehydration. The entrapped polymers provide a surface that is scratch-resistant and effectively permanent, with the incorporated polymer providing desirable properties beyond the outer surface of the material. In aqueous medium, hydrophilic polymers entrapped by this method are hydrated to extend beyond the surface to enhance biocompatibility and lubricity.

Processes for making the material are described in International Patent Application Publication Nos. WO2018/237166 and WO2017/112878, which are hereby incorporated by reference in their entirety. Processes for making the material can include extrusion so that devices with a high aspect ratio may be created. An embodiment of a process for making the materials involves heating a mixture that comprises at least one water soluble polymer and a solvent to a temperature above the melting point of the polymer solution forming the mixture in a solvent-removing environment resulting in a crosslinked matrix and continuing to remove the solvent until the crosslinked matrix is a microporous or a nanoporous solid material. The crosslinking can take place while cooling the mixture and/or in the solvent-removing environment. Further polymers may be incorporated into pores of the material.

Disclosed herein are forming processes, including extrusion, to make a high strength porous solid. Guidance as to processes and parameters to make porous solids are disclosed, as well as the porous solids. Guidance for bulk incorporation of polymers into porous solids is disclosed. Porous solids are disclosed with good properties and the further inclusion of bulk incorporated polymers provides further improvements.

Herein is disclosed a new process that provides for extrusion of high strength materials. Some embodiments of the process provide one or more of: removal of a solvent from a hydrophilic polymer-solvent mixture as the material is extruded, extruding at a cold temperature, extruding into a solvent-removing environment, and further removal of solvent for a period of time after extrusion. Further, an annealing phase and/or a bulk incorporation for further polymers phase may also be included.

Figure 1D:
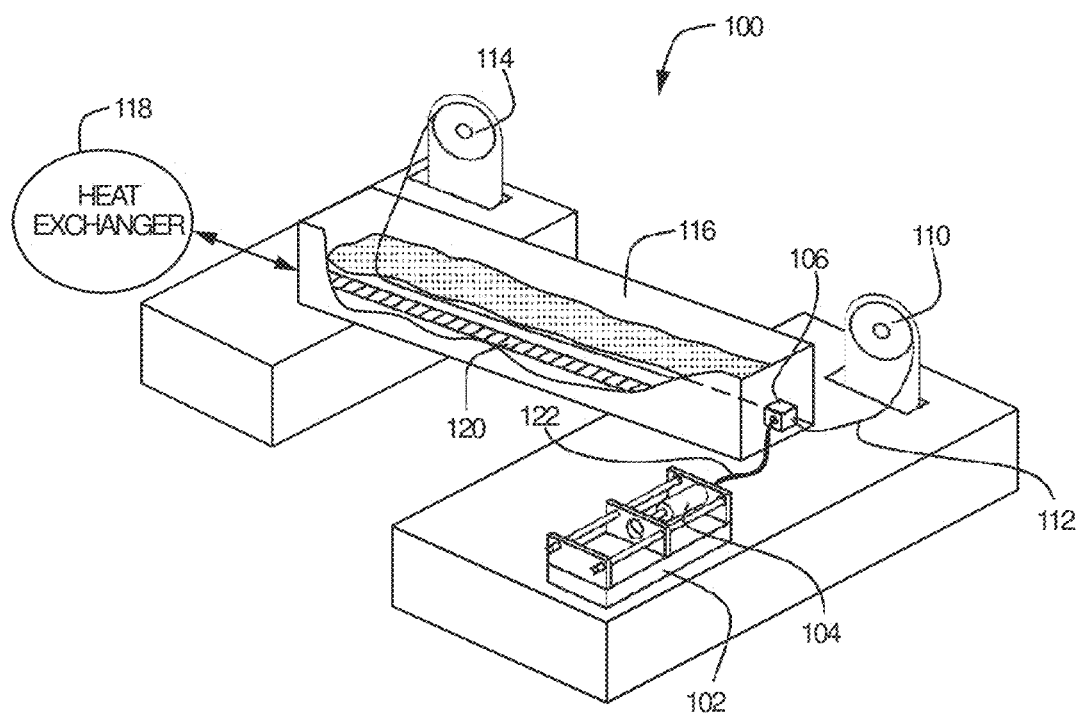
FIG. 1D is a schematic of an exemplary extrusion apparatus to form a continuous form with a cut-away view of a side of the bath, according to one set of embodiments.
Figure 1E:
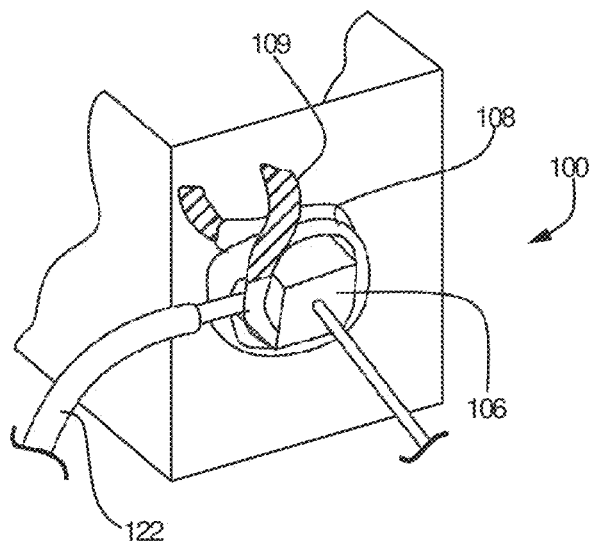
FIG. 1E is an enlarged view of a portion of the apparatus of FIG. 1D depicting the die head in perspective as viewed from the outside of the bath, according to one set of embodiments.
Figure 1F:
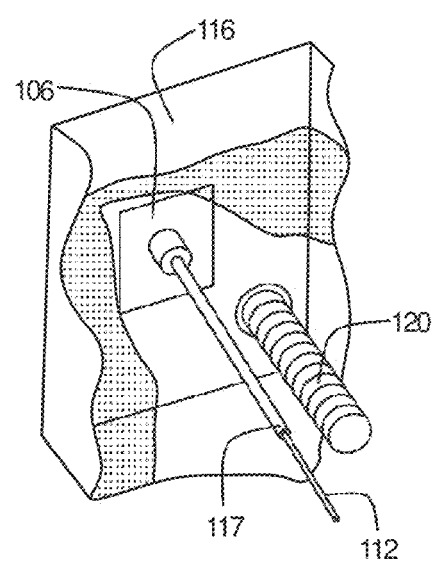
FIG. 1F is an enlarged view of a portion of the apparatus of FIG. 1D depicting the die head as disposed in the bath, according to one set of embodiments.

FIGS. 1D-1F depict an embodiment of an apparatus to make the porous solid materials. A device 100 as depicted includes a syringe pump 102 to accept at least one syringe 104, an optional heating jacket (not shown) to heat the syringes, die head 106, heating element 108 and power cables 109 for the same, providing heating as needed for die head 106 (detail not shown in FIG. 1D), dispensing spool 110 for core tubing 112, uptake spool 114 and motor (not shown) for core tubing, bath 116 for the extruded material 117, with the bath having temperature control for cooling or heating, depicted as heat exchanger 118 that comprises heat exchanging pipe 120 in bath 116. Die head 106 accepts the core tubing 110 which passes therethrough. Feed line 122 from the syringes to die head 106 provides a feed to device 100. A system for this embodiment may further include a weigh station, a jacketed vessel for heating and mixing solutions for loading into the syringes, and a solvent-removal environment for further drying of tubing removed from bath 116. The system may also have a heating station for annealing the tubing or other extrusion product with heat when desired. Core tubing made of PTFE as well as wires, air, gas, non-solvent liquid or other materials may be used for a core.

In use, by way of example, a polymer is heated in a suitable solvent in a jacketed vessel and placed into syringe 104. One or more polymers may be present and a radiopaque agent or other additive may be added. One or more syringes may be used with the same or different mixtures. The syringe(s) of the polymer are heated to a predetermined temperature, e.g., of no more than 80-95° C., and degassed before extrusion. Syringe 104 is mounted on syringe pump 102 with a wrap heater to maintain temperature during extrusion. Core 112 is looped through die head 106, e.g., a heated out-dwelling die head, which feeds into extrusion bath 116, and then attached to an uptake spool 114 that is driven by a motor. The temperature of the bath is controlled using heat exchanger 118, such as a chiller; extruded materials may be extruded at temperatures ranging from −30° C. to 75° C.; other temperatures may be used, and 0° C. is a generally useful temperature setting for extrusion. Artisans will immediately appreciate that all ranges and values between the explicitly stated bounds are contemplated, with, e.g., any of the following being available as an upper or lower limit: −30, −25, −20, −15, −10, −5, 0, 5, 10, 15, 20, 25, 30, 35, 40, 45, 50, 55, 60, 65, 70, 75° C. Uptake (e.g., puller) spool 114 motor speed can be controlled to adjust outer diameter gauge size around core 112. Adjusting die size, material feed rate, tubing core diameter, and puller speed play roles in adjusting final tubing gauge, e.g., in embodiments wherein a catheter is made. Polymer feed rates are adjustable, e.g., by control of syringe pump 102 in this embodiment. Connectors 122 join the one or more syringes to die head 106. Many pumps and other tools for controllably feeding a polymer solution are known. The apparatus and method can be adapted for a drawing process although alternative feed processes are available.

In some embodiments, a composition (e.g., a pre-polymer composition) may be provided (e.g., for extrusion) prior to formation of the polymeric material. In some embodiments, the composition comprises an aqueous solution. The aqueous solution can comprise an osmotic agent at a concentration of greater than or equal to 0.01 M and less than or equal to 8 M. The aqueous solution can comprise a radiopaque agent in an amount of greater than or equal to 0 w/w % and less than or equal to 50 w/w % (e.g., less than or equal to 40 w/w %). The composition can further comprise a water-soluble polymer having a molecular weight of greater than or equal to 40 kDa and less than or equal to 5000 kDa, and present in the solution in an amount greater than or equal to 10 w/w % and less than or equal to 50 w/w %.

In some embodiments, the composition forms a swellable polymeric material upon extrusion.

In some embodiments, the osmotic agent is present in the solution at a concentration of greater than or equal to 0.01 M, greater than or equal to 0.1 M, greater than or equal to 0.5 M, greater than or equal to 1 M, greater than or equal to 2 M, greater than or equal to 3 M, greater than or equal to 4 M, greater than or equal to 5 M, or greater than or equal to 6 M. In some embodiments, the osmotic agent is present in the solution at a concentration of less than or equal to 8 M, less than or equal to 6 M, less than or equal to 4 M, less than or equal to 2 M, less than or equal to 1 M, less than or equal to 0.5 M, or less than or equal to 0.1 M. Combinations of the above-referenced ranges are also possible (e.g., greater than or equal to 0.01 M and less than or equal to 8 M). Osmotic agents are described in more detail herein.

In some embodiments, the radiopaque agent is present in the solution in an amount of greater than or equal to 0 w/w %, greater than or equal to 5 w/w %, greater than or equal to 10 w/w %, greater than or equal to 15 w/w %, greater than or equal to 20 w/w %, greater than or equal to 25 w/w %, greater than or equal to 30 w/w %, greater than or equal to 35 w/w %, greater than or equal to 40 w/w %, or greater than or equal to 45 w/w %. In some embodiments, the radiopaque agent is present in the solution in an amount less than or equal to 50 w/w %, less than or equal to 45 w/w %, less than or equal to 40 w/w %, less than or equal to 35 w/w %, less than or equal to 30 w/w %, less than or equal to 25 w/w %, less than or equal to 20 w/w %, less than or equal to 15 w/w %, less than or equal to 10 w/w %, or less than or equal to 5 w/w %. Combinations of the above-referenced ranges are also possible (e.g., greater than or equal to 0 w/w % and less than or equal to 50 w/w %). Other ranges are also possible. Radiopaque agents are described in more detail, below.

In some embodiments, the water-soluble polymer is present in the solution in an amount greater than or equal to 10 w/w %, greater than or equal to 13 w/w %, greater than or equal to 15 w/w %, greater than or equal to 20 w/w %, greater than or equal to 25 w/w %, greater than or equal to 30 w/w %, greater than or equal to 35 w/w %, greater than or equal to 40 w/w %, or greater than or equal to 45 w/w %. In some embodiments, the water-soluble polymer is present in the solution in an amount less than or equal to 50 w/w %, less than or equal to 45 w/w %, less than or equal to 40 w/w %, less than or equal to 35 w/w %, less than or equal to 30 w/w %, less than or equal to 25 w/w %, less than or equal to 20 w/w %, less than or equal to 15 w/w %, or less than or equal to 13 w/w %. Combinations of the above-referenced ranges are also possible (e.g., greater than or equal to 10 w/w % and less than or equal to 50 w/w %). In some embodiments, the water-soluble polymer is present in the solution in an amount greater than or equal to 13 w/w %.

In some embodiments, the method for forming the polymeric materials and/or devices described herein comprises providing a mixture comprising a first water soluble polymer and an osmotic agent (e.g., a salt) as described above. In some embodiments, the mixture is extruded. In some embodiments, the extruded mixture is extruded on a core material to form the polymeric material disposed on the core material. In some embodiments, the formed polymeric material is exposed to a non-solvent of the polymeric material. In some embodiments, a solution comprising a second water soluble polymer different that the first water soluble polymer and, optionally, an osmotic agent, is introduced to the polymeric material. In some embodiments, the polymeric material (e.g., after introducing the solution to the osmotic agent) is heated. In some embodiments, the solution is flowed against the polymeric material. In some embodiments, the polymeric material may be dried.

In an exemplary set of embodiments, the method for forming the polymeric materials and/or devices described herein comprises providing a mixture comprising a first water soluble polymer and an osmotic agent (e.g., a salt), wherein the first water soluble polymer is present in the mixture in an amount greater than or equal to 10 w/w % (e.g., greater than or equal to 13 w/w % or greater than or equal to 13 w/w % and less than or equal to 50 w/w %)

versus the total weight of the mixture, performing the steps of: extruding the mixture at a temperature greater than or equal to 65° C. (e.g., greater than or equal to 65° C. and less than or equal to 100° C.) at atmospheric pressure, on a core material to form the polymeric material disposed on the core material (e.g., a solid rod or a gas), exposing the polymeric material to a non-solvent of the polymeric material at a temperature less than or equal to 28° C. (e.g., less than or equal to 28° C. and greater than or equal to −20° C.) for greater than or equal to 15 minutes (e.g., greater than or equal to 1 hour and less than or equal to 240 hours), introducing, to the polymeric material, a solution comprising a biologically active agent and/or a second water soluble polymer, different than the first water soluble polymer, and/or an osmotic agent (e.g., a salt), heating the polymeric material and the solution to a temperature of greater than or equal to 25° C. (e.g., greater than or equal to 30° C., or greater than or equal to 30° C. and less than or equal to 65° C.), flowing the solution adjacent the polymeric material, for example, for greater than or equal to 1 hour (e.g., greater than or equal to 1 hour and less than or equal to 48 hours or greater than or equal to 3 hours and less than or equal to 48 hours), and drying the polymeric material. In some embodiments, the biologically active agent is distributed within the polymeric material substantially homogeneously to within less than or equal to 50% of an average loading of the biologically active agent in the polymeric material. In some embodiments, the biologically active agent is distributed within the polymeric material non-homogeneously (i.e., on one or more surfaces of the polymeric material).

In some embodiments, the second water soluble polymer is positioned in at least one pore (or a plurality of pores) of the first water soluble polymer, as described herein.

In some embodiments, the non-solvent comprises alcohol. In some embodiments, the non-solvent is ethanol, methanol, propanol, butanol, pentanol, hexanol, heptanol, octanol, decanol, dodecanol, dimethyl sulfoxide, ethyl acetate, acetates, propionates, ethers, dimethyl formamide, dimethyl acetamide, acetone, acetonitrile, ethylene glycol, propylene glycol, glycerol air, vacuum or combinations thereof. Other non-solvents are also possible (e.g., a solvent having a high solubility to water but a lower solubility to the water-soluble polymer, as compared to the solubility in water).

In some embodiments, the step of extruding the mixture is performed under atmospheric pressure at a temperature of greater than or equal to 65° C., greater than or equal to 70° C., greater than or equal to 75° C., greater than or equal to 80° C., greater than or equal to 85° C., greater than or equal to 90° C., greater than or equal to 95° C., greater than or equal to 100° C., or greater than or equal to 105° C. In some embodiments, the step of extruding the mixture is performed under atmospheric pressure at a temperature of less than or equal to 110° C., less than or equal to 105° C., less than or equal to 100° C., less than or equal to 95° C., less than or equal to 90° C., less than or equal to 85° C., less than or equal to 80° C., less than or equal to 75° C., or less than or equal to 70° C. Combinations of the above-referenced ranges are also possible (e.g., greater than or equal to 65° C. and less than or equal to 110° C.). Other ranges are also possible. Those of ordinary skill in the art would understand, based upon the teachings of this specification, that additional pressures (e.g., greater than atmospheric pressure, less than atmospheric pressure) and/or temperatures are also possible.

In some embodiments, the step of exposing the polymeric material to a non-solvent of the polymeric material is performed at a temperature less than or equal to 28° C., less than or equal to 25° C., less than or equal to 20° C., less than or equal to 15° C., less than or equal to 10° C., less than or equal to 5° C., less than or equal to 0° C., less than or equal to −5° C., less than or equal to −10° C., or less than or equal to −15° C. In some embodiments, the step of exposing the polymeric material to a non-solvent of the polymeric material is performed at a temperature greater than or equal to −20° C., greater than or equal to −15° C., greater than or equal to −10° C., greater than or equal to −5° C., greater than or equal to 0° C., greater than or equal to 5° C., greater than or equal to 10° C., greater than or equal to 15° C., greater than or equal to 20° C., or greater than or equal to 25° C. Combinations of the above-referenced ranges are also possible (e.g., less than or equal to 28° C. and greater than or equal to −20° C.). Other ranges are also possible.

In some embodiments, the step of exposing the polymeric material to the non-solvent of the polymeric material is performed (e.g., at a temperature less than or equal to 28° C. and greater than or equal to −20° C.) for greater than or equal to 1 hour, greater than or equal to 2 hours, greater than or equal to 4 hours, greater than or equal to 6 hours, greater than or equal to 8 hours, greater than or equal to 10 hours, greater than or equal to 15 hours, greater than or equal to 20 hours, greater than or equal to 30 hours, greater than or equal to 40 hours, greater than or equal to 50 hours, greater than or equal to 60 hours, greater than or equal to 80 hours, greater than or equal to 100 hours, greater than or equal to 120 hours, greater than or equal to 140 hours, greater than or equal to 160 hours, greater than or equal to 180 hours, greater than or equal to 200 hours, or greater than or equal to 220 hours. In some embodiments, the step of exposing the polymeric material to the non-solvent of the polymeric material is performed for less than or equal to 240 hours, less than or equal to 220 hours, less than or equal to 200 hours, less than or equal to 180 hours, less than or equal to 160 hours, less than or equal to 140 hours, less than or equal to 120 hours, less than or equal to 100 hours, less than or equal to 80 hours, less than or equal to 60 hours, less than or equal to 50 hours, less than or equal to 40 hours, less than or equal to 30 hours, less than or equal to 20 hours, less than or equal to 15 hours, less than or equal to 10 hours, less than or equal to 8 hours, less than or equal to 6 hours, less than or equal to 4 hours, or less than or equal to 2 hours. Combinations of the above-referenced ranges are also possible (e.g., greater than or equal to 1 hour and less than or equal to 240 hours). Other ranges are also possible.

In some embodiments, the step of introducing to the polymeric material, a solution comprising a second water soluble polymer, different than the first water soluble polymer, and an optional osmotic agent (e.g., a salt) comprises heating the polymeric material and the solution to a temperature of greater than or equal to 25° C., greater than or equal to 30° C., greater than or equal to 35° C., greater than or equal to 40° C., greater than or equal to 45° C., greater than or equal to 50° C., greater than or equal to 55° C., or greater than or equal to 60° C. In some embodiments, the polymeric material and the solution are heated to a temperature less than or equal to 65° C., less than or equal to 60° C., less than or equal to 55° C., less than or equal to 50° C., less than or equal to 45° C., less than or equal to 40° C., less than or equal to 35° C., or less than or equal to 30° C. Combinations of the above-referenced ranges are also possible (e.g., greater than or equal to 25° C. and less than or equal to 65° C.). Other ranges are also possible.

In some cases, the solution may be flowed adjacent (e.g., directly adjacent) the polymeric material for a particular amount of time. In some embodiments, the solution is flowed adjacent the polymeric material for greater than or equal to 3 hours, greater than or equal to 5 hours, greater than or equal to 6 hours, greater than or equal to 8 hours, greater than or equal to 10 hours, greater than or equal to 12 hours, greater than or equal to 16 hours, greater than or equal to 20 hours, greater than or equal to 24 hours, greater than or equal to 28 hours, greater than or equal to 32 hours, greater than or equal to 36 hours, greater than or equal to 40 hours, or greater than or equal to 44 hours. In some embodiments, the solution is flowed adjacent the polymeric material for less than or equal to 48 hours, less than or equal to 44 hours, less than or equal to 40 hours, less than or equal to 36 hours, less than or equal to 32 hours, less than or equal to 28 hours, less than or equal to 24 hours, less than or equal to 20 hours, less than or equal to 16 hours, less than or equal to 12 hours, less than or equal to 10 hours, less than or equal to 8 hours, less than or equal to 6 hours, or less than or equal to 5 hours. Combinations of the above-referenced ranges are also possible (e.g., greater than or equal to 3 hours and less than or equal to 48 hours). Other ranges are also possible. Combinations of the above-referenced temperatures and times are also possible.

In some embodiments, the method comprises annealing the polymeric material to a temperature of greater than or equal to 80° C. (e.g., greater than or equal to 80° C. and less than or equal to 250° C.) for greater than or equal to 60 minutes (e.g., greater than or equal to 60 minutes and less than or equal to 480 minutes). In some embodiments, the polymeric material is annealed at a temperature of greater than or equal to 80° C., greater than or equal to 90° C., greater than or equal to 100° C., greater than or equal to 120° C., greater than or equal to 140° C., greater than or equal to 160° C., greater than or equal to 180° C., greater than or equal to 200° C., greater than or equal to 220° C., or greater than or equal to 240° C. In some embodiments, the polymeric material is annealed at a temperature of less than or equal to 250° C., less than or equal to 240° C., less than or equal to 220° C., less than or equal to 200° C., less than or equal to 180° C., less than or equal to 160° C., less than or equal to 140° C., less than or equal to 120° C., less than or equal to 100° C., or less than or equal to 90° C. Combinations of the above-referenced ranges are also possible (e.g., greater than or equal to 80° C. and less than or equal to 250° C.). Other ranges are also possible.

In some embodiments, the polymeric material is annealed for greater than or equal to 30 minutes, greater than or equal to 60 minutes, greater than or equal to 80 minutes, greater than or equal to 100 minutes, greater than or equal to 120 minutes, greater than or equal to 160 minutes, greater than or equal to 200 minutes, greater than or equal to 240 minutes, greater than or equal to 280 minutes, greater than or equal to 320 minutes, greater than or equal to 360 minutes, greater than or equal to 400 minutes, or greater than or equal to 440 minutes. In some embodiments, the polymeric material is annealed for less than or equal to 480 minutes, less than or equal to 440 minutes, less than or equal to 400 minutes, less than or equal to 360 minutes, less than or equal to 320 minutes, less than or equal to 280 minutes, less than or equal to 240 minutes, less than or equal to 200 minutes, less than or equal to 160 minutes, less than or equal to 120 minutes, less than or equal to 100 minutes, or less than or equal to 80 minutes. Combinations of the above-referenced ranges are also possible (e.g., greater than or equal to 60 minutes and less than or equal to 480 minutes). Other ranges are also possible. Combinations of the above-referenced temperatures and times are also possible.

In some embodiments, the core material may be air, water, a non-solvent liquid, a solid, or a gas. In some cases, the core material may be removed after formation of the polymeric material on the core material. The core material may be physically removed and/or dissolved, in some cases.

In an exemplary embodiment, the method comprises, with a mixture (e.g., a solution as described above and herein) comprising at least one water soluble polymer, a salt, and water, wherein the at least one water soluble polymer is present in the mixture in an amount greater than or equal to 13 w/w % versus the total weight of the mixture, performing the steps of: heating the mixture to a temperature greater than or equal to 65° C., after heating the mixture, cooling the mixture to a temperature at least 20° C. cooler than a melting point of the mixture and mechanically shaping the mixture. In some embodiments, after cooling the mixture, the mixture may be extruded at a temperature greater than or equal to 65° C. on a core material to form the polymeric material disposed on the core material. The method may involve exposing the polymeric material to non-solvent of the polymeric material at a temperature less than or equal to 28° C. for greater than or equal to 4 hours and removing at least a portion of the core material from the polymeric material.

In some embodiments, the step of cooling the mixture comprises cooling to a temperature at least 20° C., at least 25° C., at least 30° C., at least 35° C., at least 40° C., at least 45° C., at least 50° C., at least 60° C., at least 70° C., at least 80° C., or at least 90° C. cooler than a melting point of the mixture. In some embodiments, the step of cooling the mixture comprises cooling to a temperature of less than or equal to 100° C., less than or equal to 90° C., less than or equal to 80° C., less than or equal to 70° C., less than or equal to 60° C., less than or equal to 50° C., less than or equal to 45° C., less than or equal to 40° C., less than or equal to 35° C., less than or equal to 30° C., or less than or equal to 25° C. lower than a melting point of the mixture. Combinations of the above-referenced ranges are also possible (e.g., at least 20° C. and less than or equal to 100° C. lower). Other ranges are also possible. The mixture may be cooled for any suitable amount of time.

In some embodiments, the mixture may be mechanically shaped. In some embodiments, the composition (e.g., prior to extrusion i.e. the mixture) may be mechanically shaped by kneading, rolling, cutting, and combinations thereof.

In some embodiments, the mixture is mixed at a temperature of greater than or equal to 80° C., greater than or equal to 90° C., greater than or equal to 100° C., greater than or equal to 120° C., greater than or equal to 140° C., greater than or equal to 160° C., greater than or equal to 180° C., greater than or equal to 200° C., greater than or equal to 220° C., or greater than or equal to 240° C. In some embodiments, the mixture is mixed at a temperature of less than or equal to 250° C., less than or equal to 240° C., less than or equal to 220° C., less than or equal to 200° C., less than or equal to 180° C., less than or equal to 160° C., less than or equal to 140° C., less than or equal to 120° C., less than or equal to 100° C., or less than or equal to 90° C. Combinations of the above-referenced ranges are also possible (e.g., greater than or equal to 80° C. and less than or equal to 250° C.). Other ranges are also possible.

In some embodiments, the method comprises sorption of a second water-soluble polymer into the polymeric material, as described above and herein.

Figure 1G:
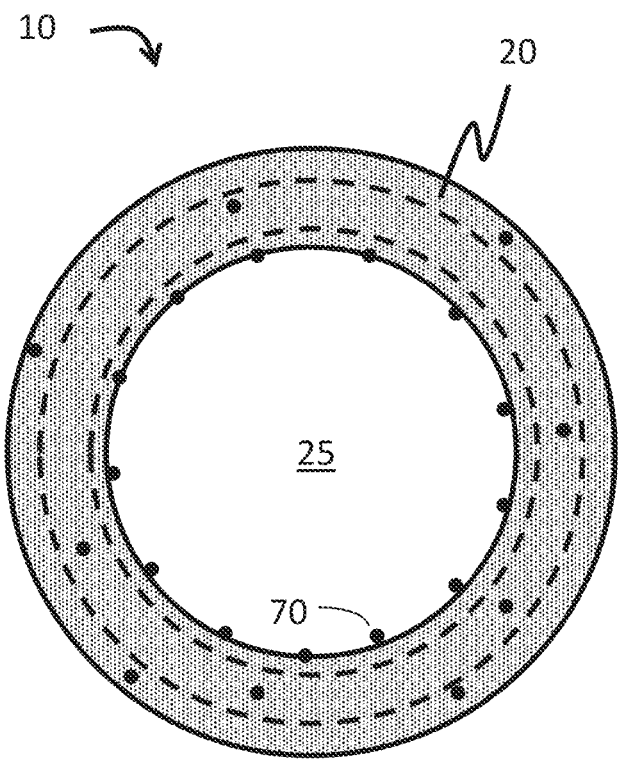
FIG. 1G is a cross-sectional schematic diagram of an exemplary device, according to one set of embodiments.

In some embodiments, the polymeric materials and/or devices described herein may be exposed to and/or comprise a humectant. For example, in some embodiments, device 10 comprises humectant 70, as shown illustratively in FIG. 1G. In some embodiments, at least a portion of the humectant is disposed on a surface (e.g., an inner lumen and/or an abluminal surface) of the polymeric material and/or device (e.g., the body portion). For example, in some embodiments, a portion of humectant 70 is disposed on a surface of device 10. In some embodiments, greater than or equal to 30%, greater than or equal to 40%, greater than or equal to 50%, greater than or equal to 60%, greater than or equal to 70%, greater than or equal to 80%, greater than or equal to 90%, or all of the humectant is disposed on a surface of the polymeric material and/or device (e.g., the body portion). In some embodiments, less than or equal to 100%, less than or equal to 90%, less than or equal to 80%, less than or equal to 70%, less than or equal to 60%, less than or equal to 50%, less than or equal to 40% of the humectant is disposed on a surface of the polymeric material and/or device (e.g., the body portion). Combinations of these ranges are also possible (e.g., 40-100%).

In some embodiments, at least a portion of the humectant is inside the polymeric material and/or device (e.g., the body portion). In some embodiments, at least a portion of the humectant is inside the polymeric material and/or device (e.g., the body portion). For example, in some embodiments, a portion of humectant 70 is inside device 10 (e.g., absorbed into the bulk of the device). In some embodiments, greater than or equal to 30%, greater than or equal to 40%, greater than or equal to 50%, greater than or equal to 60%, greater than or equal to 70%, greater than or equal to 80%, greater than or equal to 90%, or all of the humectant is inside the polymeric material and/or device (e.g., the body portion). In some embodiments, less than or equal to 100%, less than or equal to 90%, less than or equal to 80%, less than or equal to 70%, less than or equal to 60%, less than or equal to 50%, less than or equal to 40% of the humectant is inside the polymeric material and/or device (e.g., the body portion). Combinations of these ranges are also possible (e.g., 30-100%).

In some embodiments, the humectant is a non-ionic surfactant (i.e. a surfactant having an uncharged hydrophilic head and a hydrophobic tail) or a zwitterionic surfactant (i.e. a surfactant having a net uncharged hydrophilic head and a hydrophobic tail). In some embodiments, the humectant is a non-ionic surfactant selected from the group consisting of sugar alcohols, poloxamer, triacetin, α-hydroxy acids, polyethylene glycol, polypropylene glycol, ethylene glycol, propylene glycol, hexylene glycol, butylene glycol, glycerol, sorbitol, mannitol, xylitol, maltitol, erythritol, threitol, arabitol, ribitol, galactitol, fucitol, iditol, inositol, volemitol, malitol, lactitol, maltotriitol, maltotetraitol, polyglycitols, and combinations thereof. In some embodiments, the humectant comprises an oil such as vitamin E. In some embodiments, the humectant comprises a salt such as sodium chloride, potassium chloride, and/or phosphocholine.

Figure 3A:
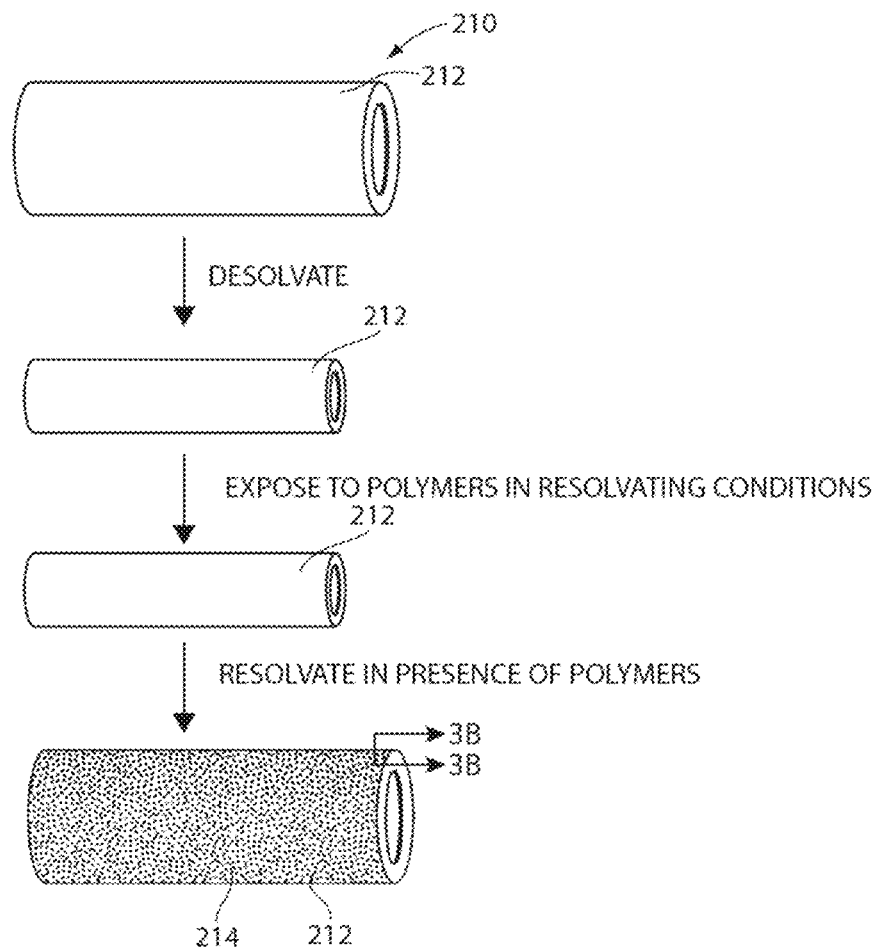
FIG. 3A is a schematic of a process of bulk incorporation of a polymer into a porous solid, according to one set of embodiments.
Figure 3B:
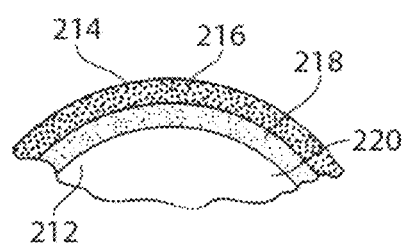
FIG. 3B is a cross-section of a portion of a tube taken along line 3B-3B of FIG. 3A, according to one set of embodiments.

In some embodiments, the polymeric materials and/or devices described herein are exposed to and/or comprise greater than or equal to 0.1 w/w % humectant, greater than or equal to 0.5 w/w % humectant, greater than or equal to 1 w/w % humectant, greater than or equal to 5 w/w % humectant, greater than or equal to 10 w/w % humectant, or greater than or equal to 20 w/w % humectant. In some embodiments, the polymeric materials and/or devices described herein are exposed to and/or comprise less than or equal to 30 w/w % humectant, less than or equal to 25 w/w % humectant, less than or equal to 20 w/w % humectant, less than or equal to 15 w/w % humectant, less than or equal to 10 w/w % humectant, less than or equal to 5 w/w % humectant, or less than or equal to 1 w/w % humectant. Combinations of these ranges are also possible (e.g., 0.1-30 w/w % humectant or 1-10 w/w % humectant). A porous solid (e.g., made by the apparatus of FIGS. 1D-1F) may be annealed. Further, a porous solid, with or without prior annealing, may be processed to further include bulk incorporated polymers. In FIG. 3A, material 210 comprising porous solid matrix 212 is desolvated, exposed to a mixture comprising polymers that are in a resolvating solvent, and resolvated in the mixture to form material 212 with bulk incorporated polymers 214. A cross section of matrix 212 (FIG. 3B) reveals an outermost zone 216 wherein pores of matrix 212 are filled, an intermediate zone 218 wherein there is a lesser density of polymers in the pores, with less filling and/or fewer of the pores being occupied, and an inner zone 220 wherein polymers have not penetrated. The matrix can be solvated and/or desolvated prior to exposure to the mixture, provided that it is desolvated when exposed to the mixture so that water soluble polymers can be moved into the matrix.

In some embodiments, a method for humectifying a device and/or polymeric material comprises placing an extruded segment into a solution comprising the humectant (e.g., glycerol or poloxamer). In some embodiments the solution comprises greater than or equal to 1 w/w %, greater than or equal to 5 w/w %, greater than or equal to 10 w/w %, greater than or equal to 15 w/w %, greater than or equal to 20 w/w %, or greater than or equal to 25 w/w % humectant. In some embodiments, the solution comprises less than or equal to 35 w/w %, less than or equal to 30 w/w %, less than or equal to 25 w/w %, less than or equal to 20 w/w %, less than or equal to 15 w/w %, less than or equal to 10 w/w %, or less than or equal to 5 w/w % humectant. Combinations of these ranges are also possible (e.g., 1-35 w/w %). In some embodiments, the solution comprises a surfactant. In some embodiments, the solution comprises PBS.

In some embodiments, the extruded segment is placed in the solution for a period of time. In some embodiments, the period of time is greater than or equal to 1 hour, greater than or equal to 2 hours, or greater than or equal to 3 hours. In some embodiments, the period of time is less than or equal to 4 hours, less than or equal to 3 hours, or less than or equal to 2 hours. Combinations of these ranges are also possible (e.g., 3 hours, or 1-4 hours).

In some embodiments, the solution is maintained at a temperature during exposure of the extruded segment to the solution. In some embodiments, the temperature is greater than or equal to 20° C., greater than or equal to 30° C., greater than or equal to 37° C., greater than or equal to 40° C., greater than or equal to 50° C., or greater than or equal to 60° C. In some embodiments, the temperature is less than or equal to 70° C., less than or equal to 60° C., less than or equal to 55° C., less than or equal to 50° C., less than or equal to 40° C., less than or equal to 37° C., or less than or equal to 30° C. Combinations of these ranges are also possible (e.g., 20-70° C., 37-55° C., or 45° C.).

In some embodiments, after the extruded segment is removed from the solution, the extruded segment can be dried (e.g., in a convection oven). In some embodiments, the extruded segment is dried at a certain temperature. In some embodiments, the temperature is greater than or equal to greater than or equal to 20° C., greater than or equal to 30° C., or greater than or equal to 40° C. In some embodiments, the temperature is less than or equal to 50° C., less than or equal to 40° C., or less than or equal to 30° C. Combinations of these ranges are also possible (e.g., 30° C., or 20-50° C.). In some embodiments, the extruded segment is dried for a period of time. In some embodiments, the period of time may be greater than or equal to 1 hour, greater than or equal to 2 hours, or greater than or equal to 3 hours. In some embodiments, the period of time may be less than or equal to 4 hours, less than or equal to 3 hours, or less than or equal to 2 hours. Combinations of these ranges are also possible (e.g., 3 hours, or 1-4 hours).

A biologically active agent may be incorporated into the devices and/or devices described herein using any suitable method. For example, in some embodiments, the first water soluble polymer may be mixed with water (e.g., via a solution compounding method at a mass ratio of from 0.1 to 99.9, 1 to 99, from 5 to 95, from 10 to 90, from 20 to 80, from 30 to 70, from 33 to 67, from 37 to 63, from 40 to 60, from 42 to 58, from 45 to 55, from 47 to 53, from 50 to 50 of the water soluble polymer to water). In some embodiments, the biologically active agent may be suspended or solubilized in water prior to solution compounding. The biologically active agent may be micronized, aggregated, and/or untreated, in some cases, when combined into the solution comprising the water-soluble polymer and water. In some embodiments, the biologically active agent may be mixed with the water-soluble polymer and water prior to heating the solution as described herein. In some embodiments, the biologically active agent may be added as the temperature is lowered upon cooling after bulk incorporation of polymers as described herein.

In some embodiments, to solubilize or suspend the active agent in the water, the system may include co-solvents e.g., that have a boiling point higher than the solubilization temperature of the compounding mixture such as N,N-dimethylformamide, suspension agents such as ionic or non-ionic surfactants, oils and castor oil. If the active agent is insoluble, in some cases, the biologically active agent may be micronized and/or made into nanoparticles. The biologically active agent may be mixed, in some cases, into the melt mixture as described herein and e.g., placed under high shear to solubilize.

In some embodiments, the biologically active agent may be incorporated into the body portion via sorption of the biologically active agent. In an exemplary embodiment, the water-soluble polymer material is shaped into near final dimensions through a forming process (e.g., electrospinning, electrospraying, melt spinning, wet spinning, extrusion, molding, casting, coating, and/or non-solvent entrainment). In some embodiments, the water-soluble biologically active agent may then be sprayed, absorbed, or adsorbed into and/or onto the polymer (e.g., PVA) matrix as a solution. The sorption process may occur, in some cases, post-shape forming, post-annealing, post-crosslinking, post-sterilization, or in situ prior to device placement in the subject.

In some embodiments, the biologically active agent may be solubilized into solution with a concentration of less than or equal to 100 w/w %, less than or equal to 90 w/w %, less than or equal to 80 w/w %, less than or equal to 70 w/w %, less than or equal to 60 w/w %, less than or equal to 50 w/w %, less than or equal to 40 w/w %, less than or equal to 30 w/w %, less than or equal to 20 w/w %, less than or equal to 15 w/w %, less than or equal to 10 w/w %, less than or equal to 5 w/w %, less than or equal to 4 w/w %, less than or equal to 3 w/w %, less than or equal to 2 w/w %, less than or equal to 1.5 w/w %, less than or equal to 1 w/w %, less than or equal to 0.5 w/w %, or less than or equal to 0.1 w/w %. In some embodiments, the biologically active agent may be solubilized into solution with a concentration of greater than or equal to 0.01 w/w %, greater than or equal to 0.1 w/w %, greater than or equal to 0.5 w/w %, greater than or equal to 1 w/w %, greater than or equal to 1.5 w/w %, greater than or equal to 2 w/w %, greater than or equal to 3 w/w %, greater than or equal to 4 w/w %, greater than or equal to 5 w/w %, greater than or equal to 6 w/w %, greater than or equal to 7 w/w %, greater than or equal to 8 w/w %, greater than or equal to 9 w/w %, greater than or equal to 10 w/w %, greater than or equal to 15 w/w %, greater than or equal to 20 w/w %, greater than or equal to 30 w/w %, greater than or equal to 40 w/w %, greater than or equal to 50 w/w %, greater than or equal to 60 w/w %, greater than or equal to 70 w/w %, greater than or equal to 80 w/w %, or greater than or equal to 90 w/w %. Combinations of the above-referenced ranges are possible (e.g., less than or equal to 100% and greater than or equal to 0.01%). Other ranges are also possible.

In some embodiments, the biologically active agent may be present in the device (for example, in a first configuration (e.g., a water content less than the equilibrium water content state, such as the dehydrated state)) in an amount of less than or equal to 50 w/w %, less than or equal to 40 w/w %, less than or equal to 30 w/w %, less than or equal to 20 w/w %, less than or equal to 15 w/w %, less than or equal to 10 w/w %, less than or equal to 5 w/w %, less than or equal to 4 w/w %, less than or equal to 3 w/w %, less than or equal to 2 w/w %, less than or equal to 1.5 w/w %, less than or equal to 1 w/w %, less than or equal to 0.5 w/w %, or less than or equal to 0.1 w/w % versus the total weight of the device (for example, in a first configuration (e.g., a water content less than the equilibrium water content state, such as the dehydrated state)). In some embodiments, the biologically active agent may be present in the device (for example, in a first configuration (e.g., a water content less than the equilibrium water content state, such as the dehydrated state)) in an amount of greater than or equal to 0.01 w/w %, greater than or equal to 0.1 w/w %, greater than or equal to 0.5 w/w %, greater than or equal to 1 w/w %, greater than or equal to 1.5 w/w %, greater than or equal to 2 w/w %, greater than or equal to 3 w/w %, greater than or equal to 4 w/w %, greater than or equal to 5 w/w %, greater than or equal to 6 w/w %, greater than or equal to 7 w/w %, greater than or equal to 8 w/w %, greater than or equal to 9 w/w %, greater than or equal to 10 w/w %, greater than or equal to 15 w/w %, greater than or equal to 20 w/w %, greater than or equal to 30 w/w %, or greater than or equal to 40 w/w % versus the total weight of the device (for example, in a first configuration (e.g., a water content less than the equilibrium water content state, such as the dehydrated state)). Combinations of the above-referenced ranges are possible (e.g., less than or equal to 10 w/w % and greater than or equal to 0.01 w/w %, or greater than or equal to 1 w/w % and less than or equal to 5 w/w %). Other ranges are also possible.

In some embodiments, the biologically active agent solution may be further modified to increase solubility (e.g., by modulating pH and/or temperature, by adding an osmotic agent or cosolvent). In some embodiments, hydrolysable bonds (esters and amides) are used to bind active agents or active agent complexes into the polymer material.

In some embodiments, the biologically active agent may be encapsulated. For example, in some embodiments, the biologically active agent may be incorporated into (e.g., mixed) the third water soluble polymer described above and herein.

In an exemplary embodiment, the biologically active agent is added into the compounding mixture during solubilization. Biologically active agent/water soluble polymer mixture may be, in some cases, dehydrated and physically crosslinked e.g., at temperatures above 120° C. Without wishing to be bound by theory, in some embodiments, after cross-linking, the material may be brittle and is micronized, lyophilized, and/or sieved into a powder with a maximum particle size of e.g., 50 microns. In some embodiments, the powder is incorporated into the shape forming process at a mixing or solubilization stage. In some embodiments, the third water-soluble polymer comprises PVA. In some embodiments, the bulk PVA used for the initial encapsulation may contain a PVA with a higher molecular weight than that of the bulk porous PVA (e.g., the first water soluble polymer, the second water soluble polymer). The bulk porous PVA containing the micronized powder may be, in some cases, physically crosslinked e.g., at temperatures over 120° C. Advantageously, and without wishing to be bound by theory, the encapsulation and micronization of the biologically active agent may increase the release rate as compared to the release rate of a biologically active agent without encapsulation or micronization.

In some embodiments, cross-linking of the third water soluble polymer can be achieved by UV-crosslinking, chemical cross-linking (e.g., glutaraldehyde, bis(hydroxyethyl) sulfone, maleic acid, etc.), and/or radiation cross-linking (e.g., gamma) prior to micronization. In some embodiments, traditional encapsulation methods may be used to micronize to less than 50 microns and/or extend a controlled release from a microparticle or nanoparticle e.g., through in situ oil in water emulsion or water in oil emulsion or cavity molding.

In some embodiments, the particles comprising the biologically active agent may be produced in situ with fully polymerized polymer, prepolymer with a crosslinker or initiator, monomer and initiator, or two or more monomers that self-polymerize, or combinations thereof.

As described herein, in some embodiments, the biologically active agent may be present within the plurality of pores of the body portion of the device (e.g., FIGS. 1B-1C). In some such embodiments, the biologically active agent may be released upon e.g., hydration and/or expansion/elongation of the device. Incorporation of the biologically active agent into the plurality of pores may use any suitable method. For example, in some embodiments, the biologically active agent may be mixed with a second water soluble polymer as described herein, such that the second water soluble polymer and biologically active agent are disposed within the plurality of pores. In some embodiments, the biologically active agent may be adsorbed/absorbed into the plurality of pores.

In some embodiments, the biologically active agent may be solubilized and infused into the body portion via a channel of the device (e.g., hollow core 25 of FIGS. 1A-1C). Such devices may be useful as delayed release (e.g., long-term release) and/or reloadable devices.

In some embodiments, a biologically active agent with a water-soluble polymer is co-extruded as a center layer between an outer and inner layer containing a non-agent bulk polymer (e.g., PVA). In an exemplary embodiment, the biologically active agent is compatible with the bulk polymer (with and will adhere well, without delamination. In some embodiments, the biologically active agent layer is distant from the surface allowing for a bindable polymer to be adsorbed and absorbed into those surface layers.

Figure 4A:
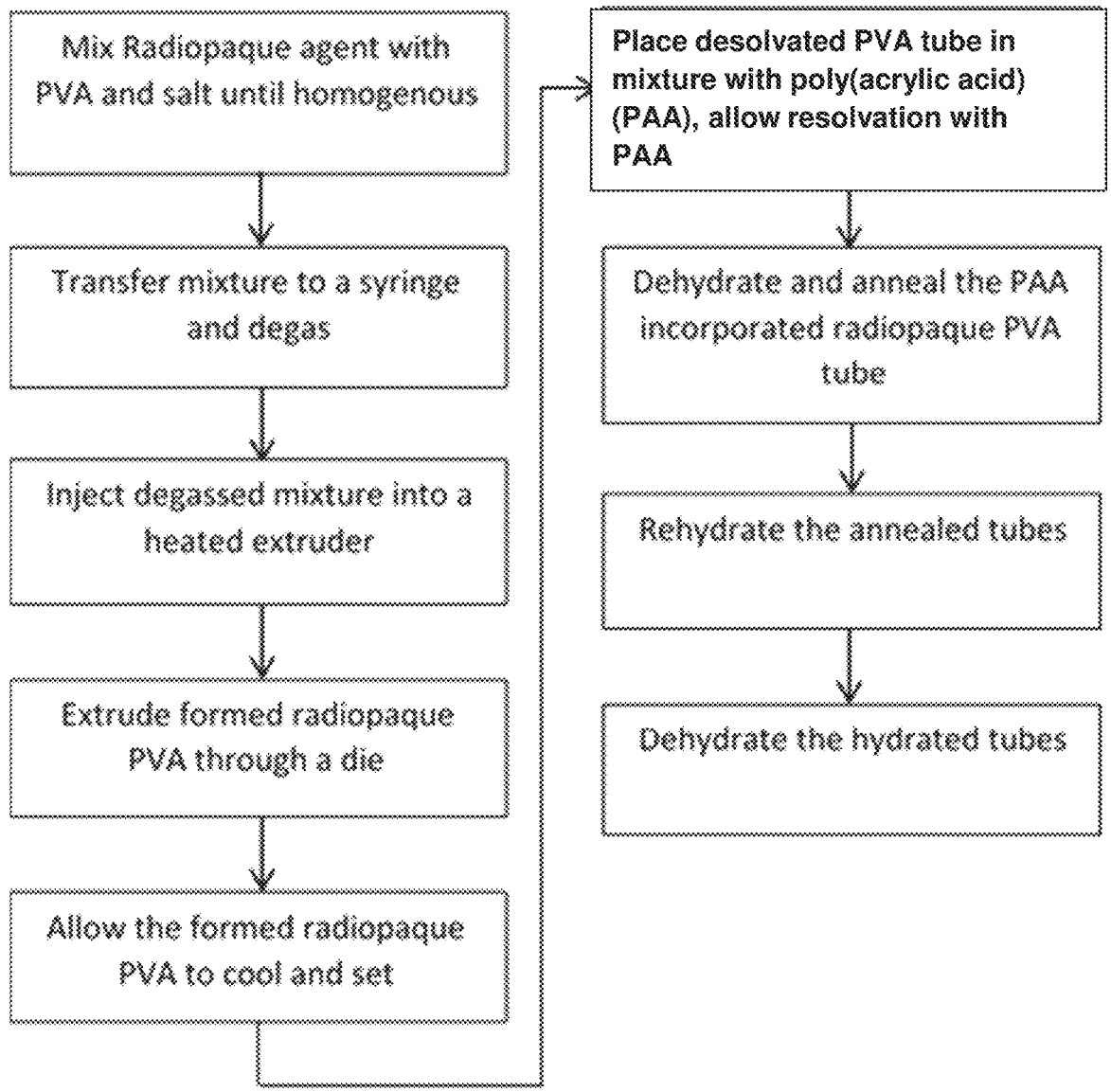
FIG. 4A is a process flow chart for an embodiment of bulk incorporating a surface polymer into a porous solid and includes an extrusion process for making the porous solid, according to one set of embodiments.

In another exemplary embodiment, an agent binding complex can also be added, such as a counterionic system, where an anionic biologically active agent will bind to upon absorption. Without wishing to be bound by theory, upon swelling in an agent-soluble solution, the biologically active agent may migrate into the matrix and bind with a center layer of the device. The outer/inner later may be washed, in some cases, with more rigor than without this center later. In yet another exemplary embodiment, the biologically active agent-containing layer is on one or more surfaces or compatible with drug complex (e.g., allowing for a bindable polymer to be adsorbed and absorbed through the bulk). An exemplary flow chart for a process for making a porous solid including bulk incorporated polymers is presented in FIG. 4A. In this process, a radiopaque (RO) agent is included in an extrusion process. The heated hydrophilic polymer solution refers to the polymers that are bulk incorporated into pores of the extruded porous solid.

Figure 4B:
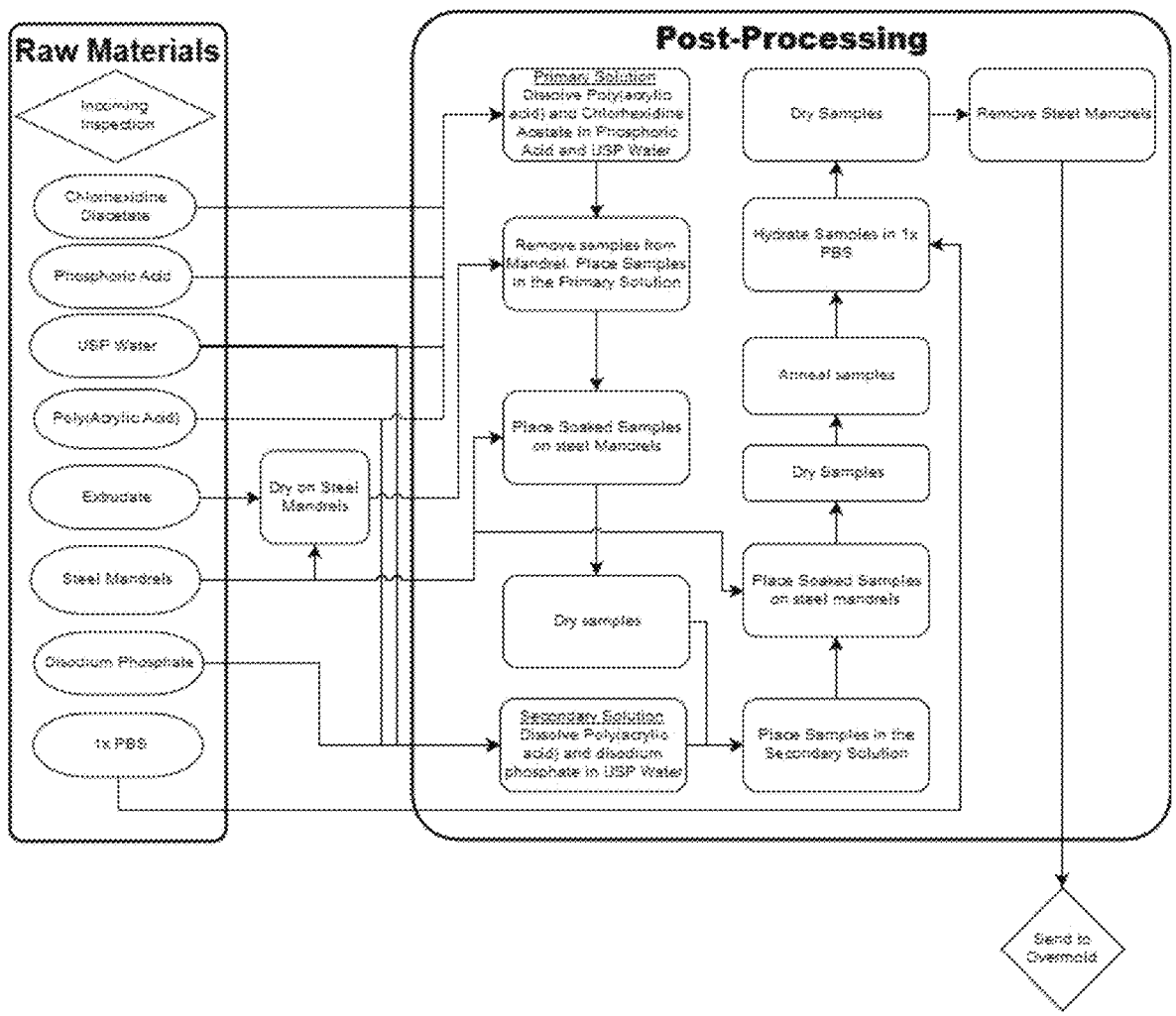
FIG. 4B is a process flow chart for an embodiment of incorporating a biologically active agent and a polymer into a porous solid, according to one set of embodiments.

Another exemplary flow chart for a process for making a porous solid including bulk incorporated polymers and a biologically active agent is shown in FIG. 4B. In this process, post-processing is included in an extrusion process after drying the extrudate on steel mandrels.

Artisans reading this disclosure will be able to adapt its principles in light of what is known about extrusion or other forming arts to make alternative processes and devices that achieve the same end products as described herein. A scaled-up embodiment of this process may be adapted for use with, for example, a multi-zone screw extruder, with the solvent mixture provided via a suitable injector or a hopper and the zones controlled to provide a cold extrusion. Features such as the syringe pump can be replaced by a suitably metered and controlled liquid or solid polymer feed system.

Fukumori et al. (2013), *Open J. Organic Polymer Materials* 3:110-116 reported a freeze-thaw process of making poly(vinyl alcohol) (PVA) materials with a Young's modulus of 181 MPa with a Young's modulus of about 5 MP or more requiring at least about 3 cycles in the samples they tested. The process of making these gels required multiple freeze-thaw cycles. The resultant materials were tested in a dry condition and are not comparable to strengths measured at EWC. Fukumori et al. reported that the crystalline content of the materials increased with the number of freeze-thaw cycles and attributed the strength of the materials to large crystals being formed as the freeze-thaw cycles progressed, with the larger crystals forming superior crosslinks that increased the Tg of the materials. The nature of these processes produces a dried material. Moreover, as discussed below, a freeze-thaw process produces macropores.

In some embodiments, processes herein are free of freeze-thaw processes and/or free of a freezing process and/or free of a thawing process. Further the processes can be used to make solid porous materials that have little or no swelling, e.g., 0%-100% w/w swelling at EWC, even in an absence of covalent crosslinking agents Artisans will immediately appreciate that all ranges and values between the explicitly stated bounds are contemplated, with, e.g., any of the following being available as an upper or lower limit: 0, 5, 10, 15, 20, 25, 30, 40, 50, 60, 70, 80, 90, 95, 100% w/w, with swelling measured as % swelling=100×(Total weight at EWC-dry weight)/dry weight, with the dry weight being the weight of the material without water.

In some embodiments, the extruded samples have a horizontal chain orientation and alignment along the length of samples (in direction of extrusion). A polymeric chain orientation produced by the extrusion process. Without wishing to be bound by theory, it is believed that this horizontal chain orientation and alignment along the length of the samples contributes to the inner diameter and/or outer diameter increasing by a larger percentage than the percentage increase in length when the samples swell, in some embodiments.

In some embodiments, it is useful to have a combination of one or more of: extrusion of a hydrophilic polymer in a solvent; a cold extrusion, and extrusion into a bath that quickly removes solvent from the extrudate. Further, in some embodiments, additional solvent-removing and/or annealing processes provide further utility for making desirable porous solids.

In some embodiments, requirements for a nanoporous material include high polymer concentrations of more than about 10% w/w in the polymer-solvent mixture with high levels of crosslinking. Artisans will immediately appreciate that all ranges and values between the explicitly stated bounds are contemplated, with, e.g., any of the following being available as an upper or lower limit: 10, 12, 15, 16, 17, 18, 19, 20, 25, 30, 35, 40, 45, 50, 55, 60, 70, 80, 90, 95, 99% w/w of the polymer in the total weight of the polymer-solvent mixture. In some embodiments, the polymer is to be substantially solvated, meaning it is a true solution or at least half the polymer is dissolved and the rest is at least suspended. In some embodiments, the solvation of the polymer contributes to the alignment of the polymer chains in an extrusion and to crosslinking among the polymers. Without being bound to a particular theory, it is likely that high concentration of the starting polymer-solvent mixture can help with this. And the probable chain alignment of the material as it passes through a die, according to some embodiments, is thought to promote more intrapolymer versus interpolymer crosslinking. An extrudate or an otherwise formed mixture entering a desolvating environment, whether gas or liquid, is thought to further collapse pore structure before the densely concentrated polymer has completely crosslinked, in some embodiments, thereby improving chain proximity and promoting additional crosslink density. Depositing the extruded or otherwise formed material directly into a solvent removing environment is helpful in some embodiments. In some embodiments, further solvent-removal can be continued to collapse the material until reaching a desired end point in structure and/or properties. An annealing process can further contribute to strength in some embodiments.

Frozen methods, on the other hand, rely on increased strengthening by forcing super-concentrated microregions to also achieve chain proximity and improve crosslink density, but retain a macro porosity due to the presence of ice crystals in the total gel structure. Desolvation creates forced super-concentrated microregions but these do not create macropores. In contrast, a pre-established gel prior to a dehydration or freezing is by nature of that process formed with macropores. Further, the work of the inventors indicates that such nanoporous solids have greater strength than macroporous materials.

Hydrogels can also be made by using a lower polymer concentration in the polymer-solvent mixture, generally less than 10% w/w of polymer in the polymer-solvent mixture. Artisans will immediately appreciate that all ranges and values between the explicitly stated bounds are contemplated, with, e.g., any of the following being available as an upper or lower limit: 2, 5, 7, 8, 9, 10% w/w of the polymer in the total weight of the polymer-solvent mixture. Further, or alternatively, the polymer-solvent mixture is not extruded into a solvent removing environment.

Microporous materials may be made with process conditions intermediate to nanoporous solids and hydrogels. One embodiment is to prepare a material using conditions comparable to making a nanoporous material but to stop solvent removal before solvent removal reaches a nanoporous solid structure.

Extrusion of hydrophilic polymers in a solvent is helpful to make high strength materials. Use of a solvent in an extrusion starting material is, at the least, uncommon. Typically, an extrusion uses a solid material that has been heated to a flowable temperature and then extruded, and later cooled by a variety of methods. For instance, it is believed that thermoplastic extrusion of a pure PVA is possible. But such an extrusion would lack the polymeric structure that is needed to make porous solids and would instead exhibit properties more similar to a conventional thermoplastic material. According to a theory of operation, a pure PVA extrusion would lack the quality of hydrogen bonding that takes place in an aqueous ionic solvent state. A temperature suitable for preparing the PVA to be flowable in an extrusion would create a poorly cohesive material at the die head so that a continuous shape does not form. It was difficult to make extruded PVAs to form high aspect shapes, e.g., tubes, and to use them in an extrusion process. Viscosities of PVA and other hydrophilic polymers are high, and difficult to get into solution. It was observed that a narrow working band of temperature was particularly useful, e.g., 85-95° C. Below about 85° C., PVA failed to truly melt, and thus did not become completely amorphous for extrusion. Above about 95° C., losses to boiling and evaporation made the process ineffective. These temperature ranges could be offset by increasing pressure above atmospheric, but a pressurized system is challenging to use and to scale. The processes are usefully performed at a temperature below a boiling point of the polymer-solvent materials.

The cohesive strength of the flowing polymer-solvent mixture was weak when exiting the die. The use of a core to support the mixture at the die is useful to hold the shape at the die. This condition is in contrast to a typical core extrusion used as a coating process, e.g., for coating wires for a mobile telephone charger. A typical process that avoids use of a solvent or a significant solvent concentration has a relatively higher cohesive strength that it exits the die that is readily capable of holding a tube, and do not relying on active bonding such as the hydrogen bonding in hydrophilic polymers that form the solid material in a coherent shape as it moves out of the die.

Passing the formed polymer-solvent mixture into solvent removal environment was useful. Most extrusions do not use bath temperatures at or below room temperature. Moreover, the use of a solvent removing bath is atypical relative to conventional processes the bath or other solvent removing environment helps solidify the extruded material sufficiently that it remains stable and concentric on the core, otherwise the melt would run into a tear drop shape. It would also be destroyed in the attempt to collect it at the end of the extrusion as it would still be molten. Conventional baths containing water would cause the PVA or similar hydrophilic polymer material to lose shape due to swelling, dissolution, or both. Molding processes that involve preparation of a polymer-solvent mixture that is formed in a mold and then processed into a solvent-removing environment do not have the advantages of alignment of chains observed in an extrusion. However, a suitably controlled temperature and solvent removal can yield materials with a high strength and controlled pore structure.

The porous solids are highly lubricious and can be used in a hydrated state and can be conveniently bonded to other materials. In the case of a catheter, for instance, extensions, luer locks, suture wings, and the like are useful. In some embodiments, copolymer extrusion is useful in ranges of the second polymer from 0.1% to 10% w/w or no more than 10% w/w of the first polymer, with no more than 5% w/w also being useful. Artisans will immediately appreciate that all ranges and values between the explicitly stated bounds are contemplated, with, e.g., any of the following being available as an upper or lower limit: 0.1, 0.2, 0.4, 0.5, 0.8, 1, 2, 3, 4, 5, 6, 8, 10% w/w.

In some embodiments, salts are useful to manipulate the strength of the materials. Without being limited to a particular theory, it is likely the salts are part of the physical crosslinking, in effect acting as small molecular weight crosslinkers between the polymer chains.

Some embodiments for polymer blends include at least one first hydrophilic polymer and at least one second hydrophilic polymer in a solvent that is extruded as described herein. Examples include combinations of one or more of PVA, PAA, PEG, PVP, polyalkylene glycols, a hydrophilic polymer, and combinations thereof. Examples of concentrations include the at least one second hydrophilic polymer being present at 1 part to 10,000 parts of the first hydrophilic polymer. Artisans will immediately appreciate that all ranges and values between the explicitly stated bounds are contemplated, with, e.g., any of the following being available as an upper or lower limit: 1, 2, 10, 100, 1000, 1500, 2000, 2500, 3000, 4000, 5000, 6000, 7000, 8000, 9000, 10000 parts. Examples of concentrations of polymers in a polymer-solvent mixture include a first polymer present at a first concentration and one or more further polymers present at a second concentration, with the first polymer concentration and the further polymer concentration being independently selected from 0.1-99%, e.g., 0.1, 0.2, 0.3, 0.4, 0.5, 0.6, 1, 2, 3, 4, 5, 6, 7, 8, 9, 10, 11, 12, 13, 14, 15, 16, 17, 18, 19, 20, 25, 30, 33, 35, 40, 45, 50 55, 60, 65, 70, 75, 80, 85, 90, 95% w/w. Further, non-hydrophilic polymers and/or non-hydrophilic blocks in block polymers, may be present, with concentrations of such polymers and/or such blocks generally being less than about 10% w/w, e.g., 0.1, 0.2, 1, 2, 3, 4, 5, 6, 7, 8, 9, 10% w/w.

Some embodiments include porous matrices conditioned with water soluble polymers that lose no more than 20-90% w/w of the water-soluble polymer under comparable conditions; Artisans will immediately appreciate that all ranges and values between the explicitly stated bounds are contemplated, e.g., 20, 25, 30, 33, 40, 50, 60, 70, 80, 90% w/w.

In some embodiments, bulk incorporated materials may present a monolayer at the surface. The term monolayer means a layer that is a single molecule thick. The monolayer does not rely on cohesion between the molecules of the monolayer to remain stably present at the surface. At least one water soluble polymer forms the monolayer. In contrast, even a thin polymer coating that is cross-linked to itself has a thickness corresponding to the thickness of the network formed by the cross-linked polymers. For example, it may be possible to create a cross-linked PVA coating on a surface but such a coating relies on interconnections between molecules of the PVA and necessarily forms a crosslinked network. Accordingly, embodiments include a water-soluble polymer present on a surface of a porous solid without covalent bonding to the surface and without the polymer being part of a network.

In some embodiments, the bulk incorporated polymers are durably incorporated. In contrast, a layer of water soluble materials merely adsorbed to an underlying material, e.g., applied by dip coating or spraying, can be essentially removed from a hydrophilic substrate in most or all circumstances meaning at least 90% w/w of the materials can be separated from the underlying material in aqueous solution, e.g., 90° C. for 24 hours in physiological saline. Covalently bonded materials will not be removed under these conditions and some physically crosslinked networks of water-soluble polymers might not be removed but such networks are not preferable compared to a bulk incorporated polymer; for instance, they would likely be more thrombogenic or less durable. Covalent bonding involves use of chemically reactive moieties that can be avoided by bulk incorporation processes.

Processing Systems and Parameters to Make Porous Materials

Processes are provided herein to create biocompatible porous solids such as microporous or nanoporous solid materials that possess low protein adsorption properties and provide a basis for non-biofouling devices. Modification of starting polymer concentration, molecular weight, solvent removal, forming processes, and hardening/annealing processes may be utilized to provide surface properties with reduced protein adsorption and other properties. Some embodiments include creation of various continuous shapes through extrusion of a polymeric mixture. The mixture may be further hardened and annealed. These processes may be used to create a tough and highly lubricious material. Embodiments include polymeric mixtures extruded into shapes possessing single or multiple lumens, of varied diameters and wall thickness.

An embodiment of a process for making a nanoporous solid material comprises heating a mixture that comprises a polymer and a solvent (a polymeric mixture), extruding the mixture into a solvent-removing environment, and removing the solvent from the crosslinked matrix until a nanoporous solid material is formed. One or more of these actions may be combined, depending on the process. Further, cooling the mixture as it passes out of the die is useful. Without being bound to a specific theory of operation, it appears that crosslinking the polymer during passage through the die initially forms a porous matrix that is not a true nanoporous solid material because, although it has spaces between polymer strands, it does not have a pore-structure. As the solvent is removed under appropriate conditions, the crosslinked structure becomes a nanoporous solid. The crosslinking starts when the polymeric mixture is extruded through a die, and as the mixture is cooled. The crosslinking may continue while the solvent is removed. The transition to form the nanoporous material takes place as the solvent is removed and, in general, is believed to be completed or essentially completed (meaning 90% or more) at this stage. The resultant material may be further processed by annealing with or without a presence of further solvents, or plasticizers. This process, and the other extrusion or other formation processes and/or materials set forth herein, including bulk incorporation processes, may be free of one or more of: covalent crosslinking agents, agents that promote covalent crosslinks, radiation that crosslinks polymer chains, freezing, thawing, freeze-thaw cycles, more than one freeze-thaw cycle, ice-crystal formation, foaming agents, surfactants, hydrophobic polymers, hydrophobic polymer segments, reinforcing materials, wires, braids, non-porous solids, and fibers.

The porous materials may be made by an extrusion process that comprises passing a polymeric mixture through a die into a cooling environment. The cooling environment may further be a solvent-removing environment. It is a dehydrating environment when the solvent is water. The die may have a core that passes through it so that the polymeric mixture may be formed around the core. Further solvent-removal environments and/or annealing environments may be used.

The extrusion process for a polymer-solvent mixture may be performed as a cold extrusion. The term cold extrusion refers to a process that involves passing a polymer-solvent mixture through a die and does not require heating the polymer-solvent mixture above its boiling point during the entire process of preparing the polymer-solvent mixture and extruding it. Accordingly, in a cold extrusion, the die head is kept below a boiling point of the polymer-solvent mixture. Although many solvents may be used, water is often a useful solvent in which case the die head is kept at 100° C. or less, although colder temperatures may be useful, as discussed above.

The term polymeric mixture refers to a polymer that is in solution, dissolved, or suspended in a solvent. A solvent may be, e.g., water, aqueous solution, an organic solvent, or combinations thereof. Heating the polymeric mixture may comprise heating the mixture to a temperature above the melting point of the polymer. In general, the solution transitions from a cloudy to a clear state when it reaches the melt point. An aqueous solution contains water, for instance from 10-100% (w/w or v/v) of the liquid being water; Artisans will immediately appreciate that all ranges and values between the explicitly stated bounds are contemplated, e.g., 10, 20, 30, 40, 50 60, 70, 80, or 90% or at least one of the same.

Extrusion is a useful process for forming the materials. Other forming processes may be used, for example, molding, casting, or thermal forming polymer-solvent mixtures. In general, a polymer-solvent mixture is prepared without boiling and formed into a shape that is exposed to solvent-removal conditions that are controlled to make a nanoporous or microporous material using the guidance provided herein. An annealing process may be included. Hydrogels that are not microporous or nanoporous materials can also be made.

The heated polymeric mixture may be molded or otherwise formed as it is cooled or molded/formed and immediately cooled. Formed is a broad term that refers to passing the material from an amorphous melted state into an end-user product or an intermediate shape for further processing. Forming encompasses casting, layering, coating, injection molding, drawing, and extrusion. The forming can be done using an injection molding set up, where the mold consists of a material with thermal conductive properties allowing it to be heated easily to enhance the flow of the injected polymeric mixture, and to be cooled rapidly in a cooling environment. In other embodiments, the molding process can be accomplished by extrusion of the polymeric mixture through a die to form continuous material.

Cooling the polymeric mixture may comprise, e.g., cooling an extruded material, as in the case of passing the polymeric material through a die. An embodiment for cooling is a liquid bath at a temperature at least 20° C. cooler than the polymeric mixture boiling point or alternatively below the polymeric mixture Tm, e.g., 20, 30, 40, 50, 60, 70, 80, 90, 100, 110° C. below the boiling point or polymeric Tm, or alternatively the bath or other environment being at a temperature from −50 to 30° C.; Artisans will immediately appreciate that all ranges and values between the explicitly stated bounds are contemplated, with, e.g., any of the following being available as an upper or lower limit: −50, −45, −25, −20, −10, −5, −4, 0, 15, 20, 25, 30° C. The cooling may be performed in a solvent removing environment. Freezing temperatures may be avoided. Without being bound to a particular theory of operation, the polymer chains are cooled to the point of promoting intermolecular hydrogen binding and immobilizing chain movement. This may occur at temperatures as high as 30° C., or higher if time is allowed. The bath may be aqueous, and, by adjustment with salt or other osmotic agents, may be provided at an osmotic value to perform solvent removal on aqueous materials that are at a relatively lower osmotic value through osmotic pressure and diffusion. The bath may also be other solvents that freeze at temperatures lower than water, so that temperatures below 0° C. may be used without freezing the solvent or materials. In the event that hydrophilic copolymers are used in conjunction with PVA, for instance, temperatures higher than 20° C. may be used as crosslinking and chain immobilization will occur at much higher temperatures.

A solvent-removing environment refers to an environment that significantly accelerates removal of a solvent as compared to drying at ambient conditions. Such an environment may be non-heating, meaning it is not above ambient temperature, e.g., not above 20° C. Such an environment may be a vacuum, e.g., a vacuum chamber, a salt bath, or a bath that removes the solvent in the polymeric mixture. For instance, an aqueous polymeric mixture may be introduced into an ethanol bath, with the ethanol replacing the water. The ethanol may subsequently be removed. A salt bath may be, e.g., a high salt concentration bath (1M to 6M). A time of processing in a solvent-removing environment and/or a cooling process may be independently chosen to be from 1 to 240 hours; Artisans will immediately appreciate that all ranges and values between the explicitly stated bounds are contemplated, with, e.g., any of the following being available as an upper or lower limit: 1, 2, 5, 10, 24 hours, 1, 2, 5, 7, 10 days. Salts may be salts that dissociate to make single, double, or triply charged ions.

One or a plurality of solvent-removing environments may be used, or one environment may be adjusted with respect to temperature. Thus, a cooling bath may be used followed by solvent removal in an oven or vacuum oven. A washing step may be performed before or after cooling or solvent removal, e.g., by soaking in a series of solvents of varying concentrations, varying salt solutions, varying proportions of ethanol or other solvents.

An embodiment is an extruded material that has been through a solvent-removal process comprising exposure to a salt bath, the material is soaked in a series of $H_2O$ baths (new baths or exchanged) for a period of time (e.g., 2-48 hours, 4-24 hours) to remove excess salt from the cast material or end-user device. The material is removed from the wash step and dehydrated to remove excess water. Dehydration can be done using, e.g., temperatures ranging from 20-95° C. Dehydration is generally performed at 37° C. for greater than 24 hours.

An embodiment is a polymeric mixture that has been extruded or otherwise formed that is then exposed to a high salt concentration bath (1M to 6M) for an inversely correlated period of time; high salt reduces the time required for soaking; for instance, it is soaked for 16-24 hours in a 6M solution of NaCl. After soaking, the material is rinsed free of salt solution. The material is now toughened and can be removed from any mold pieces carried over from the initial formation. Alternatively, after a salt or other bath, the material is soaked in water baths and dehydrated to remove excess water. Dehydration can be done using temps ranging from 20-95° C. Dehydration may be performed at 37° C. for greater than 4 hours, greater than 24 hours, or in a range from 2 to 150 hours; Artisans will immediately appreciate that all ranges and values between the explicitly stated bounds are contemplated, with, e.g., any of the following being available as an upper or lower limit: 2, 4, 6, 8, 10, 12, 16, 24, 48, 72, 96, 120, 144, 150 hours. For instance, dehydration at 40° C. for 6-24 hours has been observed to be useful.

In another embodiment, NaCl is incorporated into the starting polymeric solution at concentrations ranging from 0.1 to 3M of the final polymeric mixture volume. A polymer is dissolved in a heated solution under agitation, then brought above its melt point. To this solution, dry NaCl is added slowly under agitation until completely dissolved. The slightly hazy solution is then drawn into a feed for the purpose of creating a shape, either through injection molding, casting, extrusion and/or drawing. A quench is performed at the end of each process to rapidly reduce the temperature and form a solid material. In this embodiment, no additional salt soak is required. After material hardening, if necessary, the material is removed from any molding process parts and rinsed in water to remove salt and dehydrated.

The term annealing, as used in the context of a semicrystalline polymer or a solid porous material refers to a heat treatment at an annealing temperature comparable to the melting temperature of the polymer or the polymers in the relevant material. This temperature is usually less than and is within about 0-15% of the melting temperature on an absolute temperature scale. Plasticizers or other additive materials may affect the melting temperature, usually by depressing it. For a pure PVA, for instance, the annealing temperature will be within about 10% of the melting point of the PVA; with other materials present, the annealing temperature will typically be lower. A theory of operation is that the annealing is a process that is a relaxation of stress combined with increase in the size of crystalline regions in the material being annealed. Unlike metals, annealing increases the strength of the annealed material. Annealing may be performed in one or more of: in air or in a gas or in an absence of oxygen or an absence of water, e.g., in nitrogen, in vacuum nitrogen, under argon, with oxygen scavengers, and so forth. For example, experiments have been made with annealing dehydrated PVA nanoporous materials. Annealing is utilized to increase crystallinity in the PVA network, further reducing pore sizes of the PVA network and to reduce adsorption properties of the final gel surface. Annealing can be done at temperatures ranging from, e.g., 100-200° C.; in a preferred embodiment, this step is performed submerging the dehydrated gel into a bath of mineral oil. Bulk incorporation of a polymer into a porous solid may also include an annealing process as already described above for a porous solid. Annealing may be performed after exposure of the desolvated porous solid to the mixture that has the polymers that are to be bulk incorporated. The Tg of the material may be raised or lowered dependent on the residual solvent content and/or presence of the bulk incorporated second hydrophilic polymer. As already described, the annealing process conditions may thus be adapted as to depend on temperature, time, ramp rate, and cooling rates of the substrate.

Annealing may be performed in a gas or a liquid at ambient, elevated, or low (vacuum) pressure. The liquid may be a low molecular weight polymer (up to 2000 Da) or other material (e.g., mineral oil). Examples of low molecular weight polymers are: silicone oils, glycerin, polyols, and polyethylene glycols of less than 500 Da. A useful embodiment is annealing in a bath of glycerin at, e.g., 140° C. for 1-3 hours; glycerin acts to further reduce fouling properties of the gel through interaction and neutralization of the free hydroxyl end groups of the PVA network. The annealed nanoporous material is allowed to cool, removed from the annealing bath and rinsed free of bath medium using a series of extended soaks. The product is then dehydrated to prepare for terminal sterilization.

Various types of dies may be used, e.g., longitudinal, angular, transverse and spiral extrusion heads, as well as single-polymer extrusion heads used for extruding a single polymer and multi layers extrusion heads used for simultaneous extrusion of a plurality of polymer layers or other layers. Continuous operation heads may be used, as well as cyclical. Various materials may be incorporated into, or as, a layer: for example, a reinforcing material, a fiber, a wire, a braided material, braided wire, braided plastic fibers, and so forth. Similarly, such materials may be excluded. Moreover, the porous solid may be made with a certain property, e.g., Young's modulus, tensile strength, solids content, polymer composition, porous structure, or solvent content that is known and thus measurable exclusive of various other materials. Accordingly, embodiments include materials disclosed herein that are described in terms of the materials' properties without regard to various other incorporated materials. For instance, a nanoporous solid has a certain Young's modulus that is known even if the material has a reinforcing wire that contributes further strength.

A core may be used with an extrusion die. The core may be air, water, a liquid, a solid, a non-solvent or a gas. Artisans reading this disclosure will appreciate that various extrusion processes using these various kinds of cores may be used. Cores made of polytetrafluoroethylene tubing (PTFE) are useful. In some embodiments, a core is a wire.

Multi lumen tubing has multiple channels running through its profile. These extrusions can be custom engineered to meet device designs. Multi Lumen tubing has a variable Outer Diameter (OD), numerous custom Inner Diameters (ID's), and various wall thicknesses. This tubing is available in a number of shapes; circular, oval, triangular, square, semi-circular, and crescent. These lumens can be used for guidewires, fluids, gases, wires, and various other needs. The number of lumens in multi lumen tubing is only limited by the size of the OD. In some embodiments, OD's are as large as 0.5 in., ID's can be as small as 0.002 in., and web and wall thicknesses can be as thin as 0.002 in. Tight tolerances can be maintained to +/−0.0005 in. Artisans will immediately appreciate that all ranges and values between the explicitly stated bounds are contemplated, with, e.g., any of the following being available as an upper or lower limit for an OD and/or ID: 0.002, 0.003, 0.004, 0.007, 0.01, 0.02, 0.03, 0.04, 0.05, 0.1, 0.2, 0.3, 0.4, and 0.5 in. Tolerances may be, e.g., from 0.0005 to 0.1 in.; Artisans will immediately appreciate that all ranges and values between the explicitly stated bounds are contemplated, with, e.g., any of the following being available as an upper or lower limit: 0.0005, 0.001, 0.002, 0.003, 0.006, 0.01, 0.02, 0.03, 0.06, 0.8, 0.9, 1 in.

Braid reinforced tubing can be made in various configurations. For instance, it is possible to braid using round or flat, single or double ended wires as small as 0.001 in. Various materials can be used to make the braided reinforced tubing including stainless steel, beryllium copper, and silver, as well as monofilament polymers. The braid can be wound with various pics per inch over many thermoplastic substrates such as nylons or polyurethanes. The benefits of braided catheter shaft are its high torque-ability and kink resistance. By changing several factors during the braiding process, the characteristics of the tube can be altered to fit performance requirements. After braiding is complete, a second extrusion may be applied on top of the braided tube to encapsulate the braid and provide a smooth finish. Walls as thin as 0.007 in. can be achieved when a braid reinforced tube is required.

Porous, Microporous, and Nanoporous Materials

Porous solid is a term used broadly herein to refer to materials having a solid phase containing open spaces and is used to describe true porous materials and also hydrogels having an open matrix structure. Some terms related to porosity are used somewhat loosely in scientific literature such that it is helpful to provide certain definitions herein. The term nanoporous material or nanoporous solid is used herein to specifically refer to a solid made with interconnected pores having a pore size of up to about 100 nm diameter. The term diameter is broad and encompasses pores of any shape, as is customary in these arts. The term microporous solid or microporous material is similarly used herein to specifically refer to a solid made with interconnected pores having a pore size of up to about 10 am diameter. These nano- or microporous materials are characterized by an interconnected porous structure.

Some hydrogels, which artisans sometimes refer to as hydrogel sponges, are also true porous materials that have a continuous and solid network material filled through voids, with the voids being the pores. However, an open matrix structure found in many hydrogels is not a true porous structure and, in general, while it is convenient to refer to them as porous materials, or to use analogies to pores when characterizing diffusive or other properties, such hydrogels are not nanoporous or microporous solids as those terms are used herein. The spaces between strands of an open matrix hydrogel, and the strands of the matrix are not interconnected pores. Hydrogels are crosslinked gels that have solid-like properties without being a true solid although it is convenient herein and generally in these arts to refer to them as a solid because they are crosslinked, insoluble in solvent, and have significant mechanical strength. Hydrogels may have a high-water content, e.g., 25% w/w at EWC or more. Artisans in the hydrogel arts sometimes use the term porous, to characterize a net molecular weight cut off or to refer to spacing between strands of an open hydrogel matrix, in which case the hydrogel does not have a true porous structure and is not a nanoporous or a microporous material as those terms are used herein. The definitions of nanoporous material and microporous material as used herein also contrast with a convention that is sometimes followed wherein microporous substances are described as having pore diameters of less than 2 nm, macroporous substances have pore diameters of greater than 50 nm, and a mesoporous category lies in the middle.

The extrusion process for making the inventive materials has some advantages. The extrusion has been observed to align the polymers to a parallel orientation that contributes to high tensile strength. Having been extruded and stretched, the polymer molecules become aligned in the direction of the tube or fiber. Any tendency to return to a random orientation is prevented by the strong intermolecular forces between the molecules. Further, extrusion provides for creation of materials or devices with a high aspect ratio as compared to injection molding or other molding processes. Moreover, extrusion provides good control of dimensions such that wall thickness, placement of the lumen or lumens can be controlled. The use of high concentrations of polymers, above their melt point, in a solvent was useful for enabling extrusion. It is significant that attempts by others to use similar polymers to make high strength materials used other techniques that do not allow for extrusion, that are less efficient, and often unsuited for making actual end-user products.

For example, poly(vinyl alcohol) (PVA) was used herein to make nanoporous materials with excellent properties, especially as compared to conventionally used PVA medical materials. In fact, PVA has been used extensively throughout the medical device industry with a well-established track record of biocompatibility. PVA is a linear molecule with an extensive history as a biocompatible biomaterial. PVA hydrogels and membranes have been developed for biomedical applications such as contact lenses, artificial pancreases, hemodialysis, and synthetic vitreous humor, as well as for implantable medical materials to replace cartilage and meniscus tissues. It is an attractive material for these applications because of its biocompatibility and low protein adsorption properties resulting in low cell adhesion compared with other hydrogels.

Others have tried to improve the properties of PVA for biomedical purposes. For instance, others have experimented with a freeze/thaw process. And techniques for formation of hydrogels from PVA such as "salting out" gelation have been shown to form useful polymer hydrogels using different molecular weights and concentrations. Manipulation of Flory interactions has also been studied in the formation of PVA gels through the combination of two solutions (see U.S. Pat. Nos. 7,845,670, 8,637,063, 7,619,009) for the use of PVA as an injectable in situ forming gel for repairing intervertebral disks. In general, prior processes for fabricating tough PVA materials were studied in U.S. Pat. No. 8,541,484. Methods for doing so without the use of radiation or chemical crosslinkers have also been previously studied, as shown in U.S. Pat. No. 6,231,605. None of this PVA-related work by others has resulted in the inventions that are set forth herein. Some of these other materials were useful in regards to tensile strength but were nonetheless macroporous in nature.

In contrast, processes herein provide high strength materials with a true porous structure and other useful characteristics such as an unexpectedly good combination of biocompatibility and mechanical properties. Embodiments of porous solid materials are provided that have a combination of structural features independently chosen from pore sizes, tensile strength, Young's modulus, solids concentration, crosslinking type and degree, internal alignment, hydrophilicity, and composition for the materials and further, optionally, independently selecting end-user devices or intermediate materials having a desired aspect ratio for molded shapes, a lumen, a plurality of lumens, tubes with concentrically placed lumens or a range of tolerance of thickness, or a particular medical device: each of these are further detailed herein.

Embodiments include nanoporous materials with pore diameters of 100 nm or less, or within a range of 10-100 nm; Artisans will immediately appreciate that all ranges and values between the explicitly stated bounds are contemplated, with, e.g., any of the following being available as an upper or lower limit: 1, 2, 3, 4, 5, 10, 20, 50, 60, 70 80, 90, 100 nm.

Embodiments include nanoporous materials or microporous materials with a tensile strength at break of at least about 50 MPa or from 1-300 MPa measured at EWC. Artisans will immediately appreciate that all ranges and values between the explicitly stated bounds are contemplated, with, e.g., any of the following being available as an upper or lower limit: 10, 20, 30, 40, 50, 60, 70, 100, 200, 300 MPa.

Embodiments include nanoporous materials or microporous materials with a Young's modulus strength of at least about 1 MPa or from 1-200 MPa measured at EWC. Artisans will immediately appreciate that all ranges and values between the explicitly stated bounds are contemplated, with, e.g., any of the following being available as an upper or lower limit: 5, 10, 15, 20, 25, 30, 35, 40, 50, 60, 70, 80, 90, 100, 120, 140, 160, 180, 200 MPa.

Embodiments include nanoporous materials or microporous materials or hydrogels with an elongation at break of at least about 100% or from 50-1500% measured at EWC. Artisans will immediately appreciate that all ranges and values between the explicitly stated bounds are contemplated, with, e.g., any of the following being available as an upper or lower limit: 50, 60, 70, 80, 90, 100, 200, 300, 400, 450, or 500% (e.g., greater than or equal to 50%).

Embodiments include nanoporous materials or microporous materials or hydrogels with a solids content of at least 20% or solids from 20-90% w/w measured at EWC; Artisans will immediately appreciate that all ranges and values between the explicitly stated bounds are contemplated, with, e.g., any of the following being available as an upper or lower limit: 5, 10, 25, 30, 35, 40, 45, 50, 55, 60, 65, 70, 80, 90% w/w percent solids. Percent solids are measured by comparing a total weight at EWC to dry weight.

The tensile strength, modulus, and elongation values may be mixed-and-matched in combinations within the ranges as guided by this disclosure.

Embodiments include nanoporous materials or microporous materials or hydrogels with physical crosslinks or covalent crosslinks or a combination thereof. Physical crosslinks are noncovalent, e.g., physical crosslinks are ionic bonds, hydrogen bonds, electrostatic bonds, Van Der Waals forces, or hydrophobic packing. The materials may be made free of covalent crosslinks, covalent crosslinkers and chemical products thereof. Chemicals can be added during processing to create covalent crosslinks, as is known in the arts of polymerization. Alternatively, the processes and materials may be free of the same.

Embodiments include nanoporous materials or microporous materials or hydrogels with an internal alignment of the polymeric structure. Alignment may be visualized using SEM images in sections taken along the direction of extrusion, i.e., longitudinally for a tube. Alignment refers to a majority horizontal chain orientation and along the length of samples (in direction of extrusion).

Embodiments include nanoporous materials or microporous materials or hydrogels with a hydrophilic surface and/or material. Materials made from polymers that are water soluble are hydrophilic. A water-soluble polymer is a polymer that is soluble in water at a concentration of at least 1 g/100 ml at 20° C. Water soluble polymers are hydrophilic. A surface is hydrophilic if a contact angle for a water droplet on the surface is less than 90 degrees (the contact angle is defined as the angle passing through the drop interior). Embodiments include hydrophilic surfaces with a contact angle from 90 to 0 degrees; Artisans will immediately appreciate that all ranges and values between the explicitly stated bounds are contemplated, with, e.g., any of the following being available as an upper or lower limit: 90, 80, 70, 60, 50, 40, 30, 20, 10, 5, 2, 0 degrees. A matrix of a material is hydrophilic relative to a solvent when the matrix is hydrophilic and a droplet of the solvent on the surface is less than 90 degrees.

Materials for use in the process and/or biomaterials may include polymers. Hydrophilic polymers are useful, e.g., one or more polymers may be selected from polyvinyl alcohol (PVA), polyvinylpyrrolidone (PVP), polyethylene glycol (PEG), polyacrylic acid (PAA), polyacrylamide, hydroxypropyl methacrylamide, polyoxazolines, polyphosphates, polyphosphazenes, poly(vinyl acetate), polypropylene glycol, Poly(N-isopropylacrylamide) (PNIPAM), polysaccharides, sulfonated hydrophilic polymers (e.g., sulfonated polyphenylene oxide, Nafion®, sulfobetaine methacrylate) and variations of the same with an added iodine (e.g., PVA-I, PVP-I), or variations with further pendent groups, copolymers of the same, and combinations of the same. Two or more hydrophilic polymers may be intermixed together to form a nanoporous material. The molecular weight of the polymer can affect the properties of the biomaterial. A higher molecular weight tends to increase strength, decrease pore size, and decrease protein adsorption. Accordingly, embodiments include a polymer or a hydrophilic polymer having a molecular weight of 40 kDa to 5000 kDa; Artisans will immediately appreciate that all ranges and values between the explicitly stated bounds are contemplated, with, e.g., any of the following being available as an upper or lower limit: 40 k, 50 k, 100 k, 125 k, 150 k, 250 k, 400 k, 500 k, 600 k 750 k, 800, 900 k, 1 million, 1.5 million, 2 million, 2.5 million, 3 million molecular weight.

The term PEG refers to all polyethylene oxides regardless of molecular weight or whether or not the polymers are terminated with a hydroxyl. Similarly, the terms PVA, PVP, and PAA are used without limitation as to terminal chemical moieties or MW ranges. References to polymers described herein include all forms of the polymers including linear polymers, branched polymers, underivatized polymers, and derivatized polymers. A branched polymer has a linear backbone and at least one branch and is thus a term that encompasses star, brush, comb, and combinations thereof. A derivatized polymer has a backbone that comprises the indicated repeating unit and one or more substitutions or pendant groups collectively referred to as derivatizing moieties. A substitution refers to a replacement of one atom with another. A pendant group is a chemical moiety attached to the polymer and may be the same or a different moiety as the polymer repeating unit. Accordingly, a reference to a polymer encompasses highly derivatized polymers and also polymers no more than 0.01-20% w/w derivatizing moieties, calculated as the total MW of such moieties compared to the total weight of the polymer. Artisans will immediately appreciate that all ranges and values between the explicitly stated bounds are contemplated, with, e.g., any of the following being available as an upper or lower limit: 0.01, 0.05, 0.1, 0.2, 0.3, 0.5, 1, 2, 3, 4, 5, 6, 7, 8, 9, 10, 15, 20% w/w.

A porous solid may be formed as a monolithic material, as a layer on another material, device, or surface, as a plurality of layers, or as one or more layers of a nanoporous material or a material that comprises a nanoporous material. Thus, for example, a plurality of layers may be extruded, with the layers being independently chosen to form one or more of: a nanoporous material, a microporous material, a hydrogel, a single-polymer material, a material having two or more polymers, and a non-nanoporous material.

The process of making the material can also affect the material properties, including the concentration of polymer in the polymeric mixture passed through a die. Starting PVA or other hydrophilic polymer concentrations may range from, e.g., 5 to 70% weight-volume (w/w) in water; generally, about 10-30% (w/w) is preferable; Artisans will immediately appreciate that all ranges and values between the explicitly stated bounds are contemplated, with, e.g., any of the following being available as an upper or lower limit: 5, 10, 15, 20, 25, 30, 35, 40, 45, 50, 55, 60, 65, 70 percent.

Processes set forth herein may be truncated at a point before polymers crosslink and are processed to become a true nanoporous material, or otherwise adapted to avoid a nanoporous structure. In general, such materials have a lesser strength and toughness and lower solids content. Such materials are generally hydrogels when hydrophilic polymers are used at relatively low solids content. Accordingly, such materials, and even hydrogels, are contemplated herein, and materials may be made that are of somewhat lesser characteristics as compared to the nanoporous materials but, nonetheless, are superior to conventional processes and materials that use the same polymers. Similarly, and as a generalization, a microporous solid would have properties that approach those of the nanoporous materials and would have a strength better than those of a hydrogel.

Artisans are accustomed to quantifying pore size distributions in materials. Nanoporous, microporous, and microporous materials are disclosed herein and control of the pore sizes of such material is demonstrated. Embodiments thus include materials that have a particular quantity or distribution of pore sizes. These can be measured at a surface, in a depth from the surface in a cross-sectional sample, or for the bulk of the material. For instance, the material pore sizes on a surface, at a depth from a surface, or in a bulk may have a percentage from 50-100% of pore diameters that fall within a range, or above or below a certain value, from 1 nm to 20 jam; Artisans will immediately appreciate that all ranges and values between the explicitly stated bounds are contemplated, e.g., 10, 20, 30, 40, 50, 60, 65, 70, 75, 80, 90, 95, 98, 99, 99.9 or 100% and 1, 10, 20, 30, 40, 50, 100, 200, 400, 500, 1000, 2000, 3000, 5000, 10000, 15000, or 20000 nm. Examples of quantitation relative to a depth are at a depth of e.g., at least, or in a range of, 1-5000 jam; Artisans will immediately appreciate that all ranges and values between the explicitly stated bounds are contemplated: 1, 2, 3, 4, 5, 10, 20, 50, 100, 250, 500, 750, 1000, 2000, 3000, 4000, or 5000 µm. For example, a surface may have a certain percentage of pores that are no more than a certain diameter or a depth or depth range may have a certain percentage of pores that are no more than a certain diameter.

Embodiments include a process for making a polymeric material comprising heating a mixture that comprises a water-soluble polymer and a solvent to a temperature above the melting point of the polymer, extruding the mixture, and cooling the mixture while removing the solvent and/or cooling the mixture while it crosslinks. When a plurality of polymers is present in a solvent, either with or without other additives, a melting point of the combined polymers in the solvent can be readily determined by the artisan, for instance by observing the mixture as it is heated and it passes from a cloudy to a markedly more translucent appearance. Further, after, or as part of, a formation process that uses the mixture, some or all of the solvent may be removed from the mixture while the cooling takes place. Embodiments include removing at least 50% w/w of the solvent in less than 60 minutes (or less than 1, 2, 5, or 10 minutes). Embodiments include removing at least 90% w/w (or at least 70% w/w or at least 80% w/w) of the solvent in less than 60 minutes (or less than 1, 2, 5, 10, or 30 minutes).

Bulk Incorporation of Polymers into a Porous Solid

A porous material may be exposed to a mixture comprising solvated polymers (for bulk incorporated polymers) to draw them into the pores when the porous matrix is desolvated. The solvent of the mixture has an affinity for the matrix and is drawn in as the matrix imbibes the solvent. The solvent in the mixture with the bulk incorporated polymers can be chosen to have an affinity for the matrix so that it is imbibed into the desolvated matrix but does not have to be the same as the solvent in the matrix. In general, a hydrophilic solvent in the mixture will be imbibed into a hydrophilic porous matrix that is at least partially desolvated and contains a hydrophilic solvent, and an artisan can adjust the various solvents as needed to create suitable conditions when the goal of bulk incorporation is intended.

A hydrophilic solvent is a solvent that is freely miscible with water or is present at a concentration in the mixture wherein it is freely miscible with water, at 20° C.

Desolvated means that the matrix is free of solvents, e.g., completely dry, or is below an EWC of the matrix relative to the solvent it contains. If the solvent in the matrix is not water, the EWC can be calculated for the material based on measurements in the solvent, i.e., the term EWC can be used for solvents that are not water in the appropriate context. For instance, a hydrophilic matrix might be solvated in an aqueous solution of an alcohol and would have an EWC for that solvent. Embodiments include an amount of desolvation of a porous solid from 1-100, Artisans will immediately appreciate that all ranges and values between the explicitly stated bounds are contemplated: 1, 5, 10, 15, 20, 33, 40, 50, 60, 70, 80, 90, 95, 99, 100% w/w referring to the total weight of solvent that can be removed.

Without being bound to a particular theory, it is believed that porous materials can be desolvated (dehydrated in the case of water being the solvent in the porous material) and exposed to polymers in a solution that resolvates the porous material so that the polymers are drawn into the pores. The polymers then form physical bonds with the matrix material that defines the pores and are, for practical purposes, permanently incorporated into the bulk of the materials, both by at least partially filling the pores and by physical bonding with the matrix. Alternatively, or additionally, the polymers have a hydrodynamic radius that causes the polymer to present a diameter that exceeds the pores' opening diameter so that the polymer is permanently incorporated into the pores of the material, especially when the material is to be used in water or physiological solution. In general, if the bulk-incorporated polymer is solvated in a polymer that wets the pores of the porous solid, the polymer can be drawn into pores of the matrix as it is resolvated. When a hydrophilic porous matrix is below an EWC of the matrix, the mixture that contains the polymers for bulk incorporation is drawn in because the solvent for the polymers is matched to the matrix material, e.g., wets the pores of the material. For instance, a hydrophilic solvent will normally wet the pores of a hydrophilic matrix.

A material that comprises a porous matrix of polymers joined by noncovalent bonds is a preferred embodiment, since these materials can be made with a high degree of control over pore sizes and material properties, including a choice of nanoporous, microporous, or other characteristic pore sizes. The matrix may comprise physically crosslinked water-soluble polymers that define the pores. A solids concentration of these water-soluble polymers may be at least 33% w/w of the matrix at an equilibrium water content (EWC) of the matrix, although other concentrations may also be used.

Accordingly, an embodiment of a process of incorporating polymers in a porous material comprises providing a material comprising a porous, hydrophilic matrix that comprises one or more water soluble polymers (also referred to herein as matrix polymers) crosslinked with each other to form the matrix. The material with the matrix is exposed to a mixture comprising one or more polymers (also referred to as bulk incorporated polymers, preferably with the polymers being water soluble, with the mixture also being referred to as a conditioning mixture or bulk incorporating mixture) solvated in a solvent, wherein the matrix is below the EWC before being exposed to the mixture and is hydrophilic relative to the solvent. The material, before exposure to the mixture with the bulk incorporated polymers, is desolvated.

In some embodiments, bulk incorporation processes create an outer zone wherein the pores are filled, an intermediate zone where most of the pores are filled or are mostly filled, and an inner zone where there is little or no penetration of the polymers. Bulk incorporation not only modifies pores at a surface but also below the surface, e.g., at least, or in a range of, 1-5000 jam; Artisans will immediately appreciate that all ranges and values between the explicitly stated bounds are contemplated, e.g., 1, 2, 3, 4, 5, 10, 20, 30, 40, 50, 75, 100, 250, 500, 750, 1000, 2000, 3000, 4000, or 5000 μm. The percentage of pores that have polymer may be assayed as already described and penetration graded by a cut-off of a percentage, e.g., a first zone having 100% filling of pores, a second zone with 50% pores filled, a third zone with 0% pores filled.

Bulk incorporation processes are preferably made with porous matrices that are made of water soluble polymers and may be made without hydrophobic domains in the polymers, e.g., a matrix made only of PVA. The polymers may form the matrix with physical crosslinks. Accordingly, embodiments include materials comprising matrices that are free of hydrophobic domains or that are made with water soluble polymers that are free of hydrophobic domains or that are free of any polymer that is not water soluble. Some hydrophobic domains can be tolerated, however, when making a hydrophilic matrix with water soluble polymers having physical crosslinks without disrupting the matrix formed thereby. Embodiments of the invention include a hydrophobic content of polymers that form a porous matrix of 0, 1, 2, 3, 4, 5, 7, 8, 9, 10, 11, 12, or 15% w/w.

A porous matrix consisting essentially of water soluble polymers refers to a content of up to 3% w/w of the polymers that crosslink to form the matrix. RO agents such as salts are not polymers that crosslink to form the matrix. A porous matrix consisting essentially of physically crosslinked polymers refers to a matrix that is free of agents that make covalent bonds between the polymers, or has a small amount of such agents so that no more than about 6% of the polymers (referring to polymer number) are crosslinked to each other with such agents, e.g., wherein a stoichiometric ratio of polymer number to a bifunctional crosslinker is at least 100:3. A matrix that is essentially free of covalent bonds similarly is made with polymers crosslinked with no more than about 6% of the polymers (by number) are not covalently crosslinked. The number of covalent bonds in a matrix may similarly be limited to a stoichiometric ratio of 100:3 to 100:100, e.g., 100 to any of 3, 5, 10, 15, 20, 25, 30, 40, 50, 60, 70, 80, 90, or 100 by number. For instance, hydrogels made by free radical polymerization typically have 100% of the polymers attached to each other by covalent bonds, which is a 100:100 stoichiometric ratio of polymers:covalent bonds.

As stated elsewhere, a porous solid can be made with a controlled pore diameter range and may be made to provide a matrix that has no pores larger than a particular diameter. Diameters may be measured in an appropriate context, e.g., at EWC in distilled water. Embodiments thus include polymers entrapped in a porous matrix that is free of pores that are larger than 1-5000 jam; Artisans will immediately appreciate that all ranges and values between the explicitly stated bounds are contemplated, e.g., 1, 2, 3, 4, 5, 10, 15, 20, 25, 30, 50, 100, 200, 250, 300, 400, 500, 750, 1000, 2000, 3000, 4000, or 5000 μm.

A porous solid can have other materials present as described elsewhere herein, e.g., radiopaque (RO) agents that are additional to the matrix but are not part of the matrix. RO agents typically contribute little to the crosslinking that provides the strength of the matrix. Similarly, other materials can be present in the matrix without being part of the matrix, e.g., wires and reinforcing materials. It can be appreciated that a matrix made with physical crosslinks is one type of matrix that can be made with materials that define pores that have diameters and is in contrast to hydrogels having polymer strands that are generally separated from each other and are connected in a mesh network structure, e.g., as typically formed using free radical polymerization or by reaction of monomers/polymers that are in solution. Such mesh networks would generally not be expected to stably incorporate polymers in their pores without covalent bonding using a polymer-imbibing process. Porous materials are described in detail herein and these may be freely chosen, as guided by the disclosure herein, for use with bulk incorporated polymers. The porous material may be chosen with bulk properties as described herein.

The bulk incorporated polymers may be polymers described elsewhere herein for porous solids. Examples are water-soluble polymers. The water soluble polymers may be, for example, polyvinyl alcohol (PVA), polyvinylpyrrolidone (PVP), polyethylene glycol (PEG), polyacrylic acid (PAA), polyacrylamide, hydroxypropyl methacrylamide, polyoxazolines, polyphosphates, polyphosphazenes, poly(vinyl acetate), polypropylene glycol, Poly(N-isopropylacrylamide) (PNIPAM), polysaccharides, sulfonated hydrophilic polymers (e.g., sulfonated polyphenylene oxide, Nafion®, sulfobetaine methacrylate) and variations of the same with an added iodine (e.g., PVA-I, PVP-I), or variations with further pendent groups, copolymers of the same, and combinations of the same. The mixture may comprise one or more polymers, meaning polymers of different chemical compositions, such as PVA and PEG. The term "a polymer" refers to one or more polymers.

The solubility of a water-soluble polymer for a porous matrix or for bulk incorporation may be chosen as, e.g., at least 1, 2, 5, or 10 g/100 ml in water at 20° C. Polymers may be chosen to be linear or branched. Embodiments include a polymer or a hydrophilic polymer having a molecular weight of, e.g., 40 k to 5000 k Daltons; Artisans will immediately appreciate that all ranges and values between the explicitly stated bounds are contemplated, with, e.g., any of the following being available as an upper or lower limit: 40 k, 50 k, 100 k, 125 k, 150 k, 250 k, 400 k, 500 k, 600 k, 750 k, 800, 900 k, 1 million, 1.5 million, 2 million, 2.5 million, 3 million molecular weight. The molecular weight of the polymer can be chosen in light of the pore sizes available in the porous solid. Nanoporous or microporous materials are preferred.

The bulk incorporated polymers may be chosen to be the same as polymers that form the porous matrix, to be the same as at least one of the polymers that make up the matrix, or to be different.

The bulk incorporated polymer concentrations in the mixture may be, referring to the mixture at the start of the process, any concentration wherein the polymers go into solution, bearing in mind that polymer that is not in solution, or other non-solvated materials, are not destined to enter pores. In some embodiments, concentrations are 1-50% w/w; Artisans will immediately appreciate that all ranges and values between the explicitly stated bounds are contemplated, e.g., 1, 2, 3, 4, 5, 10, 15, 20, 25, 30, 33, 35, 40, 50% w/w.

Solvent for the mixture is chosen as appropriate to solvate the polymer and to provide a solvent that will be imbibed by the porous solid. Hydrophilic solvents are generally preferable for a hydrophilic matrix. Solvents may be water, organic, or aqueous, or free of the same, e.g., free of organic solvent. In some embodiments, concentrations of water are 0-99, e.g., 0, 5, 10, 15, 20, 25, 30, 40, 50, 60, 70, 80, 90, 95, or 99 w/w %.

A temperature of the conditioning mixture is not to exceed a melting temperature of the porous solid matrix. Temperatures ranges may be, for example, from 10-100° C., e.g., 10, 20, 30, 37, 40, 50, 60, 70, 80, or 90° C.

Exposure times are preferably for a duration of time required for a porous solid to reach EWC in the mixture. Duration of time may comprise, in some embodiments, 2, 4, 6, 8, 10, 12, 16, 20, 24, and 48 hours. Agitation and temperature may be manipulated to affect a time of exposure, e.g., to accelerate achieving EWC or to control viscosity of the mixture. Salt and/or osmotic content may be adjusted as helpful, e.g., for solubility, viscosity, and/or EWC.

The Examples provide guidance in regards to salt concentration for a conditioning mixture. Examples of salt concentration are from 0.1 to 2% w/w. In general, a single charge cation with a smaller atomic radius has a greater penetration into a depth of a porous solid, whereas a larger cation reduces penetration. Examples of salts are those with a single cation, divalent cation, or other cation, e.g., a salt of sodium, potassium, lithium, copper, quaternary ammonium ($NR_4^+$, where R is a hydrogen, alkyl, or aryl group), magnesium, calcium, copper, iron, or zinc. In general, a physiological pH using a buffer was useful for the mixture. A pH may be adjusted to increase or decrease penetration into a matrix, and the solvent may include or omit buffering salts. Examples of pH are from 4-10, e.g., 4, 5, 6, 7, 8, 9, or 10.

A viscosity of a conditioning mixture, referring to a water-soluble polymer and solvent, is affected by: pH (higher pH, higher viscosity), polymer concentration and/or molecular weight, and polymer branching, with increases in any of these generally leading to a higher viscosity. In general, a higher viscosity reduces penetration of the bulk incorporating polymers into a porous solid. An embodiment is a porous material comprising water soluble polymers entrapped in pores of a porous matrix. The matrix may comprise physically crosslinked water-soluble polymers that are crosslinked with each other to form the matrix and define the pores. The matrix may have features as disclosed herein, e.g., polymer content, weight percentage of polymers, strength, Young's modulus, degree of coverage, pore sizes, and so forth.

Surface coverage of the water-soluble polymers in a porous matrix may be complete. Complete coverage under SEM conditions wherein no pores of the underlying surface are visible indicates coverage at EWC. A degree of coverage may be less than 100%, e.g., from 50-100%; Artisans will immediately appreciate that all ranges and values between the explicitly stated bounds are contemplated, e.g., 50, 60, 70, 80, 90, 95, 98, 99, 99.9, or 100%.

Bulk incorporation can decrease physical properties of a porous solid. Embodiments thus include a porous solid, e.g., one as disclosed herein, with a Young's modulus and/or tensile strength that is from 1-20% less as a result of being conditioned with a water-soluble polymer as compared to the same material that has not been conditioned with a water-soluble polymer; Artisans will immediately appreciate that all ranges and values between the explicitly stated bounds are contemplated, e.g., 1, 2, 3, 4, 5, 7, 9, 10, 12, 15, or 20%. Example 22 provided a test for exposure of a material for stable incorporation of a water-soluble polymer. A test for incorporation of water soluble polymers to be stable is: Immersion of the test device in physiologically representative fluid (i.e. PBS) at body temp conditions in a circulating peristaltic loop with the test device placed directly in the head of the pump at a flow rate of 10-12 mL/s for 24 hrs at 150 rpm, approximating 500,000 mechanical sample compressions with a volume flux rate of 0.1225 $cm^3 * s^{-1} * cm^{-2}$. While testing revealed as much as a 25% loss, other test criteria may be used, e.g., a loss of 0-50% w/w, e.g., 1, 5, 10, 15, 20, 25, 30, 40, 50% w/w. Or other tests may be posed, e.g., a loss of 0-5% w/w e.g., 1, 2, 3, 4, or 5% w/w at 1-52 weeks of static exposure to an excess of PBS, e.g., 1, 2, 3, 4, 5, 10, 20, 30, 40, 50, or 52 weeks.

Products

Products, including end-user or intermediate products, or materials, may be made that have an aspect ratio as desired, e.g., at least 3:1, referring to materials set forth herein including nanoporous materials, microporous materials, and hydrogels. The aspect ratio increases as the device increases in length and decreases in width. Artisans will immediately appreciate that all ranges and values between the explicitly stated bounds are contemplated, with, e.g., any of the following being available as an upper or lower limit: 3:1, 4:1, 5:1, 6:1, 7:1, 8:1, 9:1, 10:1, 50:1, 100:1, 1000:1. A high aspect ratio is highly advantageous for certain devices, e.g., many types of catheters. In principle, a thin tube could be continuously extruded without limitation as to length. Such devices include, e.g., tubes, rods, cylinders, and cross-sections with square, polygonal, or round profiles. One or more lumens may be provided in any of the same. The devices may be made of a single material, essentially a single material, or with a plurality of materials including the various layers already discussed, or a reinforcing material, a fiber, a wire, a braided material, braided wire, braided plastic fibers.

The extrusion process, in particular, provides for concentric placement of a lumen; concentric is in contrast to eccentric meaning the lumen is off-center. In the case of a plurality of lumens, the lumens may be placed so that the lumens are symmetrically placed: the symmetry is in contrast to an eccentric placement of the lumens that is a result of a poorly controlled process. Embodiments include the aforementioned devices with an aspect ratio of at least 3:1 with lumens that are positioned without eccentricity or one lumen that is concentric with the longitudinal axis of the device.

The porous solids such as the nanoporous materials, microporous materials, and strong hydrogels may be used to make catheters or medical fibers. These may be made with bulk incorporated polymers and may have the various features described for the same. Examples of catheters are central venous, peripherally inserted central, midline, peripheral, tunneled, dialysis access, hemodialysis, vascular access port, peritoneal dialysis, urinary, neurological, peritoneal, intra-aortic balloon pump, diagnostic, interventional, drug delivery, etc.), shunts, wound drains (external including ventricular, ventriculoperitoneal, and lumboperitoneal), and infusion ports. The porous solids may be used to make implantable devices, including fully implantable and percutaneously implanted, either permanent or temporary. The porous solid materials may be used to make blood-contacting devices or devices that contact bodily fluids, including ex vivo and/or in vivo devices, and including blood contacting implants. Examples of such devices include drug delivery devices (e.g., insulin pump), tubing, contraceptive devices, feminine hygiene, endoscopes, grafts (including small diameter <6 mm), pacemakers, implantable cardioverter-defibrillators, cardiac resynchronization devices, cardiovascular device leads, ventricular assist devices, catheters (including cochlear implants, endotracheal tubes, tracheostomy tubes, drug delivery ports and tubing, implantable sensors (intravascular, transdermal, intracranial), ventilator pumps, and ophthalmic devices including drug delivery systems. Catheters can comprise a tubular nanoporous material with a fastener to cooperate with other devices, e.g., luer fasteners or fittings. Radiopaque agents may be added to the materials, fibers, or devices. The term radiopaque agent refers to agents commonly used in the medical device industry to add radiopacity to materials, e.g., barium sulfate, bismuth, or tungsten. RO agents may be incorporated at, e.g., from 5-50% w/w pf the total solids weight, e.g., 5, 10, 20, 30, 40, or 50%.

Medical fibers made with porous solid materials include applications such as sutures, yarns, medical textiles, braids, mesh, knitted or woven mesh, nonwoven fabrics, and devices based on the same. The fibers are strong and pliable. Materials may be made with these fibers so that they are resistant to fatigue and abrasion.

In an exemplary embodiment, the method comprises administering, into an external orifice of a subject, a device comprising a body portion wherein the body portion comprises a polymeric material comprising a water-soluble polymer and a biologically active agent associated with the polymeric material. In some embodiments, the device has an aspect ratio of greater than or equal to 3:1. In some embodiments, the biologically active agent is distributed within the polymeric material substantially homogeneously. In some embodiments, the biologically active agent is distributed within the polymeric material non-homogeneously (i.e., on one or more surfaces of the polymeric material). In some embodiments, administration of the device (e.g., device 10 of FIG. 1A, device 12 of FIG. 1B, device 14 of FIG. 1C) does not comprise the use of a sheath introducer. The polymeric material is substantially non-thrombogenic, the polymeric material has a water content of less than 5 w/w % and greater than or equal to 0.1 w/w % in the first configuration (e.g., a water content less than the equilibrium water content state, such as the dehydrated state), and the polymeric material is configured to swell in an amount greater than or equal to 5 w/w % and less than or equal to 50 w/w % from a first configuration (e.g., a water content less than the equilibrium water content state, such as the dehydrated state) to a second configuration (e.g., an equilibrium water content state) in less than or equal to 60 minutes (e.g., less than or equal to 10 minutes, less than or equal to 5 minutes, less than or equal to 1 minute, or less than or equal to 10 seconds).

Methods of Treatment

In some aspects, methods of treating a subject are described. In some embodiments, the method comprises administering, into an orifice of a subject, a device described herein (e.g., any embodiment of a device described herein or combinations thereof).

In some embodiments, the method comprises swelling the polymeric material as described herein. For example, in some embodiments, the method comprises swelling the device and/or polymeric material in an amount greater than or equal to 2 w/w %, greater than or equal to 3 w/w %, greater than or equal to 4 w/w %, greater than or equal to 5 w/w %, greater than or equal to 10 w/w %, greater than or equal to 15 w/w %, greater than or equal to 20 w/w %, greater than or equal to 25 w/w %, greater than or equal to 30 w/w %, greater than or equal to 35 w/w %, greater than or equal to 40 w/w %, or greater than or equal to 45 w/w %, for example, from a first configuration (e.g., a water content less than the equilibrium water content state, such as the dehydrated state) to a second configuration (e.g., the equilibrium water content state). In some embodiments, the method comprises swelling the device and/or polymeric material in an amount less than or equal to 50 w/w %, less than or equal to 45 w/w %, less than or equal to 40 w/w %, less than or equal to 35 w/w %, less than or equal to 30 w/w %, less than or equal to 25 w/w %, less than or equal to 20 w/w %, less than or equal to 15 w/w %, or less than or equal to 10 w/w %, for example, from a first configuration (e.g., a water content less than the equilibrium water content state, such as the dehydrated state) to a second configuration (e.g., the equilibrium water content state). Combinations of these ranges are also possible (e.g., greater than or equal to 5 w/w % and less than or equal to 40 w/w %).

In some embodiments, the method comprises swelling the polymeric material to the equilibrium water content state. In some embodiments, the method comprises swelling the polymeric material to the equilibrium water content state over a duration of time. In some embodiments the duration of time is less than or equal to 60 minutes (e.g., less than or equal to 10 minutes, less than or equal to 5 minutes, less than or equal to 1 minute, less than or equal to 30 seconds, or less than or equal to 10 seconds).

In some embodiments, the method comprises swelling the polymeric material at a given temperature. In some embodiments, the temperature is greater than or equal to 4° C., greater than or equal to 10° C., greater than or equal to 16° C., greater than or equal to 20° C., greater than or equal to 25° C., or greater than or equal to 30° C. In some embodiments, the temperature is less than or equal to 40° C. less than or equal to 30° C., less than or equal to 25° C., less than or equal to 20° C., less than or equal to 16° C., or less than or equal to 10° C. Combinations of these ranges are also possible (e.g., 20° C.-40° C.).

In some embodiments, the method comprises swelling the polymeric material such that the inner diameter and/or outer diameter increase by a larger percentage than the percentage increase in length (as described herein). For example, in some embodiments, the method comprises swelling the polymeric material such that the inner diameter and/or outer diameter increases by 1-20% while the length increases by 0.1-19%.

In some embodiments, the swelling occurs after administration. In some embodiments, the swelling of the polymeric material after administration into an orifice of a subject closes an opening of that orifice. For example, in some embodiments, the swelling of the polymeric material results in an increase in size to a dimension greater than or equal to the size of the orifice to which it is inserted. In some embodiments, the orifice is a wound. In some embodiments, the swelling of the polymeric material causes hemostasis. For example, in some embodiments, a subject (e.g., a human) may have an orifice (e.g., a wound) that has a maximum cross-sectional diameter of A and that is bleeding, and a device described herein with a maximum outer cross-sectional diameter smaller than A may be administered into the orifice. In some embodiments, the maximum outer cross-sectional diameter of the device may then swell to a dimension greater than or equal to A, such that the orifice is closed. In some embodiments, this may result in hemostasis.

In some embodiments, the swelling occurs before administration. In some embodiments, the swelling comprises rehydrating the device for a duration of time. In some embodiments, the duration of time is less than or equal to 60 minutes (e.g., less than or equal to 10 minutes, less than or equal to 5 minutes, less than or equal to 1 minute, or less than or equal to 10 seconds). In some embodiments, rehydrating the device comprises use of rehydration media. In some embodiments, the rehydration media comprises water, lactated Ringer's solution (LRS), dextrose (D5W), phosphate buffered saline (PBS), Hanks' Balanced Salt Solution (HBSS), and/or isotonic salt solutions.

Kits

In some aspects, kits are described. The kit may comprise any suitable articles described herein. In some embodiments, the kit comprises a device (e.g., any embodiment of a device described herein or combinations thereof).

In some embodiments, the kit further comprises a humidity control sponge. The humidity control sponge may comprise a woven, non-woven, porous, and/or solid material comprising water and/or hydration media. In some embodiments, the humidity control sponge is a porous cellulose non-woven fabric swollen with water. In some embodiments, the humidity control sponge further comprises an antiseptic or anti-infective agent (e.g., bleach, sodium hypochlorite, peroxides, and/or peracetic acid).

In some embodiments, the kit further comprises hydration media. Non-limiting examples of suitable hydration media include water, lactated Ringer's solution (LRS), dextrose (D5W), phosphate buffered saline (PBS), Hanks' Balanced Salt Solution (HBSS), and/or isotonic salt solutions. In some embodiments, a sufficient volume of hydration media required to fully hydrate the device to EWC is included in the kit. In some embodiments, the hydration media is stored in a vessel, fluid reservoir, tube, syringe, bag, fluid pump, and/or packet. In some embodiments, the hydration media is sterilized. In some embodiments, the hydration media is buffered at or near physiological pH (e.g., 6.8-7.8).

In some embodiments, the kit is sterile. In some embodiments, the kit is sealed.

In some embodiments, the kit includes instructions for use. In some embodiments, the instructions for use describe a method of treatment described herein.

In some embodiments, the kit comprises packaging. In some embodiments, the packaging comprises a flexible container. In some embodiments, the flexible container comprises flashspun high-density polyethylene fibers. In some embodiments, the packaging comprises a tray into which the device can be positioned for shipment.

Further Definitions

The term medically acceptable refers to a material that is highly purified to be free of contaminants and is nontoxic. The term consists essentially of, as used in the context of a biomaterial or medical device, refers to a material or device that has no more than 3% w/w of other materials or components and said 3% does not make the device unsuited to intended medical uses. Equilibrium water content (EWC) is a term that refers to the water content of a material when the wet weight of the material has become constant, and before the material degrades. In general, materials with a high solids content have been observed to be at equilibrium water content at 24-48 hours. For purposes of measuring EWC, distilled water is used unless otherwise specified.

The term w/v refers to weight per volume e.g., g/L or mg/mL. The terms biomaterial and biomedical material are used interchangeably herein and encompass biomedically acceptable materials directed to a use in the biomedical arts, for example, as implants, catheters, blood-contacting materials, tissue-contacting materials, diagnostic assays, medical kits, tissue sample processing, or other medical purposes. Moreover, while the materials are suited for biomedical uses, they are not limited to the same and may be created as general-purpose materials. A physiological saline refers to a phosphate buffered solution with a pH of 7-7.4 and a human physiological osmolarity at 37° C.

The term molecular weight (MW) is measured in g/mol. The MW of a polymer refers to a weight average MW unless otherwise stated. When the polymer is part of a porous solid, the term MW refers to the polymer before it is crosslinked. When a distance between crosslinks is specified, it is the weight average MW between crosslinks unless otherwise indicated. The abbreviation k stands for thousand, M stands for million, and G stands for billion such that 50 k MW refers to 50,000 MW. Daltons is also a unit of MW and likewise refers to a weight average when used for a polymer.

Publications, journal devices, patents and patent applications referenced herein are hereby incorporated herein for all purposes, with the instant specification controlling in case of conflict. Features of embodiments set forth herein may be mixed and matched as guided by the need to make an operable process or product.

As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition.

As used herein, when a component is referred to as being "adjacent" another component, it can be directly adjacent to (e.g., in contact with) the component, or one or more intervening components also may be present. A component that is "directly adjacent" another component means that no intervening component(s) is present.

A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the self-righting device.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

EXAMPLES

The following examples are intended to illustrate some embodiments described herein, including some aspects of the present invention, but do not exemplify the full scope of the invention.

Example 1: Thrombogenic Evaluation of a PVA Gel

Samples of PVA extrusions were made by heating 200 g distilled water to 95° C. jacketed reaction vessel and allowed to heat to temperature. To this, 40 g of PVA (Sigma, 146k-186k) was added over 5 min time period while mixing at 200 RPM. Polymer was mixed for 1.5 hours at 300 RPM. Polymer was degassed at 90° C. for less than 2 hours. Polymer then extruded into −23° C. ethanol and then stored in ethanol at −25° C. in freezer for 24 hours. Samples were dried for 6 hours.

After drying, samples were submerged in 120° C. glycerol for 17 hours. After annealing, samples removed and allowed to cool before being rinsed with ethanol; cores removed after rinse. Samples dried for 12 hours at 50° C.

Samples of PVA with barium sulfate were made by heating 50 g water in a jacketed reaction vessel at 90° C. In a side vessel, 4 g of barium sulfate and 50 g water homogenized for 15 minutes at 1lk RPM and then added to the jacketed vessel. This was mixed for 10 minutes to heat. After heating, 16 g of PVA (Sigma, 146k-186k) was added and mixed at 360 RPM for approximately 2 hours.

The PVA-RO polymer mixture was heated to 90° C. and extruded into −16° C. ethanol. The extrudate was allowed to dehydrate at −25° C. for 24 hours. Cores were removed and samples dried in an incubator at 50° C. for approximately 6 hours. After drying, samples were submerged in 120° C. glycerol (Sigma) for 17 hours. After annealing, samples removed and allowed to cool before being rinsed with distilled water. Samples dried at 50° C. for 12 hours and packaged for testing.

Samples were evaluated for non-thrombogenic durability testing at Thrombodyne, Inc. (Salt Lake City, UT). Each sample was cut to 15 cm in length with an N=5 per sample group. Prior to testing, samples were sterilized using a 12-hour ethylene oxide exposure; samples were hydra tested for approximately 48 hours in distilled water prior to evaluation to represent clinical use.

Fresh heparinized bovine blood with autologous $^{111}$In-labeled platelets was divided into portions for test sample and control evaluation. Samples were inserted into an in vitro blood flow loop of 0.25 in. ID polyvinyl chloride tubing for approximately 120 minutes. Blood was kept at 98° C. and pumped through the blood loop using a peristaltic pump for the duration of testing. Samples were initially checked for thrombi after 45 minutes in the blood flow loop and removed at 120 minutes. At the end of the experiment, the devices were explanted from the tubing, rinsed with saline, and placed in a gamma counter for thrombus quantification. Experiment parameter are presented in Table 1. Each experiment consisted of an independent flow system per test sample and/or control circulating blood from the same animal to enable simultaneous comparisons without cross-over effects.

Figure 5A:
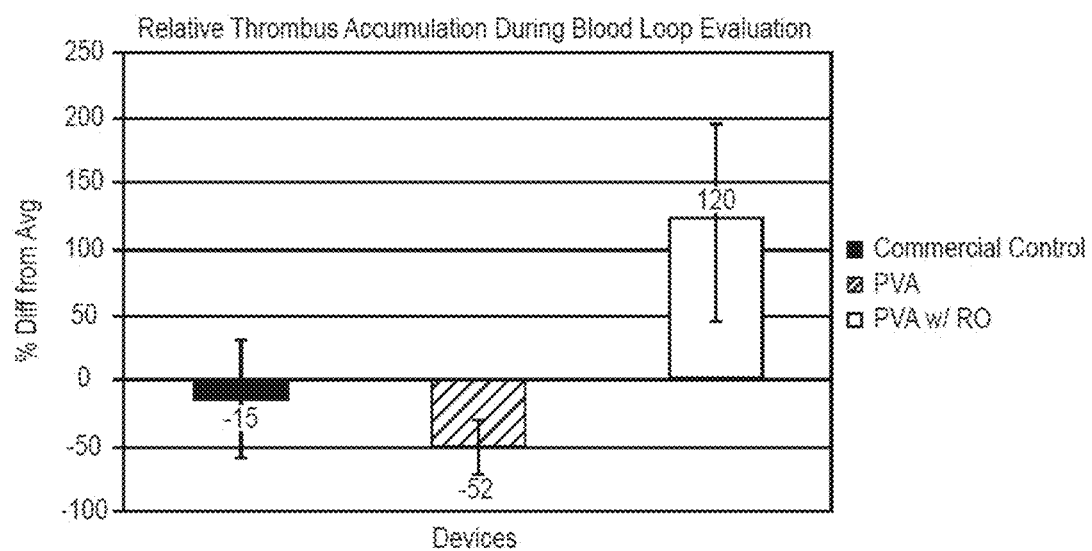
FIGS. 5A-5B provide results of blood contact experiments described in Example 1 as a plot of relative thrombus accumulation (5A) or photographs of the tested samples (5B).
Figure 5B:
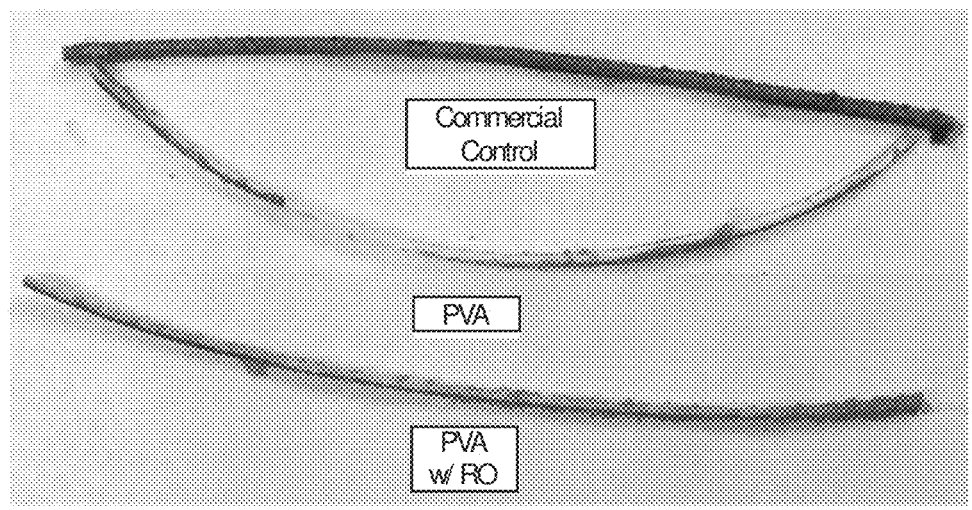

Samples were measured for radioactivity and also qualitatively assessed for specific types of thrombus accumulation (i.e. adhesion or fibrin accumulation). Count results are provided in Table 1. Percent thrombosis was calculated relative to the average total thrombosis observed across all test and control groups per animal blood circulated. Results for thrombus accumulation are provided in Tables 2-3 and depicted in FIG. 5A. Visual assessment of the thrombosis is shown in FIG. 5B, with a commercially available control catheter, a 17% PVA extrusion, and the 17% PVA-barium sulfate extrusion.

TABLE 1

Experimental Parameters

| | |
|---|---|
| Heparin Concentration | 0.75 EU/mL |
| Internal diameter of tubing in which device was deployed | 0.25 in. |
| Blood flow rate | 200 mL/min |
| Experiment time | 60-120 min |
| Number of replications (N)** | 6 |

**Blood from a different animal was used in different replications

TABLE 2

Raw Radiation Data for 6 French Polyurethane Control and Hydrogel Formulations

| Raw Radiation counts per minute (CPM) | Raw Radiation counts per minute (CPM) Polyurethane Control | PVA Formulation | PVA w/ RO (PVA-barium) | Average |
|---|---|---|---|---|
| Expt #1 | 6305 | 8928 | 11509 | 8914 |
| Expt #2 | 9219 | 1803 | 4624 | 5215 |
| Expt #3 | 1194 | 765 | 4101 | 2020 |
| Expt #4 | 8226 | 3095 | 10692 | 7338 |
| Expt #5 | 677 | 2536 | 24837 | 9350 |

TABLE 3

Relative Thrombus Accumulation Based on Percent Difference from Average per Animal

| | % Difference From Average | | |
|---|---|---|---|
| | Polyurethane Control | PVA Formulation | PVA w/ RO (PVA-barium) |
| Expt #1 | −29.27 | 0.16 | 29.11 |
| Expt #2 | 76.77 | −65.43 | 17.71 |
| Expt #3 | −40.89 | −62.13 | 163.87 |
| Expt #4 | 12.11 | −57.82 | 113.99 |
| Expt #5 | −92.76 | −72.88 | 273.46 |
| Mean | −15 | −52 | 120 |
| Std. Error | 44.8 | 20.8 | 74.4 |

The results show a reduction in thrombi for PVA formulation compared to a commercially available PICC. The PVA-RO (barium as RO agent) formulation was not superior to the control. Possible reasons include the lack of barium micronization and evidence of larger barium particles on the surface of the extrusion.

Example 2: Extrudate Hydration Rate

The following example demonstrates the hydration rate for an exemplary extruded PVA tube using 0.039" acetal core filament.

A PVA-Bismuth Subcarbonate polymer solution (e.g., a first water soluble polymer) was prepared using 42.0 g Bismuth Subcarbonate (Lot: Foster, FEI5577), 179.25 g of 6.2 w/w % monobasic sodium phosphate solution, and Poly (vinyl alcohol) 28-99 (lot: EMD, K45556756). Substituents were heated in a sealed polypropylene jar and mixed in a Flaktech Speedmixer.

The polymer was immediately placed on a roller at approximately 70 RPM for 4 hours. When the polymer had cooled to room temperature, it was cut into 1 cm×1 cm×1 cm cubes.

The cubed polymer was extruded using the Brabender ¾" single screw ATR. Heated polymer was extruded into approximately 10° C. ethanol bath onto a 0.039" acetal core filament. The extruded PVA tubes (extrudate) were cut to 24" to 30" segments. After approximately 3 hours of dehydration in ethanol, the core filament was removed and PTFE covered stainless steel mandrels were inserted into lumens.

A hydrophilic solution was prepared using Carbopol 907 (lot: Lubrizol, 010164597), USP water (lot: Fisher, 1607174) and PBS. The solution was heated and mixed until solids fully dissolved.

All samples were soaked for 16 hours at 37° C. in Carbopol 907 solution in stainless steel circulatory baths.

Samples were removed from soak after indicated period and mounted on stainless steel mandrels. Dried samples were then annealed in air at 140° C. for 1.5 hours on mandrels in a forced air oven. Samples were then hydrated in PBS at room temperature (approximately 21° C. for 3 hours). After hydrating, samples were dried back down at 37° C. for 5 hours.

Dry samples were cut into approximately 20 mm long sections. Length, inner diameter, outer diameter, and mass were recorded for each sample. Samples were then submerged in 1×PBS at room temperature (approximately 21-22° C.). A syringe was used to ensure that all air was expelled from lumens.

At various time intervals, samples were removed from PBS, dabbed lightly on a lint-free lab wipe to remove excess PBS from lumen and surface; length and mass were recorded and samples were quickly returned to PBS. Samples were hydrated for a total of 22 hours. Inner and outer diameters were measured again after 1 hour and 22 hours of hydration.

Length, mass and inner diameter (ID)/outer diameter (OD) percent change were calculated using to following formula:

$$\% \text{ change} = \frac{(\text{final value} - \text{initial value})}{\text{initial value}} * 100$$

Percent change for each variable was averaged for each time point (see Table 4).

TABLE 4

| Time (min) | Avg. % Mass Change | Stdev % Mass Change | Avg. % Length Change | Stdev % Length | Avg. % ID Change | Stdev % ID Change | Avg. % OD Change | Stdev % OD Change |
|---|---|---|---|---|---|---|---|---|
| 0 | 0.0 | 0.0 | 0.0 | 0.0 | 0.0 | 0.0 | 0.0 | 0.0 |
| 2.5 | 30.6 | 12.4 | 2.9 | 0.3 | x | x | x | x |
| 5 | 32.4 | 11.3 | 4.5 | 0.6 | x | x | x | x |
| 10 | 30.5 | 4.1 | 6.3 | 1.0 | x | x | x | x |
| 15 | 26.2 | 4.9 | 7.9 | 1.1 | x | x | x | x |
| 20 | 22.9 | 11.1 | 7.4 | 1.0 | x | x | x | x |
| 25 | 35.5 | 10.5 | 6.6 | 0.8 | x | x | x | x |
| 35 | 31.7 | 13.0 | 7.0 | 1.1 | x | x | x | x |
| 45 | 33.3 | 26.1 | 7.4 | 1.1 | x | x | x | x |
| 60 | 24.4 | 15.5 | 7.3 | 0.5 | 18.0 | 4.2 | 2.7 | 4.8 |
| 120 | 29.5 | 4.6 | 7.5 | 0.9 | x | x | x | x |
| 1320 | 26.4 | 4.3 | 6.8 | 0.3 | 18.8 | 3.5 | 4.9 | 2.2 |

During hydration, percent increase in mass fluctuated slightly between 22.9% to 33.3% over the 22-hour hydration period but showed no significant difference in mass increase between any time point.

Percent increase of sample length showed tight standard deviations as compared to mass increase and serve as a representative indicator of level of sample hydration. Length increased 2.9% and 4.5% after 2.5 and 5 minutes of hydration, respectively; length increase then leveled off at approximately 10 minutes of hydration, with no significant increase in length after that point (see Table 4).

Inner and outer diameter showed 4.9% and 18.8% increase at 60 min and 1320 min, respectively. Without wishing to be bound by theory, the significant difference between ID and OD may be due to the fact that ID shrinkage is restricted by the size of the core diameter during ethanol dehydration, drying and annealing, causing the ID to retain more of its initial sizing, whereas OD is unrestricted during post extrusion processing, and therefore able to swell more when hydrated. OD showed no significant change between 1 and 22 hours of hydration.

4F catheters extruded on 0.039" core filament showed no further length increase after 10 minutes of hydration in 1×PBS at 21° C.

Example 3: Macropore Formation Containing Biologically Active Agent

The following example demonstrates the formation of a device comprising a plurality of pores with a biologically active agent contained therein.
1. A slurry made with Poly(vinyl alcohol) is made with water and a porogen. The porogen may or may not be miscible in water. In some cases, the porogen may be an oversaturated salt solution (e.g., comprising an alkali, alkali earth material and halide, inorganic partially neutralized acid, neutralized organic acid). For example, the porogen may comprise an oil (e.g., having a boiling point over 140° C.). In some cases, the porogen may be soluble in alcohol.
2. The slurry is extruded into a continuous shape and cut to size.
3. The slurry is co-extruded onto a base substrate.
4. The base substrate of 3 can be air, a metallic mesh, metallic tube, thermoplastic polyurethane, thermoplastic elastomer, silicone, polyvinyl alcohol (88%+hydrolyzed), poly(ethylene vinyl acetate), polyvinyl chloride, PETE, PETG, Nylon, or PEEK.
5. The porogen is removed with water, alcohol, and/or a surfactant.
6. The macro-pores are filled with a therapeutic solution comprising a biologically active agent.
7. The device is dried and sterilized.
8. At use, the device is wetted, inserted, and expanded with a pressurized fluid to trigger release of the biologically active agent.

Example 4: Solids Content

The following example demonstrates the release of a biologically active agent from one or more devices, as described herein.

Figure 6:
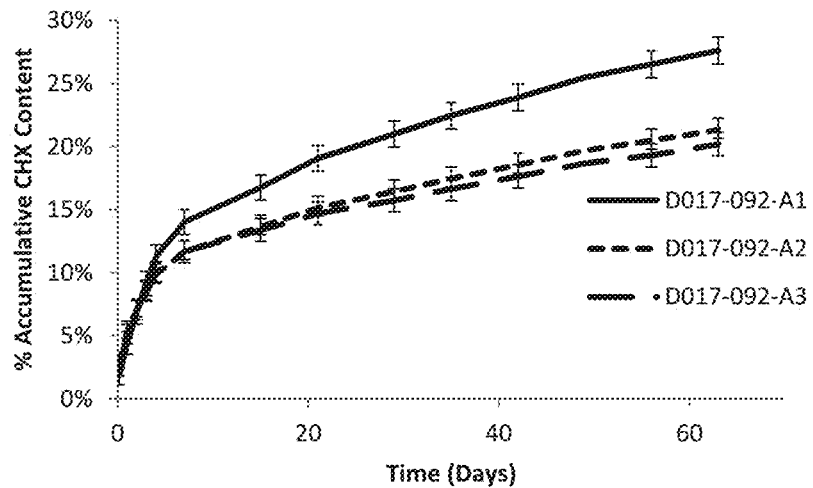
FIG. 6 is a plot of 2.5 w/w % chlorhexidine loading accumulative release profile, according to one set of embodiments.
Figure 7:
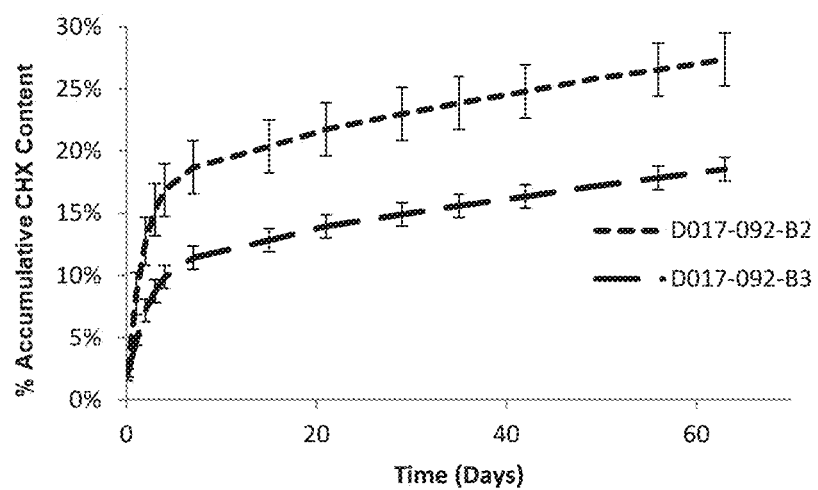
FIG. 7 is a plot of 6.0 w/w % chlorhexidine loading accumulative release profile, according to one set of embodiments.
Figure 11:
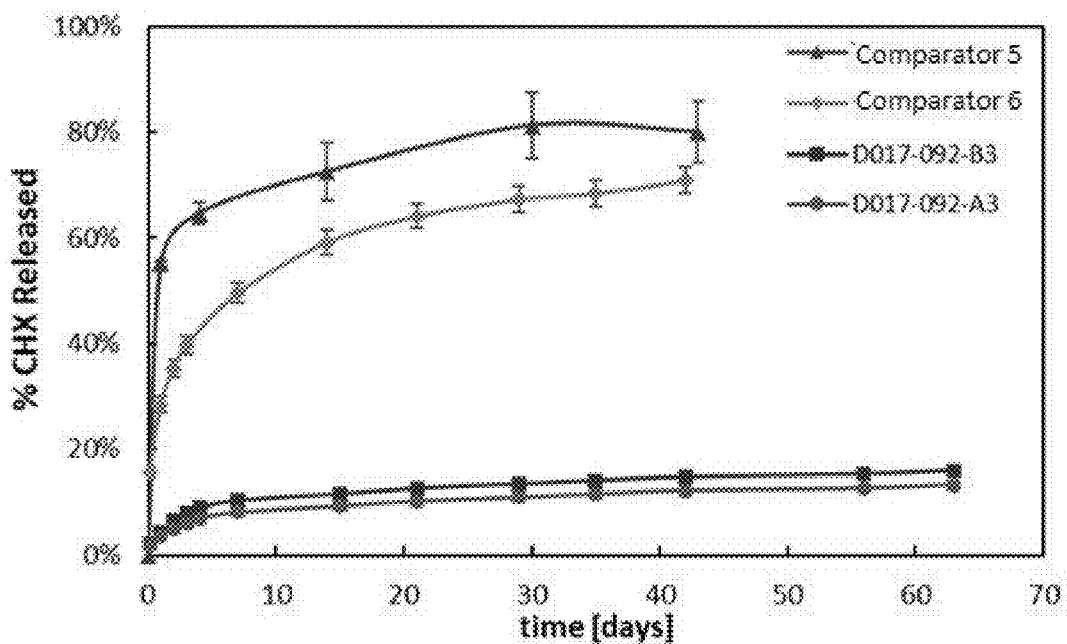
FIG. 11 is a plot of chlorhexidine release over time, according to one set of embodiments.

Chlorhexidine containing PVA material was made using 2.5 w/w % or 6.0 w/w % Chlorhexidine (CHX) free base (EMD Chemicals), a range of 26 w/w %, 30 w/w %, and 33 w/w % of poly(vinyl alcohol) with molecular weight approximately 145 kg/mol (28 cPs @4 w/w %, 99+% hydrolyzed; EMD Chemicals), and ratio of bismuth subcarbonate (Shepard) to PVA of 1 to 2.85. The compounded material was then heated to 95° C. in a ¾" Brabender extruder with a 1:1 compression ratio screw and extruded on an acetal (Dunn Industries) core into 4 Fr tubes with an inner diameter of 0.90 mm. They were then dried and physically crosslinked Table 5 provides the independent variables for FIG. 6 and FIG. 7. With an increase in PVA and bismuth subcarbonate there is a decrease in release rate. This release rate is generally independent of CHX loading. FIG. 11 shows the release of CHX from exemplary devices (D-017-092-B3 and D-017-092-A3) versus a commercially available product (Comparator 6) and an extruded hydrophilic polyurethane (Comparator 5) processed with a CHA-soaking and annealing method (RSM-029-002).

TABLE 5

| | Compositions of PVA/CHX Extrusions | | |
|---|---|---|---|
| | 1 | 2 | 3 |
| A | 2.5 w/w % CHX<br>26 w/w % PVA | 2.5 w/w % CHX<br>30 w/w % PVA | 2.5 w/w % CHX<br>33 w/w % PVA |
| B | N/A | 6.0 w/w % CHX<br>30 w/w % PVA | 6.0 w/w % CHX<br>33 w/w % PVA |

Example 5: Drug Eluting Patch

Figure 8:
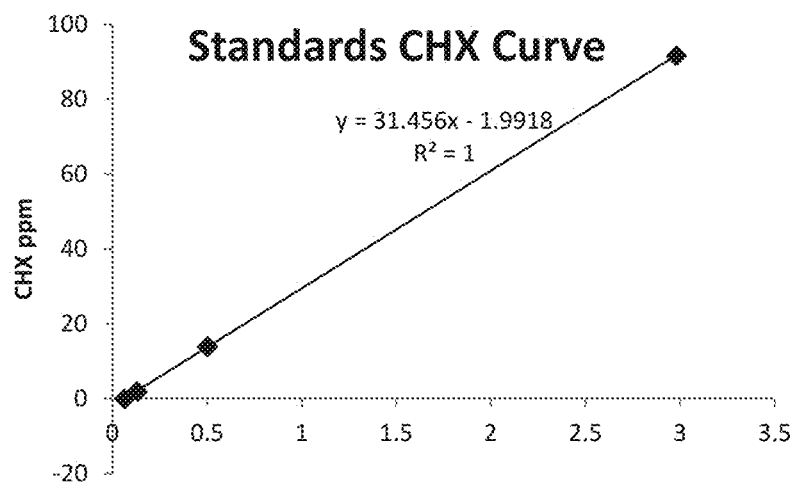
FIG. 8 is a plot of a standard curve for chlorhexidine free base, according to one set of embodiments.

Solution was made with ~600 ppm chlorhexidine free base (CHX) in methanol. CHX/methanol solutions appeared to reach saturation around 1000 ppm. Serial dilutions were made from the solution, where the UV-Vis would become overloaded when concentrations were above 200 ppm. In order to avoid overloading the UV-Vis, concentrations below 100 ppm were used to collect absorbance values. FIG. 8 and Table 6 show the absorbance data collected from the chlorhexidine free base standards.

TABLE 6

Standards for chlorhexidine free base.

| CHX ppm | 91.7  | 13.9  | 1.94  | 0     |
|---------|-------|-------|-------|-------|
| abs     | 2.979 | 0.501 | 0.13  | 0.062 |

To convert the free base version of chlorhexidine to the digluconate version Table 7 and Equation 1 was used. Upon introduction with a salt, chlorhexidine's biguanide groups become protonated.

TABLE 7

Common Chlorhexidine Salts.

| Chlorhexidine salt | Salt Formula | Abbreviation | Molecular Weight | Conversion from CHX (A) |
|---|---|---|---|---|
| Free Base | N/A | CHX | 505.446 g/mol | 1 |
| Dihydrochloride | 2 Cl— | CHH | 578.366 g/mol | 0.87 |
| Diacetate | 2 $CH_3COO$— | CHA | 625.546 g/mol | 0.81 |
| Digluconate | 2 $C_5H_{11}O_5COO$— | CHG | 897.766 g/mol | 0.56 |

To convert mass balances between different salts of chlorhexidine Equation 1 was used, where "A" is the conversion factor.

$$\frac{CHX}{A} = CHX + \text{salt} \qquad (\text{Equation 1})$$

Figure 9:
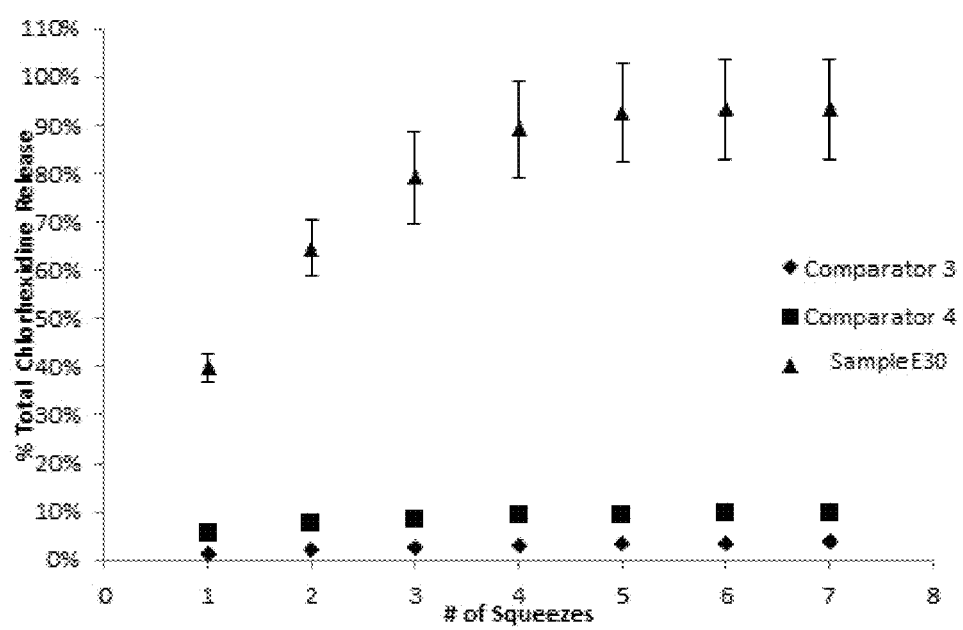
FIG. 9 is a plot of total release of chlorhexidine in 2.21 mL of 0.9% saline per squeeze, according to one set of embodiments.

Upon analysis of Comparator 3, Comparator 4, and an exemplary sample (sample E30), the exemplary sample released 93% of the theoretical dose (2.28% dry) in 0.9% saline, whereas Comparator 3 and Comparator 4 released less than 10% of their total chlorhexidine content as shown in FIG. 9 (Total release of chlorhexidine in 2.21 mL of 0.9% saline per squeeze.) A squeeze represents the saturation and liquid removal of each device.

TABLE 8

Recipe for Sample E30.

| Components | Sample E30 | Syringe # |
|---|---|---|
| 10% PVA Solution (DD017-053-8) | 5.01 g | 1 |
| Glycerol | 1.03 g | 1 |
| 15% Poloxamer 407 Solution (DD017-055-Poloxamer Solution) | 4.07 g | 2 |
| Chlorhexidine Free Base | 0.05 g | 1 |

Figure 10:
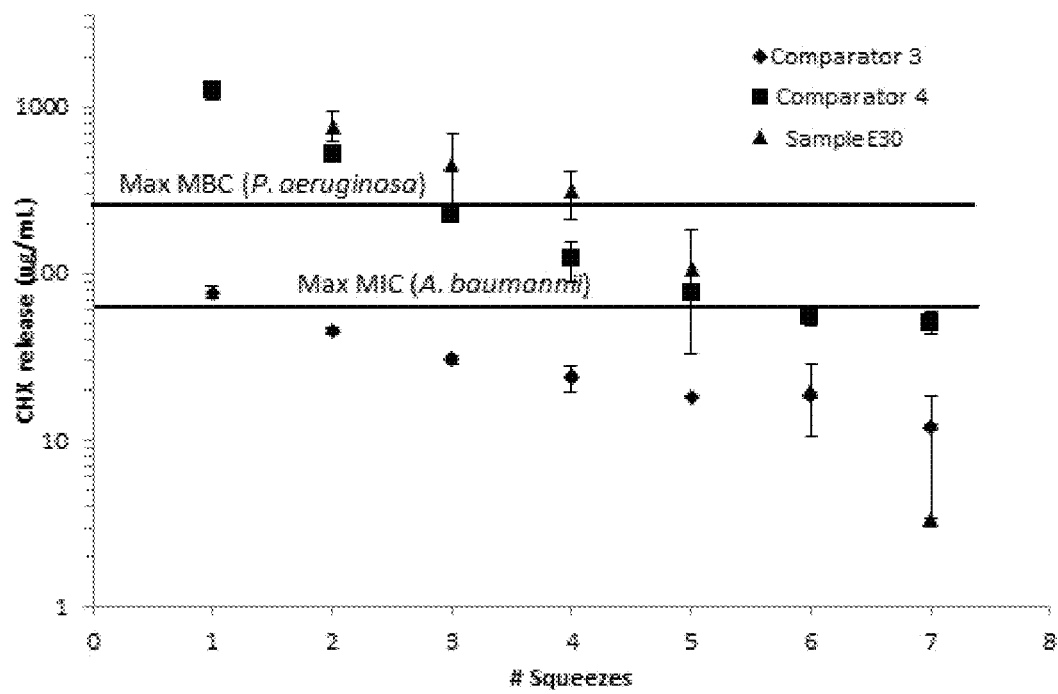
FIG. 10 is a plot of chlorhexidine release versus number of squeezes, according to one set of embodiments.

To determine complete coverage of the common bacteria MBCs and MICs were compared to the (squeeze) release rates of Comparator 3, Comparator 4, and Sample E30. Comparing the maximum MBC (*P. aeruginosa*, 128 µg/mL) to the daily release rate of the squeeze study Comparator 3 is not effective, Comparator 4 was effective for 2-3 days, and Sample E30 was effective for 4-5 days. When preparing the incision site, the physician will typically use PVP-I or ChloraPrep™. Both have at least a 3-log reduction on bacteria and yeast. If the incision site is properly cleaned, inhibition of bacterial and yeast growth is generally only required. Comparing the maximum MIC (*A. baumannii* 64 µg/mL) to the daily release rate of the squeeze study Comparator 3 is effective for 1-2 days, Comparator 4 is effective for 6-7 days and Sample E30 was effective for 5-6 days (FIG. 10). FIG. 10 shows a comparison of saturated release rates of chlorhexidine (normalized to free base salt form) containing foams. The largest known minimum bactericidal concentration (MBC) for chlorhexidine is for *P. aeruginosa* and the largest known minimum inhibitory concentration (MIC) for chlorhexidine is for *A. baumannii*.

Example 6: Bupivacaine Incorporation

The following example demonstrates the release of a biologically active agent from one or more devices, as described herein.

Figure 12:
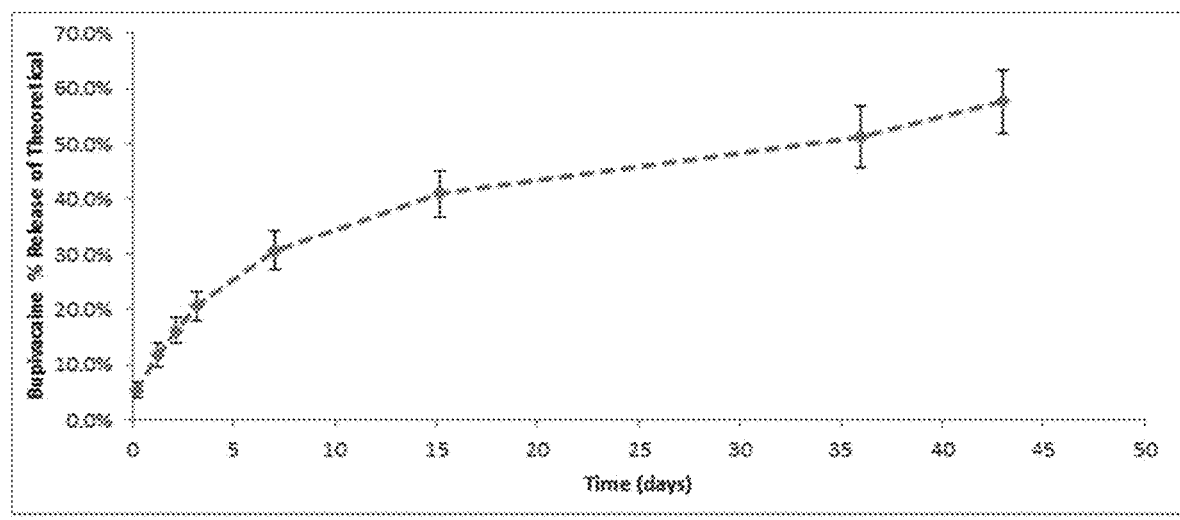
FIG. 12 is a plot of bupivacaine release over time, according to one set of embodiments.

Bupivacaine containing PVA material was made using 1.1 w/w % Bupivacaine (Cayman Chemical), 26 w/w % of poly(vinyl alcohol) with molecular weight approximately 145 kg/mol (28 cPs @ 4 w/w %, 99+% hydrolyzed; EMD Chemicals), and ratio of bismuth subcarbonate (Shepard) to PVA of 1 to 2.85 in an aqueous monosodium phosphate solution 6.3 g/L (Sigma Aldrich). The compounded material was then heated to 95° C. in a ¾" Brabender extruder with a 1:1 compression ratio screw and extruded on an acetal (Dunn Industries) core into 4 Fr tubes with an inner diameter of 0.90 mm. They were then dried and physically cross-linked using a forced air convection oven. A plot of the % release profile of bupivacaine from the test device (DD010-176) is shown in FIG. 12.

Example 7: Zones of Inhibition

The following example demonstrates the presence of a Zone of Inhibition (ZOI) for various organisms in response to an exemplary device as described herein.

This study assessed the antimicrobial activity of two (2) test devices and two (2) control devices against three (3) microbial challenges. *Staphylococcus aureus* (*S. auereus*, MRSA), *Escherichia coli* (*E. coli*), and *Candida albicans* (*C. albicans*) were streaked onto Trypticase Soy Agar (TSA) plated and incubated for approximately 24 hours at 37° C. After incubation, the cultures were harvested individually in sterile PBS using sterile inoculating loops. The concentration of each suspension was adjusted to approximately $1 \times 10^8$ CFU/mL. Serial dilutions of each suspension where prepared to verify inoculum concentration. A series of 1:10 dilutions was prepared on Mueller Hinton (MH) agar using the spread plating technique to verify the concentration of the inoculum used for bacterial lawns. From the adjusted suspensions, two (20 MH agar plates were seeded with each challenge organism to produce a confluent microbial lawn. In each case, a sterile cotton swab was dipped into the adjusted microbial suspension, excess fluid was pressed out of the tip, and the swab was used to streak the surface of the 150 mm MH plates. Each test and control device was applied directly to the surface of the three (3) MH agar plates, each seeded with a separate microorganism. MH Control plates, seeded individually with each of the three (3) microorganisms, were treated with both a tetracycline disc and a sterile blank disc (negative control disc). To assure sterility, 0.1 mL PBS was plated on MH agar using the spread-plate method. All plates were incubated at 37° C. for 24 hours. Zones of Inhibition (ZOI), indicated by the areas of inhibited growth on the plates, were observed under, and measured around, each test device and control in mm. For each control, zones were measured through the diameter of the disc. For each test device, the zones were measured horizontally across the diameter of the cylinder.

The inoculum verification concentrations were calculated to be $1.8 \times 10^8$ CFU/mL for *S. aureus*, $4.1 \times 10^9$ CFU/mL for *E. coli*, and $3 \times 10^6$ CFU/mL for *C. albicans*. Each inoculum produced heavy microbial lawns on the plates. Table 9 indicates the measurements for control and test device ZOI measurements, respectively. Control device PVA/PAA PICC device (with poloxamer) demonstrated no ZOI with any of the challenge organisms tested; growth appeared underneath the test device. Positive Control device (Comparator 7) and two compositions of PVA/PAA tubes with chlorhexidine demonstrated at least 5 mm ZOI for all organisms tested.

TABLE 9

Zone of Inhibition Results

| | Zone of Inhibition [mm] | | | |
|---|---|---|---|---|
| | Control Devices | | Test Devices | |
| Challenge Organism | PVA/PAA PICC device (with poloxamer) | Comparator 7 | PVA/PAA + CHX aged 134 days Lot DD017-095B3 | PVA/PAA + CHA Lot: DD017-167 |
| S. aureus | 0 | 11 | 8 | 11 |
| E. coli | 0 | 8 | 5 | 5 |
| C. albicans | 0 | 8 | 7 | 8 |

Example 8: Multi-Layered Extrusion

The following example illustrates an exemplary process for forming a multi-layered device, as described herein.

Figure 13A:
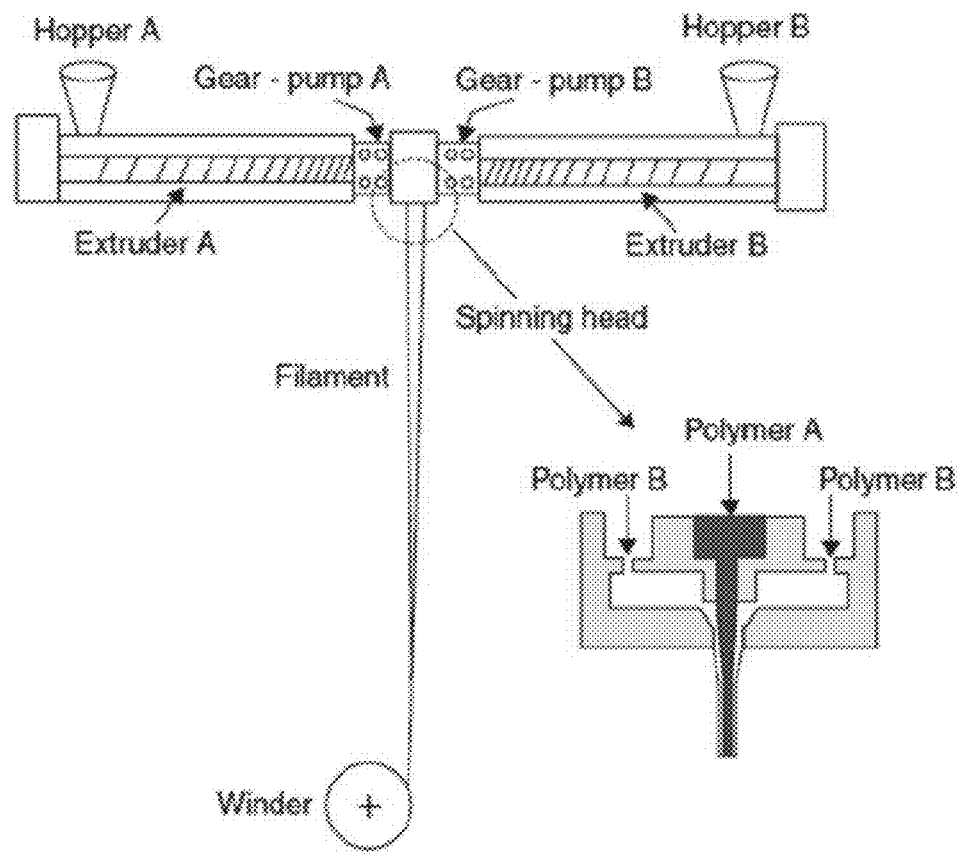
FIG. 13A is a schematic of an exemplary extrusion apparatus to form a device comprising two or more layers of polymeric material, according to one set of embodiments.

A multi-layered extruded tube can be fabricated using established multi-layer thermoplastic extrusion techniques in combination with the forming techniques described herein. Two or more single screw extruders can be connected together with a multilayered extrusion die head. An example of a two-layer system is shown in FIG. 13A. In this example, to design a tube with a drug-eluting lumen and a therapeutic agent-free abluminal surface, Extruder A would process a batched aqueous suspension comprising: PVA, Bismuth Subcarbonate, Monosodium Phosphate, and Chlorhexidine while Extruder B would process a batched aqueous suspension comprising PVA, Bismuth Subcarbonate, and Monosodium Phosphate. The two extrusions would meet in the multi-layer crosshead, with Polymer B forming the outer layer and Polymer A forming the inner layer. A solid, liquid, or gas core could pass through the center of polymer A to form the lumen as described herein. To form a tube with a drug-eluting abluminal surface and a therapeutic agent-free lumen, the inverse process could be designed wherein the Chlorhexidine is added to the Extruder B suspension and not in the Extruder A suspension.

Figure 13B:
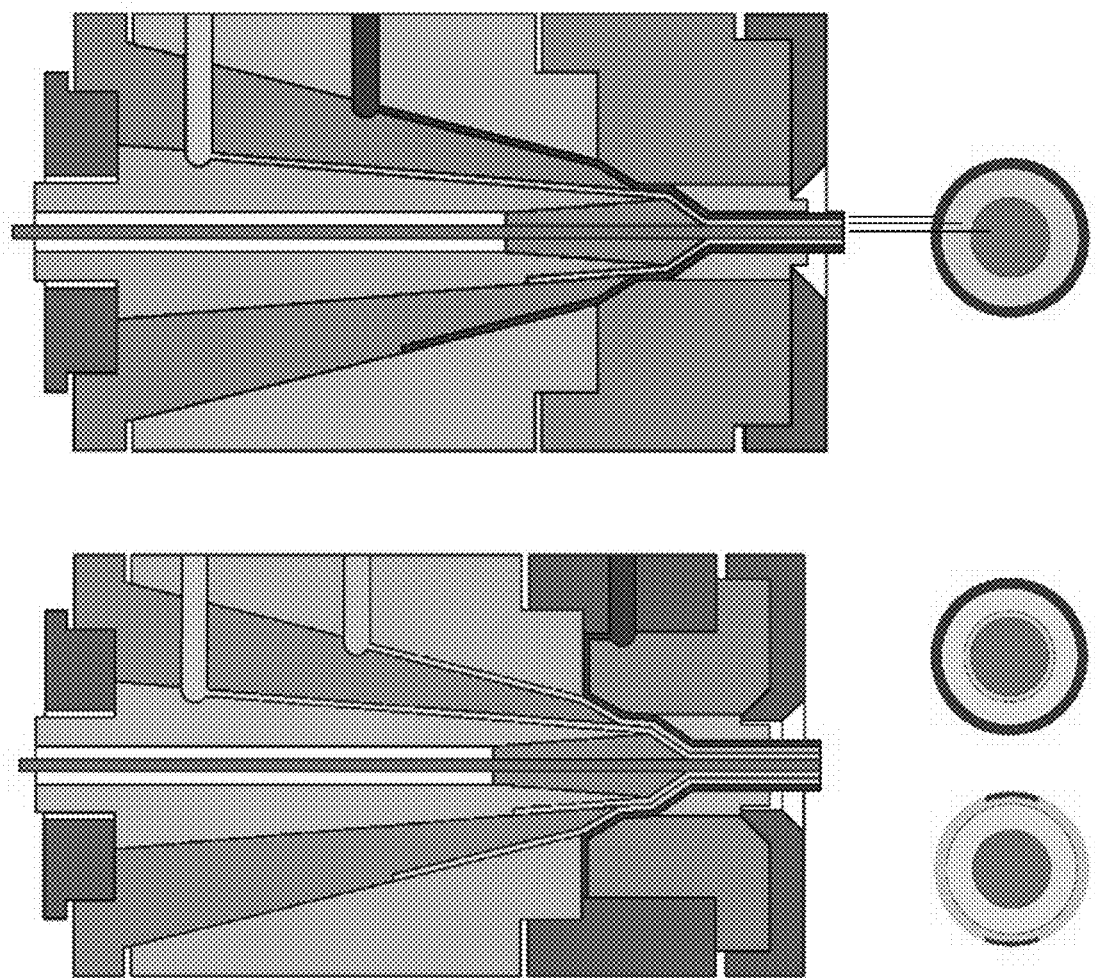
FIG. 13B is a schematic of an exemplary extrusion apparatus to form a device comprising two or more layers of polymeric material, according to one set of embodiments.

An example of a three-layer system is shown in FIG. 13B. In this example, building on the previous one, three separate extruder systems are connected to a single multi-layer crosshead. The layers could interchangeably contain therapeutic agent options (drug 1, drug 2, drug 3, no drug). In one example, a first therapeutic agent (e.g., chlorhexidine) is loaded into the center layer and a second therapeutic agent (e.g., bupivacaine) is loaded into the abluminal surface layer, while the luminal surface contains no therapeutic agent. In this example, a core material (innermost layer) is fed into the crosshead while Extruder A feeds a polymer suspension containing bupivacaine (layer surrounding innermost layer), Extruder B feeds a polymer suspension containing chlorhexidine (peach), and Extruder C feeds a polymer suspension containing no therapeutic agent (outer layer). When the core filament is removed, the results in a tri-layer tube comprising distinct layers of homogenously distributed therapeutic agent(s).

Examples 9: Increases in Inner Diameter and Outer Diameter

The following example demonstrates the increase in inner diameter and outer diameter.

A PVA-Bismuth Subcarbonate polymer solution (e.g., a first water soluble polymer) was prepared using 42.0 g Bismuth Subcarbonate, 179.25 g of 6.2 w/w % monobasic sodium phosphate solution, and Poly (vinyl alcohol) 28-99. Substituents were heated in a sealed polypropylene jar and mixed in a Flaktech Speedmixer.

The polymer was immediately placed on a roller at approximately 70 RPM for 4 hours. When the polymer had cooled to room temperature, it was cut into 1 cm×1 cm×1 cm cubes.

The cubed polymer was extruded using the Brabender ¾" single screw ATR. Heated polymer was extruded into approximately 10° C. ethanol bath onto a 0.039" acetal core filament. The extruded PVA tubes (extrudate) were cut to 24" to 30" segments. After approximately 16 hours of dehydration in ethanol, the core filament was removed and PTFE covered stainless steel mandrels were inserted into lumens and the samples were dried at 95° C. for 3 hours in a forced air convection oven.

A hydrophilic solution was prepared using Carbopol 907, USP water and PBS. The solution was heated and mixed until solids fully dissolved. All samples were soaked for 17 hours at 37° C. in Carbopol 907 solution in stainless steel circulatory baths.

Samples were removed from soak after indicated period and mounted on stainless steel mandrels. Dried samples were then annealed in air at 150° C. for 1.5 hours on mandrels in a forced air oven. Samples were then hydrated in PBS at room temperature (approximately 21° C. for 3 hours). After hydrating, samples were dried back down at 55° C. for 3 hours.

N=24 samples prepared were measured for changes in dimensions by optical microscopy before and after swelling in 1×PBS at 37° C. for two (2) hours. The water content of the was approximately 4-6 w/w % in the "dehydrated" state and ~30-35 w/w % in the EWC state.

Figure 14:
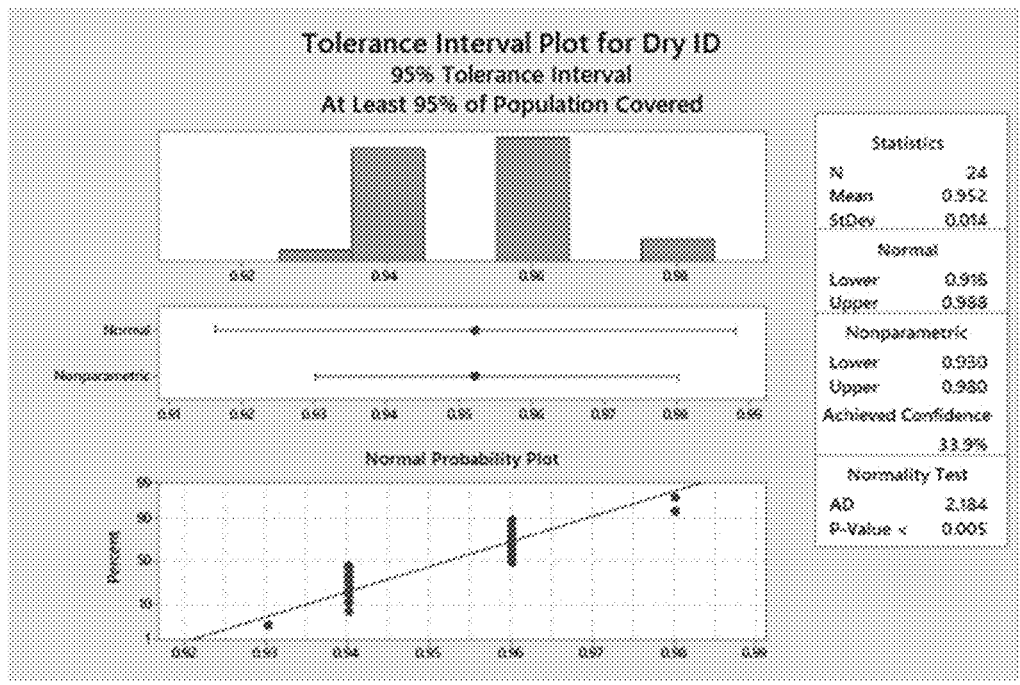
FIG. 14 shows plots of the inner diameter of 24 samples in a dry state in millimeters, according to one set of embodiments.
Figure 15:
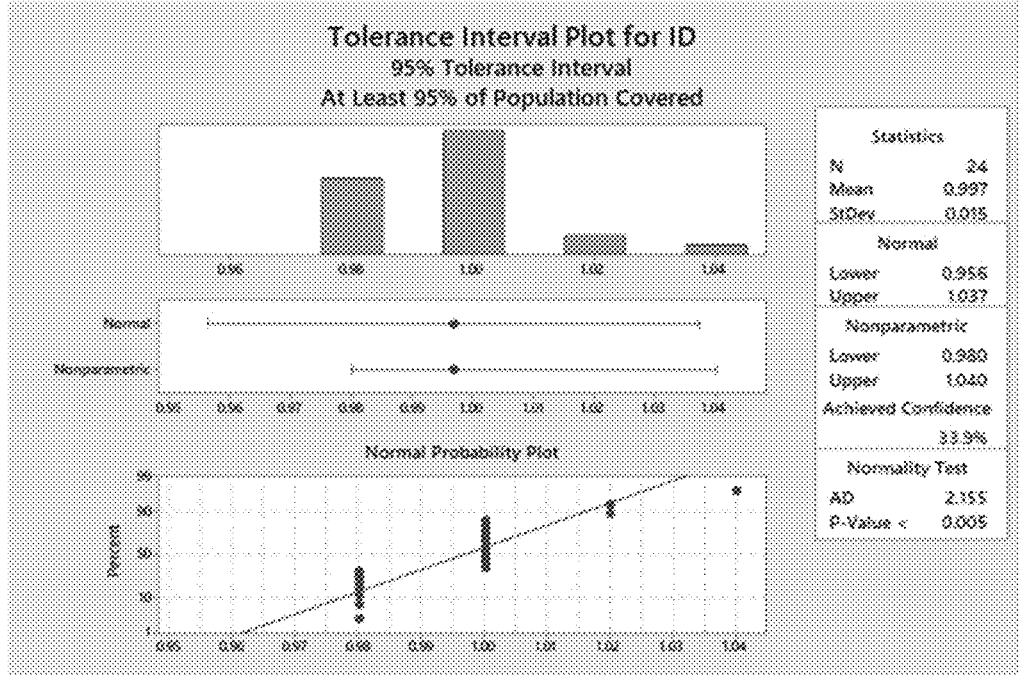
FIG. 15 shows plots of the inner diameter of the 24 samples of FIG. 14 in a swollen state in millimeters, according to one set of embodiments.

FIG. 14 shows the distribution of the inner diameter of the samples in millimeters in a dry state, with an average inner diameter of 0.95 millimeters. FIG. 15 shows the distribution of the inner diameter of the same samples in millimeters in the swollen state, with an average inner diameter of 1.00 millimeters. This demonstrates that the average inner diameter increased from 0.95 millimeters to 1.00 millimeters, which is a 5.3% increase.

Figure 16:
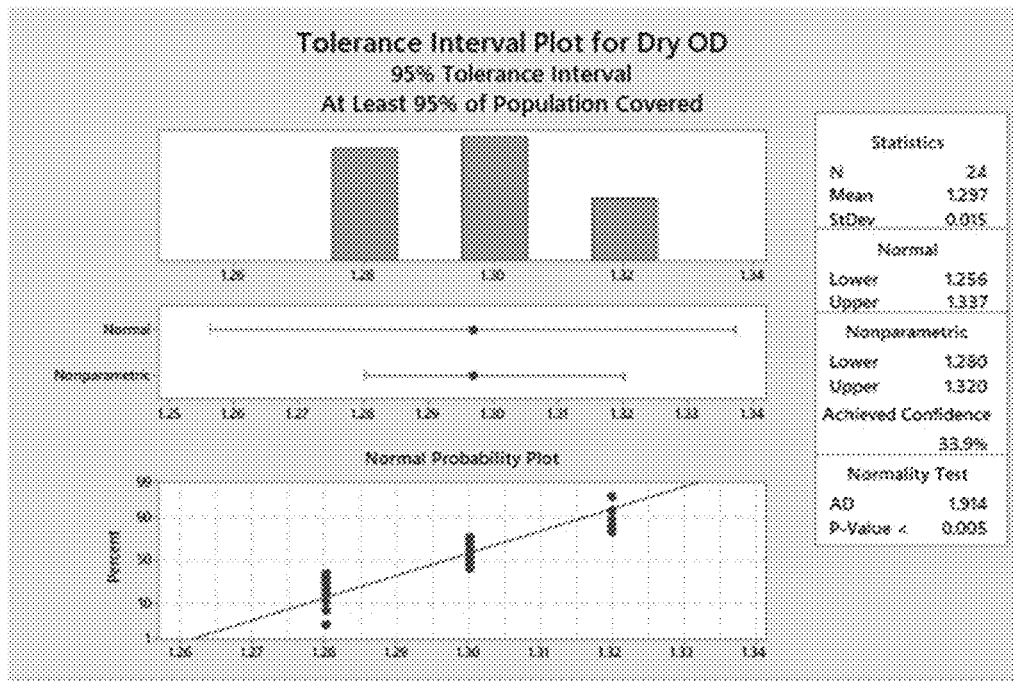
FIG. 16 shows plots of the outer diameter of the 24 samples of FIG. 14 in the dry state in millimeters, according to one set of embodiments.
Figure 17:
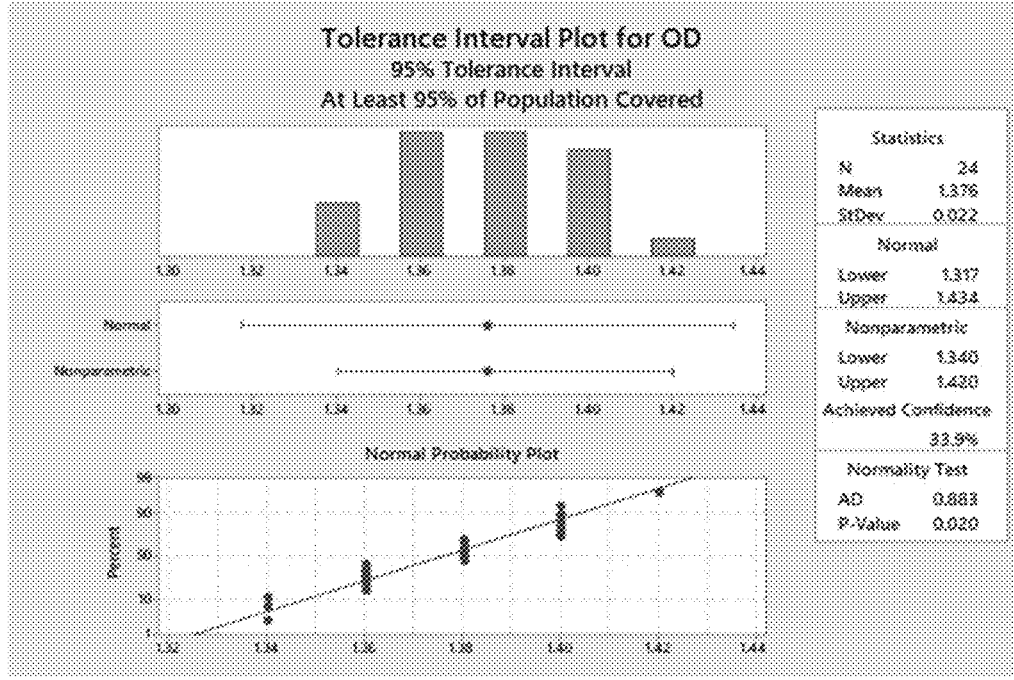
FIG. 17 shows plots of the outer diameter of the 24 samples of FIG. 14 in a swollen in millimeters, according to one set of embodiments.

FIG. 16 shows the distribution of the outer diameter of the same samples in millimeters in the dry state, with an average outer diameter of 1.30 millimeters. FIG. 17 shows the distribution of the outer diameter of the same samples in millimeters in the swollen state, with an average outer diameter of 1.38 millimeters. This demonstrates that the average outer diameter increased from 1.3 millimeters to 1.38 millimeters, which is a 6.2% increase.

Example 10: Mechanical Properties

The following example demonstrates the mechanical properties of PVA/PAA hydrogels.

Uniaxial, constant strain-rate tensile testing was employed to observe the effect of varying temperatures of heat treatment on the mechanical response of the composite PVA/PAA hydrogel. Uniaxial tensile testing of dry and fully hydrated hydrogel tubes was performed with an Instron 3343 tensile testing machine, using a 500N load cell. Tubular samples (N=5 for each sample set) were cut to approximately 50 mm length and extended at a constant crosshead speed of 406.4 mm/min with a 20.3 mm gauge length (corresponding to a constant strain rate of 0.33 s-1). The force-displacement data was converted to engineering stress versus engineering strain using the initial cross-sectional area and gauge length of the test specimen, respectively. Samples defined as "dry" were dehydrated in a forced air convection oven for 3 hours at 55° C., while samples defined as "hydrated" were conditioned in 1×PBS at 37° C. for at least two (2) hours prior to testing. Testing was conducted at ambient conditions with 25 mm wide rubber-coated 1 kN pneumatic grips.

Figure 18:
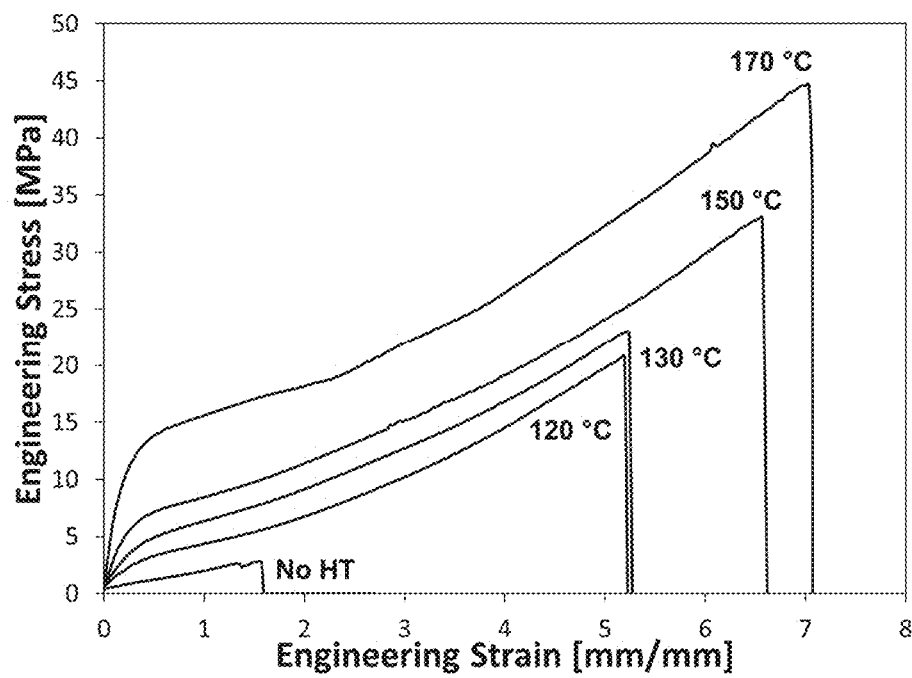
FIG. 18 is a plot of representative stress-strain curves for heat-treated composite PVA/PAA hydrogels, according to one set of embodiments.

FIG. 18 shows representative stress-strain curves for heat-treated composite PVA/PAA hydrogels. As demonstrated in FIG. 18, there was an increase in Young's modulus and yield stress with increasing heat treatment temperature.

Example 11: Swelling Properties

The following example demonstrates the swelling properties of PVA/PAA hydrogels. The swelling of the composite PVA/PAA hydrogels at various heat treatment temperatures were evaluated at 10, 30, 60, 120, 240, and 480 minutes hydration. The swelling of the material from the dry state was done under physiological conditions (in an isotonic salt solution at 37° C.) to evaluate the time it would take for the implanted PVA/PAA hydrogel to reach EWC. Most PVA-based hydrogels require several hours to reach EWC and often exhibit mass swelling of more than 100% from the dry state. The heat-treated composite PVA/PAA hydrogels from this work exhibited a rapid initial swelling and plateau to EWC within approximately 30-60 minutes.

According to the theory of rubber elasticity, the cross-link density of a polymer network is related to the Young's modulus by:

$$E = \frac{3\rho RT}{2M_C} \quad \text{(Equation 2)}$$

Where E is the Young's modulus, p is the density, R is the ideal gas constant, T is the temperature, and Mc is the molecular weight between cross-links. The average molecular weight between cross-links for hydrogels can also be calculated from equilibrium swelling theory. Assuming a Gaussian distribution of cross-linked polymer chains, the Flory and Rehner equation can be used to estimate the average molecular weight between cross-links for a nonionized hydrogel:

$$\frac{1}{\overline{M}_C} = \frac{2}{\overline{M}_n} - \frac{\left(\frac{\overline{v}}{V_1}\right)[\ln(1-V_{2,S}) + V_{2,S} + \chi(V_{2,S})^2]}{(V_{2,S})^{1/3} - \frac{V_{2,S}}{2}} \quad \text{(Equation 3)}$$

Where $\overline{v}$ is the specific volume of the polymer (0.769 cm³/g for 99% hydrolysed PVA), $V_1$ is the molar volume of water (18.1 cm³/mol), $\overline{M}_n$ is the number average molecular weight of the uncross-linked polymer (~145,000 g/mol for 28-99 PVA), $\chi$ is the polymer-solvent interaction parameter (for water-PVA, $\chi$=0.50 at 37° C.), and $V_{2,S}$ is the polymer volume fraction, determined as follows:

$$V_{2,s} = \left[1 + \frac{\rho_p}{\rho_w}\left(\frac{M_S}{M_0} - 1\right)\right]^{-1} \quad \text{(Equation 4)}$$

Where $$\frac{M_S}{M_0}$$

is the mass swelling ratio of the hydrogel at EWC, $\rho_p$ is the polymer density (1.30 g/cm³ for 99% hydrolysed PVA), and $\rho_w$ is the solvent density (1.00 g/cm³ for water). The cross-link density, $\rho_c$, can then be calculated using from $\overline{M}_C$:

$$\rho_c = \frac{1}{v\overline{M}_C} \quad \text{(Equation 5)}$$

Figure 19:
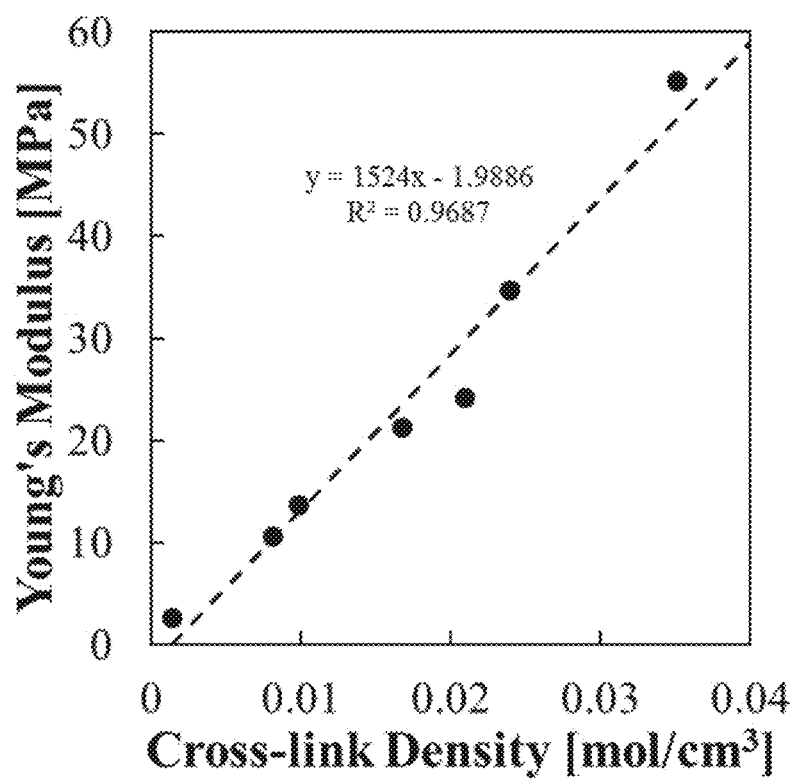
FIG. 19 is a plot of the measured average Young's modulus for each heat treatment group vs. the calculated cross-link density, according to one set of embodiments.

FIG. 19 shows a plot of the measured average Young's modulus for each heat treatment group vs. the calculated cross-link density based on Equation 5. As demonstrated in FIG. 19, there was a strong correlation between the two values ($R^2$=0.9687) indicating that the increase in Young's modulus of the PVA/PAA composite hydrogel was primarily driven by an increase in the physical cross-link density with the temperature of heat treatment.

Figure 20:
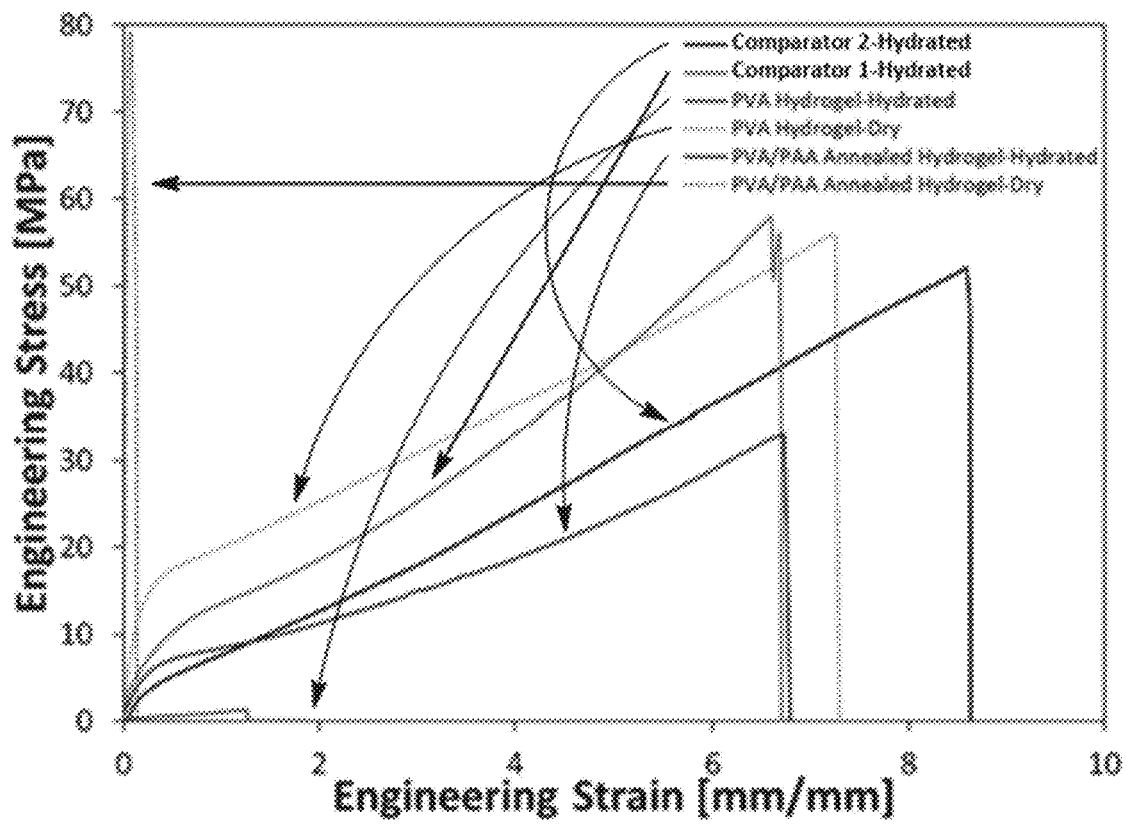
FIG. 20 is a plot of representative stress-strain curves for an untreated composite PVA/PAA hydrogel, a 150° C. heat treated PVA/PAA composite hydrogel, and two conventional TPU's, according to one set of embodiments.

FIG. 20 shows representative stress-strain curves for an untreated composite PVA/PAA hydrogel, a 150° C. heat treated PVA/PAA composite hydrogel, and two conventional TPU's. As demonstrated in FIG. 20, the curve of the hydrated untreated PVA/PAA hydrogel exhibited a Young's modulus, breaking stress, and tensile energy to break (toughness) significantly lower than the control TPU samples. Heat-treatment of the composite PVA/PAA at 150° C. for 90 minutes transitioned the material from a ductile, elastomeric response to a brittle fracture response in the dry state; however, in the hydrated state, the heat-treated hydrogel exhibited comparable mechanical properties to polyurethanes currently used for vascular catheters. The mechanical properties achieved by the 150° C. heat treatment of the PVA/PAA hydrogels in this example were over an order of magnitude improved over comparator high-strength PVA hydrogel materials fabricated by the freeze-thaw method;

the composite hydrogels from this example exhibited a Young's modulus of 24.21±3.98 MPa, compared with less than 1 MPa in the fully hydrated state for comparator PVA hydrogels.

Table 10 shows a summary of the mechanical and swelling properties studied in Examples 10 and 11 of the PVA/PAA hydrogels as a function of the temperature of heat treatment.

TABLE 10

Mechanical and Swelling Properties of PVA/PAA Hydrogels at EWC After Heat Treatment.

| Heat Treatment | Young's Modulus [MPa] | Breaking Stress [MPa] | Strain at Break [mm/mm] | Energy to Break [MJ/m$^3$] | EWC [%] |
|---|---|---|---|---|---|
| No HT | 2.682 ± 0.683 | 4.652 ± 1.160 | 2.601 ± 0.822 | 6.533 ± 2.739 | 155 ± 16 |
| 120° C. | 10.66 ± 1.34 | 21.93 ± 4.12 | 4.790 ± 0.963 | 53.11 ± 16.24 | 62.3 ± 3.3 |
| 130° C. | 13.77 ± 1.32 | 28.48 ± 4.25 | 5.553 ± 0.299 | 76.88 ± 12.47 | 55.4 ± 4.9 |
| 140° C. | 21.32 ± 5.14 | 31.42 ± 5.34 | 6.180 ± 0.793 | 99.23 ± 26.04 | 39.0 ± 3.3 |
| 150° C. | 24.21 ± 3.98 | 24.97 ± 6.02 | 5.544 ± 0.670 | 80.10 ± 23.06 | 33.3 ± 3.0 |
| 160° C. | 34.71 ± 1.71 | 31.38 ± 5.11 | 6.534 ± 0.796 | 117.8 ± 21.4 | 30.1 ± 2.5 |
| 170° C. | 55.27 ± 5.27 | 36.87 ± 6.22 | 6.720 ± 1.103 | 152.63 ± 39.5 | 21.9 ± 1.3 |

Example 12: Resistance of Composite Hydrogel to Thrombotic Occlusion

The following example demonstrates the resistance of the composite hydrogel to thrombotic occlusion. In this example, resistance of samples to thrombotic occlusion was assessed using an established 2-Phase in vitro blood flow loop model. N=6 4F PVA/PAA hydrogel devices were hydrated in sterile saline for approximately 24 hours prior to testing along with TPU samples comprising of comparator devices. Fresh bovine blood was collected by cardiac puncture and heparin was added to achieve a 0.75 U/mL concentration. Catheter samples were inserted into the blood flow loop of ¼ inch (6.4 mm) inner diameter polyvinyl chloride tubing for approximately 120 minutes (Phase 1: Flow). Blood was maintained at 37° C. and continuously metered at 200 mL/min through the loop using a peristaltic pump for the duration of testing to simulate physiological blood flow across the device. Separately, $CaCl_2$ and minimal heparin were mixed into fresh citrated bovine blood and aliquoted into separate vials. After the flow phase, the devices were removed from the heparinized blood circuit and the distal tips of the catheter samples were inserted into the recalcified blood vials and incubated at 37° C. until a clot formed (Phase 2: Stasis). At the end of the clot formation phase, the devices were removed from the vials and gently rinsed with saline to remove any loose blood, taking care not to remove adherent thrombus. To assess luminal patency, a 4-way stopcock was attached to the luer hub of each catheter with a pressure gauge attached to one port and a syringe with saline to the other port; then pressure was applied to the syringe in an attempt to flush the saline through the lumen and the maximum infusion pressure was recorded. The 2-Phase in vitro blood loop model provides a valuable assessment of device resistance to thrombotic occlusion. A qualitatively large amount of thrombus was observed on the tip of every conventional Comparator 1 TPU catheter device, while only a minimal amount of thrombus accumulation was observed on the Comparator 2 catheter and the PVA/PAA composite hydrogel sample tips. One (1) of the PVA/PAA hydrogel samples leaked at the overmolded suture wing junction during the patency check, and was therefore excluded from further analysis.

Figure 21:
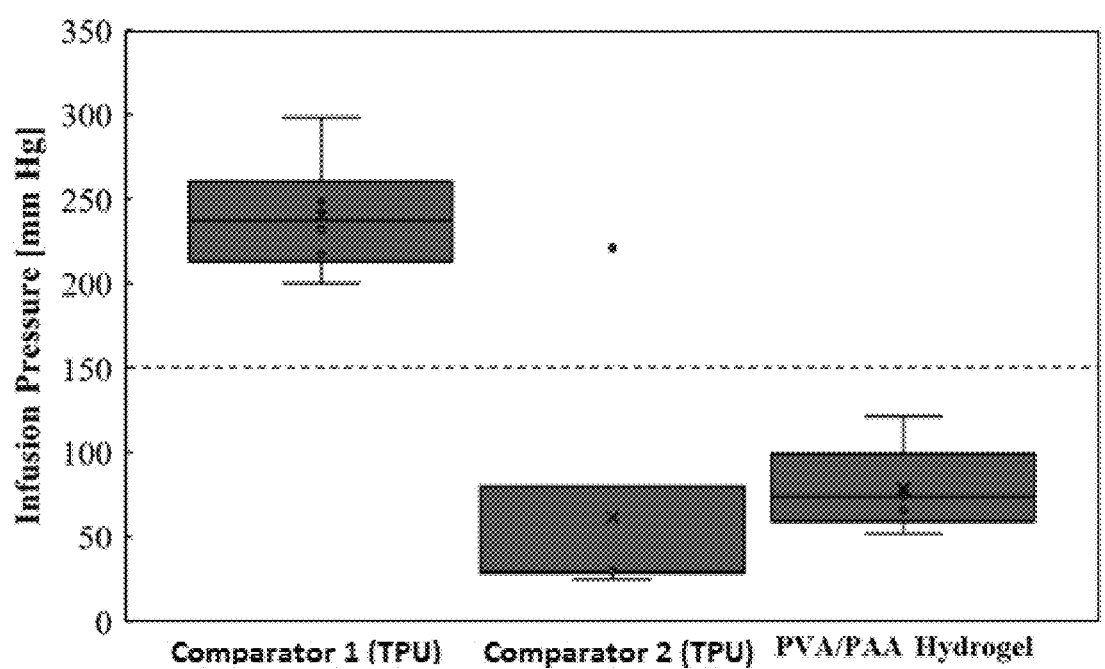
FIG. 21 is a box plot of the mean±standard deviation of the maximum infusion pressure for the TPU control samples as compared with the composite hydrogel device, according to one set of embodiments.

FIG. 21 shows a box plot of the mean±standard deviation of the maximum infusion pressure for the TPU control samples as compared with the composite hydrogel device. As demonstrated in FIG. 21, the composite PVA/PAA hydrogel devices exhibited, on average, 67% lower maximum infusion pressures when compared to conventional TPU. Furthermore, typical pressures for venous infusion devices in adults are <150 mmHg; therefore, a maximum pressure greater than 150 mmHg could be considered occluded. Seven (7) of twelve (12) comparator catheters were characterized occluded, while none (N=0) of the composite PVA/PAA hydrogel devices exhibited a maximum infusion pressure greater than 150 mmHg and were all therefore considered patent.

Example 13: Contact Angle Measurements of Dry and Hydrated PVA-Based Hydrogels

The following example demonstrates contact angle measurements of dry and hydrated PVA-based hydrogels. Contact angle measurements were taken of the PVA tube, the PVA/PAA composite hydrogel, and two comparator catheter bodies. Measurements were taken in both the as-packaged or dehydrated state, and after exposure to 1×PBS at 37° C. for one (1) hour. Contact angle measurements were taken using a custom-built contact angle goniometer by using an Excelis Accu-scope digital camera mounted onto a Unitron Z850 optical stereo microscope at 20× magnification. The contact angles were determined by fitting the profile of at least three (3) droplets using ImageJ software and determining the mean value of the left and right contact angle, totaling six (6) angle measurements per sample group. The initial contact angles were recorded within 10 s after placing droplets of a standard volume of 2 µL onto the hydrogel or polymer surface via pipette.

Figure 22A:
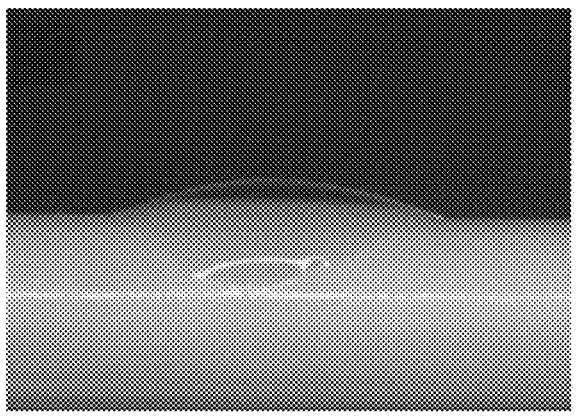
FIG. 22A is a photograph of a 2 microliter (μL) water droplet on a dehydrated PVA/PAA composite hydrogel tube, according to one set of embodiments. The scale bar is 1 mm.
Figure 22B:
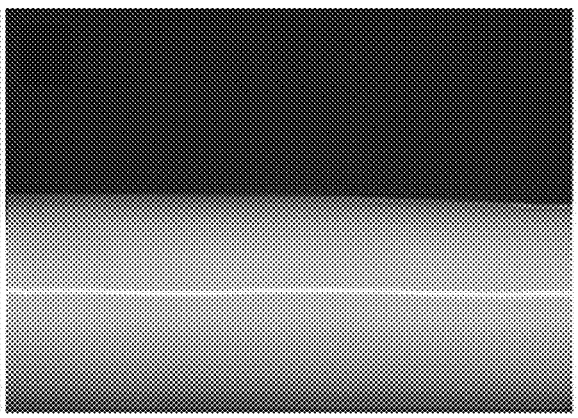
FIG. 22B is a photograph of a 2 microliter (μL) water droplet on a hydrated PVA/PAA composite hydrogel tube, according to one set of embodiments. The scale bar is 1 mm.
Figure 22C:
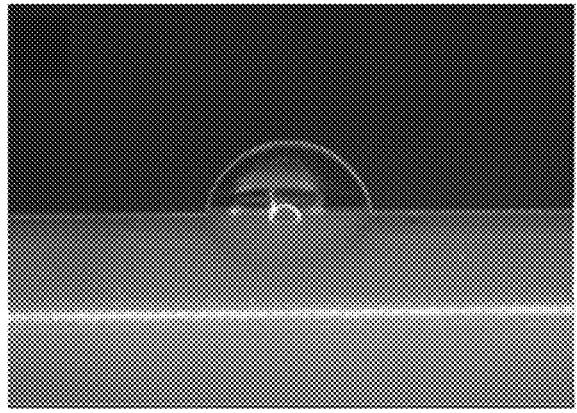
FIG. 22C is a photograph of a 2 microliter (μL) water droplet on a hydrated Comparator 1 TPU tube. The scale bar is 1 mm.
Figure 22D:
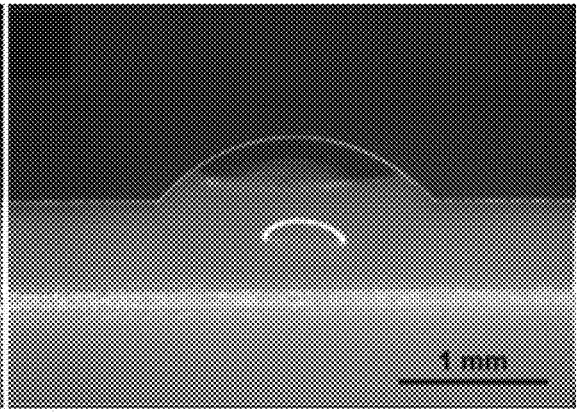
FIG. 22D is a photograph of a 2 microliter (μL) water droplet on a hydrated Comparator 2 TPU tube. The scale bar is 1 mm.

FIG. 22 shows representative optical images of a 2 µL water droplet on dehydrated PVA/PAA composite hydrogel tube (FIG. 22A), hydrated PVA/PAA composite hydrogel tube (FIG. 22B), hydrated Comparator 1 TPU tube (FIG. 22C), and hydrated Comparator 2 TPU tube (FIG. 22D). Scale bar for each image is 1 mm. Table 2 shows the results of the average±standard deviation for each group. As demonstrated in Table 2, contact angles for the commercially available TPUs were both somewhat hydrophobic as packaged (93±7° for Comparator 1 and 99±7° for Comparator 2), compared with the hydrophilic surface of the PVA/PAA hydrogel material in the dehydrated state (17±6°). After hydration, the contact angle of the commercial TPU catheters decreased slightly; however, the PVA/PAA hydrogel material becomes completely wetting.

TABLE 11

Contact Angle Measurements of Dry and Hydrated PVA-Based Hydrogels as Compared with Polyurethane Controls.

| Sample Group | Dry Contact Angle [°] | Hydrated Contact Angle [°] |
|---|---|---|
| PVA Hydrogel | 19 ± 3 | S* |
| PVA/PAA Hydrogel | 17 ± 6 | S* |
| Comparator 1 TPU | 93 ± 7 | 92 ± 6 |
| Comparator 2 TPU | 99 ± 7 | 72 ± 3 |

*S indicates complete wetting

Example 14: Use of Glycerol as a Humectant

The following example demonstrates the use of glycerol as a humectant. The use of glycerol, as opposed to poloxamer, accelerated the initial hydration of the catheter and eliminated the waviness and pig tailing in the first 5 minutes of hydration. The catheters with glycerol continued to grow after 1 hour. The catheters with glycerol matched the 10% poloxamer 407 hydration profile after 60 minutes.

The results of this example indicated that the use of a higher concentration of glycerol increased the hydration speed in the first five minutes of hydration, yet did not improve or reduce speed at which the catheter grew from 5 minutes to 24 hours significantly. The glycerol/poloxamer mixtures showed a reduction in length change from 1 hour to 24 hours as compared to the pure glycerol groups.

It was also discovered that upon exposing a glycerol infused catheter to prolonged heat per accelerated aging protocol and ISTA 2A conditioning the hydration profile changed. Upon the 5-minute mark, pig tailing occurred and no longer met the 5-minute hydration criteria. To address this, a humidity control sponge (Humidichip®, Andersen Products, inc.) was placed in an outer bag with the catheters which were sealed in a Tyvek pouch. At 5 minutes, this group passed the visual and quantitative criteria.

Figure 23:
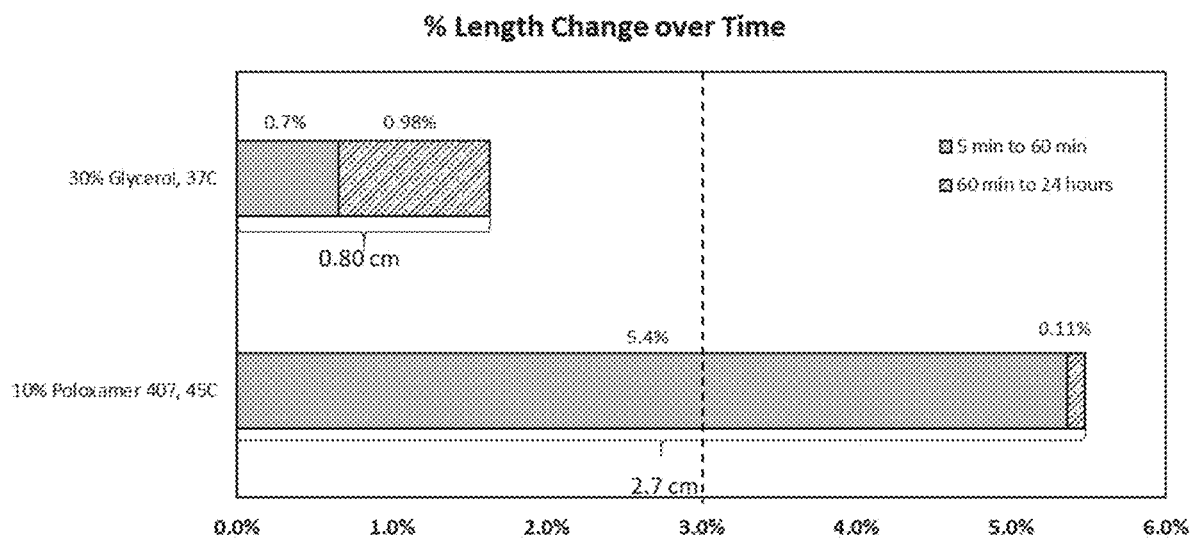
FIG. 23 is a bar graph illustrating the percent length change over time in the 30% glycerol group compared to the 10% poloxamer 407 group, according to one set of embodiments.

FIG. 23 shows a bar graph illustrating the percent length change over time in the 30% glycerol group compared to the 10% poloxamer 407 group. As demonstrated in FIG. 23, it continued to grow significantly after 1 hour.

Figure 24:
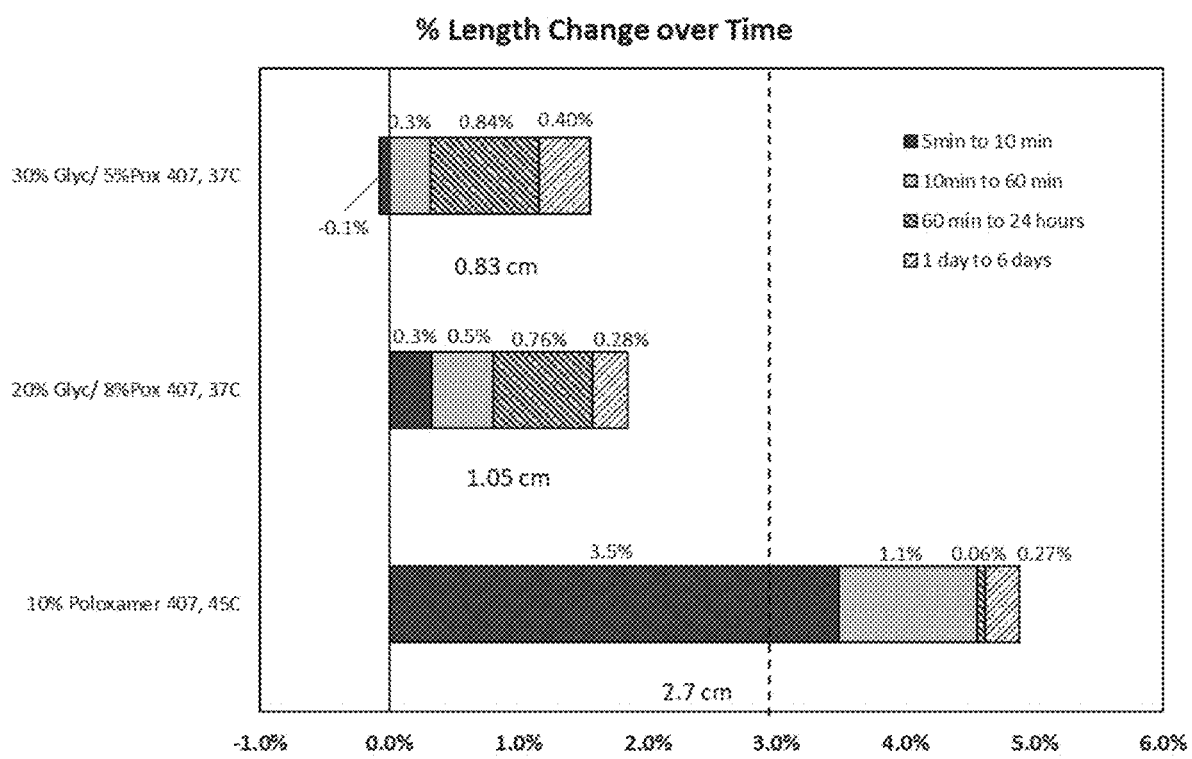
FIG. 24 is a bar graph that shows that an addition of a humidity control sponge in the packaging improved thermal stability by eliminating waviness and pig-tailing by 5 minutes of hydration after exposure to temperature extremes, according to one set of embodiments.

FIG. 24 shows a bar graph that shows that an addition of a humidity control sponge in the packaging improved thermal stability by eliminating waviness and pig-tailing by 5 minutes of hydration after exposure to temperature extremes.

Example 15: Glycerol Removal During Hydration

The following example demonstrates how much glycerol mass was removed from the catheter body during 5 minutes of hydration. Glycerol is a strong humectant and will pull moisture from the ambient environment into a solution with itself. This property made it an ideal material to retain moisture in the catheter body during storage and upon hydration per the PVA/PAA PICC device (with glycerol). Intravenous glycerol is well tolerated and understood, but it was important to evaluate the quantity of glycerol to which a patient would be exposed. A set of six (6) PVA/PAA PICC devices (with glycerol) were used in this example. They were sterilized in Tyvek pouches and packaged in a secondary foil pouch with a humidity control sponge. This method was intended to only remove glycerol through exposure to normal saline, and remove the residual water through oven drying. Due to glycerol's high boiling point and vapor pressure, it was assumed that only a negligible amount would evaporate after exposure to a 55° C. drying temperature, whereas a substantial amount of water would evaporate. Catheter bodies were cut at the suture wing with an indicated length of 55 cm upon hydration.

$$\text{Mobile Water} = \frac{F - D_1}{D_1} \quad \text{(Equation 6)}$$

$$G_5 = \text{Glycerol Removed (5 minutes)} = \frac{D_2 - D_1}{D_2} \quad \text{(Equation 7)}$$

$$G_{48} = \text{Glycerol Removed (48 hours)} = \frac{D_3 - D_1}{D_3} \quad \text{(Equation 8)}$$

$$\text{Total Mobile Mass} = G_{48} + \text{Mobile Water} \quad \text{(Equation 9)}$$

$$\text{Glycerol Remaining (5 minutes)} = G_5 - G_{48} \quad \text{(Equation 10)}$$

$$\Delta G_5 = \text{Mass Glycerol remaining in catheter at 5 minutes} = D_3 - D_2 \quad \text{(Equation 11)}$$

$$\Delta G = \text{Mass of Total Glycerol} = D_3 - D_1 \quad \text{(Equation 12)}$$

Upon removal from the foil pouch and sterile barrier the catheter body contained 11.0 wt %±0.3 wt % mobile mass. The mobile mass was defined as material that can be removed with a fluid. 4.5 wt %±0.3 wt % was determined to be water and 5.6 wt %±0.3 wt % was found to be glycerol. It was understood that the catheter retains water through hydrogen bonding. This bound water was considered permanently bound to the catheter in the conditions seen during shipping, hydration, and in-life use. This bound water began to be removed from the catheter body material at temperatures above 90° C.

After 5 minutes of hydrating in saline, it was determined that the catheter contained 0.6 wt %±0.3 wt % of glycerol and an additional 25 wt %±2 wt % saline in the catheter body at 5 minutes. Of the total amount of glycerol, the catheter body started with 90%±6 wt % was removed in the first 5 minutes.

TABLE 12

Mass Changes of the catheter body

| | Mobile Water (Eq. x) | Glycerol Removed at 5 minutes (Eq. x) | Total Glycerol Removed (Eq. x) | Total Mobile Mass (Eq. x) | Glycerol content at 5 minutes (Eq. x) |
|---|---|---|---|---|---|
| AVG | 4.5% | 5.6% | 6.3% | 11.0% | 0.7% |
| STDEV | 0.3% | 0.7% | 0.5% | 0.3% | 0.4% |

The total content of glycerol per 55 cm segment was found to be 0.030 g±0.002 g. After 5 minutes of hydration the glycerol content was reduced to 0.003 g±0.002 g (3 mg±2 mg). 3 mg±2 mg is considered a safe level for venous exposure.

TABLE 13

| Average mass of catheter bodies at each weight measurement | | | | | | |
|---|---|---|---|---|---|---|
| | Out of Foil | Dry Down 1 | Hydrated 5 min, IFU | Dry Down 2 | Dry Down 3 | Glycerol Mass (Eq. x) | Glycerol Mass remaining in catheter 5 min (Eq. x) |
| AVG | 0.535 g | 0.512 g | 0.67 g | 0.485 g | 0.482 g | 0.030 g | 0.003 g |
| STDEV | 0.006 g | 0.005 g | 0.01 g | 0.006 g | 0.005 g | 0.002 g | 0.002 g |
| Variable | F | $D_1$ | H | $D_2$ | $D_3$ | $\Delta G$ | $\Delta G_5$ |

Since the catheter was dried before hydration in this example, whereas a physician might hydrate upon removal from pouches/kits, the required water to hydrate the catheter was increased. This additional drying step increased the required time when dried down compared to a catheter hydrated directly out of the pouches. For these reasons the extra drying step (Di) was considered the worst-case scenario.

The majority of glycerol was removed from the catheter after 5 minutes of hydration per the IFU. The gravimetric method showed further removal of glycerol between 5 minutes of hydration and 48 hours of hydration in the catheter body (n=6, paired t-test, p=0.007, C.I. 95%). Additionally, the mass of glycerol eluted after 5 minutes of hydration was measured; from as-packaged to 5 minutes in saline (per IFU), the catheter gained 31±2 wt % of saline and lost 5.6±0.7 wt % of glycerol. The net mass gain after 5 minutes of hydration was 25±2 wt % from removal out of the pouches.

Exemplary Embodiments

1. A process for making a hydrophilic porous solid comprising heating a mixture that comprises at least one water soluble polymer, a solvent, and at least one therapeutic agent to a temperature above the melting point of the polymer/solvent mixture, and passing the mixture into a solvent-removing environment.
2. The process of paragraph 1 wherein the forming of the mixture comprises extrusion of the mixture through a die, molding, casting, or thermal forming.
3. The process of paragraph 1 wherein the forming of the mixture comprises extrusion of the mixture through a die, the mixture is never heated above a boiling point of the mixture, and the mixture is formed at temperatures below a melting point of the polymer/solvent mixture.
4. The process of paragraph 1 wherein the forming of the mixture comprises extrusion of the mixture through a die and further comprising a core that passes through the die, with the porous solid being formed around the core.
5. The process of paragraph 1 with the porous solid being a hydrophilic nanoporous solid wherein pores of the solid have a size of 100 nm or less.
6. The process of paragraph 5 wherein the porous solid has a Young's modulus of at least 5 MPa at EWC of the porous solid.
7. The process of paragraph 1 with the porous solid being a hydrophilic microporous solid comprising pores of more than 100 nm in diameter and wherein pores of the solid have a size of 1 μm or less.
8. The process of paragraph 1 wherein the at least one polymer comprises poly(vinyl alcohol), poly(acrylic acid), polyethylene glycol, or poly(vinyl pyrrolidone), polyalkyleneimine, polyacrylamide, hydroxypropyl methacrylamide, polyoxazoline, polyphosphate, polyphosphazene, hyaluronic acid, chitosan, or polysaccharide.
9. The process of paragraph 1 wherein the at least one polymer comprises a first polymer at a first concentration and a second polymer at a second concentration, with the first concentration being from 10%-60% w/w and the second polymer being from 1%-10% w/w, with the w/w being the weight of the polymer relative to the total weight of all of the polymers and the solvent in the mixture.
10. The process of paragraph 1 further comprising a radiopaque agent in the polymer mixture.
11. The process of paragraph 1 being performed without covalent crosslinking of the at least one water soluble polymer.
12. The process of paragraph 1 wherein the porous solid has an aspect ratio of at least 10:1.
13. A medical device (or catheter) for vascular access that comprises a porous dehydrated physically crosslinked synthetic hydrophilic polymer hydrogel having a Young's modulus of at least 5 MPa, at equilibrium water content (EWC) of the solid further comprising a therapeutic agent dispersed through the hydrogel for sustained release through the lumenal or ablumenal surface to the blood stream (or targeted location) in an effective amount over a period of at least about 1 day, with the hydrogel having a water content of at least about 10% by weight or volume when allowed to fully hydrate.
14. The catheter of paragraph 13 with being a hydrophilic nanoporous solid wherein pores of the solid have a size of 100 nm or less.
15. The catheter of paragraph 13 wherein the porous solid comprises at least one polymer, with at least 50% w/w of the at least one polymer being poly(vinyl alcohol) (PVA).
16. The catheter of paragraph 13 wherein the catheter comprises the porous solid with a lumen and is a central venous catheter, a peripherally inserted central catheter (PICC), a tunneled catheter, a dialysis catheter, a central venous catheter, a peripheral central catheter, a midline catheter, a peripheral catheter, a tunneled catheter, a dialysis access catheter, an urinary catheter, a neurological catheter, a peritoneal catheter, an intra-aortic balloon pump catheter, a diagnostic catheter, an interventional catheter, a vascular access port, or a drug delivery catheter.
17. A device comprising a body portion, wherein the body portion is formed of a polymeric material comprising a first water soluble polymer and a biologically active agent associated with the polymeric material, wherein the biologically active agent is distributed within the polymeric material substantially homogeneously, and wherein the device has an elongation at break of greater than or equal to 50% and/or the device has an increase in overall length in an equilibrium water content state of greater than or equal to 1% as compared to an overall length in a dehydrated state.
18. A device comprising a body portion, wherein the body portion is formed of a polymeric material comprising a first water soluble polymer, and wherein the body portion comprises a plurality of pores, a second water soluble polymer positioned within at least a portion of the plurality of pores of the body portion, and a biologically active agent associated with the first water soluble polymer and/or the second water soluble polymer, wherein the biologically active agent is distributed within the first water soluble polymer substantially homogeneously.

19. A device as in paragraph 17 or 18, wherein the device is substantially non-thrombogenic.

20. A device comprising a body portion, wherein the body portion is formed of a polymeric material comprising a first water soluble polymer and a biologically active agent associated with the polymeric material, wherein the biologically active agent is distributed within the polymeric material substantially homogeneously, and wherein the polymeric material has a Young's elastic modulus of greater than or equal to 500 MPa in a dehydrated state and a Young's elastic modulus of less than or equal to 300 MPa and greater than or equal to 5 MPa at an equilibrium water content state.

21. A device comprising a body portion, wherein the body portion is formed of a polymeric material comprising a first water soluble polymer, a biologically active agent associated with the polymeric material, wherein the biologically active agent is distributed within the polymeric material substantially homogeneously, wherein the polymeric material has a water content of less than 5 w/w % and greater than or equal to 0.1 w/w % in a dehydrated state, and wherein the polymeric material is configured to swell in an amount greater than or equal to 5 w/w % and less than or equal to 50 w/w % from a dehydrated state to an equilibrium water content state in less than or equal to 60 minutes (e.g., less than or equal to 10 minutes, less than or equal to 5 minutes, less than or equal to 1 minute, or less than or equal to 10 seconds) at 25° C.

22. A device comprising a body portion, wherein the body portion is formed of a polymeric material comprising a water-soluble polymer and a biologically active agent associated with the polymeric material, wherein the biologically active agent is present in the device in an amount of greater than or equal to 0.01 w/w % versus the total weight of the device in a dehydrated state, and wherein the polymeric material has a Young's elastic modulus of greater than or equal to 500 MPa in the dehydrated state and a Young's elastic modulus of less than or equal to 300 MPa and greater than or equal to 5 MPa at an equilibrium water content state.

23. A device comprising a body portion, wherein the body portion is formed of a polymeric material comprising a first water soluble polymer and a biologically active agent associated with the polymeric material, wherein the biologically active agent is distributed within the polymeric material substantially homogeneously, and wherein the biologically active agent is configured to be released from the polymeric material at a first average rate as determined at 24 hours of release and at a second average rate of at least about 1% of the first average rate after 30 days.

24. A catheter configured for administration to a subject, comprising a body portion, wherein the body portion is formed of a polymeric material comprising a first water soluble polymer and a biologically active agent distributed within the polymeric material substantially homogeneously.

25. A catheter configured for administration to a subject, comprising a body portion, wherein the body portion is formed of a polymeric material comprising a first water soluble polymer and a biologically active agent distributed within the bulk of the polymeric material, wherein the biologically active agent is present in the catheter in an amount of 0.01 wt % versus the total catheter weight in a dehydrated state.

26. A method for forming a device, comprising, with a mixture comprising a first water soluble polymer and a salt, wherein the first water soluble polymer is present in the mixture in an amount greater than or equal to 13 w/w % versus the total weight of the mixture, performing the steps of extruding the mixture at a temperature greater than or equal to 65° C. on a core material to form a polymeric material disposed on the core material, exposing the polymeric material to a non-solvent of the polymeric material at a temperature less than or equal to 28° C. for greater than or equal to 15 minutes, introducing, to the polymeric material, a solution comprising a biologically active agent, heating the polymeric material and the solution to a temperature of greater than or equal to 30° C., flowing the solution adjacent the polymeric material, and drying the polymeric material, wherein the biologically active agent is distributed within the polymeric material substantially homogeneously to within less than or equal to 50% of an average loading of the biologically active agent in the polymeric material.

27. A method as in paragraph 26, wherein the solution comprises a second water soluble polymer, same or different than the first water soluble polymer.

28. A method as in any preceding paragraph, wherein a second solution comprises a second water soluble polymer, same or different than the first water soluble polymer is flowed adjacent to the polymeric material for greater than or equal to 1 hour.

29. A method as in any preceding paragraph, comprising annealing the polymeric material to a temperature of greater than or equal to 100° C. at atmospheric pressure for greater than or equal to 30 minutes.

30. A method as in any preceding paragraph, wherein the core material is a gas.

31. A method, comprising administering, into an external orifice of a subject, a device comprising a body portion, wherein the body portion comprises a polymeric material comprising a water-soluble polymer and a biologically active agent associated with the polymeric material, the device having an aspect ratio of greater than or equal to 3:1, wherein the biologically active agent is distributed within the polymeric material substantially homogeneously.

32. A method as in paragraph 31, wherein the polymeric material is substantially non-thrombogenic, 33. A method as in any preceding paragraph, wherein the biologically active agent is present in the device in an amount of greater than or equal to 0.01 w/w % versus the total weight of the device.

34. A method as in any preceding paragraph, wherein the polymeric material has a water content of less than 5 w/w % and greater than or equal to 0.1 w/w % in the dehydrated state, and wherein the polymeric material is configured to swell in an amount greater than or equal to 5 w/w % and less than or equal to 50 w/w % from a dehydrated state to an equilibrium water content state in less than or equal to 60 minutes (e.g., less than or equal to 10 minutes, less than or equal to 5 minutes, less than or equal to 1 minute, or less than or equal to 10 seconds).

35. A device as in any preceding paragraph, wherein the polymeric material comprising a first water soluble polymer having a plurality of pores and further comprising a second water soluble polymer, same or different than the first water soluble polymer and positioned within at least a portion of the plurality of pores.

36. A device as in any preceding paragraph, wherein the polymeric material has a Young's elastic modulus of greater than or equal to 500 MPa in a dehydrated state and a Young's elastic modulus of less than or equal to 300 MPa and greater than or equal to 5 MPa at an equilibrium water content state.

37. A device as in any preceding paragraph, wherein the polymeric material has a water content of less than 5 w/w % and greater than or equal to 0.1 w/w % in a dehydrated state and wherein the polymeric material is configured to swell in an amount greater than or equal to 5 w/w % and less than or equal to 50 w/w % from a dehydrated state to an equilibrium water content state in less than or equal to 60 minutes (e.g., less than or equal to 10 minutes, less than or equal to 5 minutes, less than or equal to 1 minute, or less than or equal to 10 seconds) at 25° C.

38. A device as in any preceding paragraph, wherein the plurality of pores have a mean pore size of less than or equal to 500 nm and greater than or equal to 10 nm.

39. A device as in any preceding paragraph, wherein at least 50% of the plurality of pores have a diameter of less than or equal to 1 am.

40. A device as in any preceding paragraph, wherein the device is configured to swell in an amount greater than or equal to 5 w/w % and less than or equal to 50 w/w % from a dehydrated state to an equilibrium water content state.

41. A device as in any preceding paragraph, wherein the device has a coefficient of friction of less than or equal to 0.10 at an equilibrium water content state.

42. A device as in any preceding paragraph, wherein the device comprises an osmotic agent present in the polymeric material in an amount greater than or equal to 0.05 w/w % and less than or equal to 2 w/w % versus the total device weight.

43. A device as in any preceding paragraph, wherein the osmotic agent is selected from the group consisting of phosphates, borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

44. A device as in any preceding paragraph, wherein the polymeric material has a water contact angle of less than or equal to 45 degrees at an equilibrium water content state.

45. A device as in any preceding paragraph, wherein the first water soluble polymer does not comprise covalent cross-linking agents.

46. A device as in any preceding paragraph, wherein the first water soluble polymer is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl)methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

47. A device as in any preceding paragraph, wherein the second water soluble polymer is selected from the group consisting of poly(vinyl alcohol), poly(acrylic acid), polyethylene glycol, or poly(vinyl pyrrolidone), poly(methacrylic sulfobetaine), poly(acrylic sulfobetaine), poly(methacrylic carboxybetaine), poly(acrylic carboxybetaine), povidone polyacrylamide, poly(N-(2-hydroxypropyl)methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

48. A device as in any preceding paragraph, wherein the device is configured for use with a medical device such as a catheter, a balloon, a shunt, a wound drain, an infusion port, a drug delivery device, a tube, a contraceptive device, a feminine hygiene device, an endoscope, a grafts, a pacemaker, an implantable cardioverter-defibrillator, a cardiac resynchronization device, a cardiovascular device lead, a ventricular assist device, an endotracheal tube, a tracheostomy tube, an implantable sensor, a ventilator pump, and an ophthalmic device.

49. A device as in paragraph 48, wherein the catheter is selected from the group consisting of central venous catheters, peripheral central catheters, midline catheters, peripheral catheters, tunneled catheters, dialysis access catheters, urinary catheters, neurological catheters, percutaneous transluminal angioplasty catheters, and peritoneal catheters.

50. A device as in any preceding paragraph, wherein the second water soluble polymer is positioned within the bulk of the first water soluble polymer.

51. A device as in any preceding paragraph, wherein less than 0.5 w/w % sorption of a therapeutic agent to the bulk of the first water-soluble polymer occurs at equilibrium water content after flushing with 5× the volume of the device with water or normal saline.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, device, material, kit, and/or method described herein. In addition, any combination of two or more such features, systems, devices, materials, kits, and/or methods, if such features, systems, devices, materials, kits, and/or methods are not mutually inconsistent, is included within the scope of the present invention.

The indefinite devices "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer to, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more devices, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated device that would described herein as being "square" would not require such device to have faces or sides that are perfectly planar or linear and that intersect at angles of exactly 90 degrees (indeed, such A device can only exist as a mathematical abstraction), but rather, the shape of such device should be interpreted as approximating a "square," as defined mathematically, to an extent typically achievable and achieved for the recited fabrication technique as would be understood by those skilled in the art or as specifically described. As another example, two or more fabricated devices that would described herein as being "aligned" would not require such devices to have faces or sides that are perfectly aligned (indeed, such A device can only exist as a mathematical abstraction), but rather, the arrangement of such devices should be interpreted as approximating "aligned," as defined mathematically, to an extent typically achievable and achieved for the recited fabrication technique as would be understood by those skilled in the art or as specifically described.

What is claimed is:

1. A device, comprising:
   a body portion, wherein the body portion is formed of a polymeric material comprising a first water soluble polymer, and wherein the body portion comprises a plurality of pores;
   a second water soluble polymer positioned within at least a portion of the plurality of pores of the body portion; and
   a biologically active agent associated with the first water soluble polymer and/or the second water soluble polymer,
   wherein the biologically active agent is distributed within the first water soluble polymer substantially homogeneously.

2. The device claim 1, wherein the polymeric material is configured to swell in an amount greater than or equal to 5 w/w % to an equilibrium water content state.

3. The device claim 1, wherein the polymeric material is configured to swell to an equilibrium water content state in a time period of less than or equal to 60 minutes at 25° C.

4. The device of claim 1, wherein the device comprises a humectant.

5. The device of claim 1, wherein the body portion has an inner diameter, an outer diameter, and a length; and wherein the polymeric material is configured to swell such that the inner diameter and/or the outer diameter increase by a larger percentage than a percentage increase in length.

6. The device of claim 1, wherein the biologically active agent is present in the device in an amount of greater than or equal to 0.01 w/w % versus a total weight of the device.

7. The device of claim 1, wherein the device is a catheter.

8. The device of claim 3, wherein the time period is less than or equal to 10 minutes.

9. The device claim 4, wherein the humectant comprises a sugar alcohol and/or a poloxamer.

10. The device of claim 1, comprising 0.1-30 w/w % humectant.

11. The device of claim 5, wherein the inner diameter and/or outer diameter increases by 1-20% while the length increases by 0.1-19%.

12. The device of claim 2, wherein the equilibrium water content state is greater than or equal to 20 w/w % and less than or equal to 80 w/w %.

13. The device of claim 1, wherein the polymeric material has a Young's elastic modulus of greater than or equal to 500 MPa in a dehydrated state and a Young's elastic modulus of less than or equal to 300 MPa and greater than or equal to 5 MPa at an equilibrium water content state.

14. The device of claim 1, wherein the plurality of pores have a mean pore size of less than or equal to 500 nm and greater than or equal to 10 nm.

15. The device of claim 1, wherein at least 50% of the plurality of pores have a diameter of less than or equal to 1 μm.

16. The device of claim 1, wherein the first water soluble polymer does not comprise covalent crosslinking agents.

17. The device of claim 1, wherein the first water soluble polymer is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

18. The device of claim 1, wherein the second water soluble polymer is selected from the group consisting of poly(vinyl alcohol), poly(acrylic acid), polyethylene glycol, or poly(vinyl pyrrolidone), poly(methacrylic sulfobetaine), poly(acrylic sulfobetaine), poly(methacrylic carboxybetaine), poly(acrylic carboxybetaine), povidone polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

19. The device of claim 1, wherein the device is configured for use with a medical device such as a catheter, a balloon, a shunt, a wound drain, an infusion port, a drug delivery device, a tube, a contraceptive device, a feminine hygiene device, an endoscope, a grafts, a pacemaker, an implantable cardioverter-defibrillator, a cardiac resynchronization device, a cardiovascular device lead, a ventricular assist device, an endotracheal tube, a tracheostomy tube, an implantable sensor, a ventilator pump, and an ophthalmic device.

20. The device of claim 19, wherein the catheter is selected from the group consisting of central venous catheters, peripheral central catheters, midline catheters, peripheral catheters, tunneled catheters, dialysis access catheters, urinary catheters, neurological catheters, percutaneous transluminal angioplasty catheters, and peritoneal catheters.

21. The device of claim 1, wherein the device and/or the polymeric material is substantially non-thrombogenic.

22. The device of claim 1, wherein the amount of the biologically active agent does not vary by more than 50% at a given arbitrary section across a cross-sectional area of the body portion and/or first water soluble polymer as compared to an average amount of the biologically active agent in the body portion and/or first water soluble polymer.

* * * * *